US009701667B2

(12) United States Patent
Keillor et al.

(10) Patent No.: US 9,701,667 B2
(45) Date of Patent: Jul. 11, 2017

(54) COUMARIN-BASED FLUOROGENIC AGENTS AND USES THEREOF FOR SPECIFIC PROTEIN LABELLING

(71) Applicant: UNIVERSITY OF OTTAWA, Ottawa (CA)

(72) Inventors: Jeffrey Keillor, Ottawa (CA); Yingche Chen, Edmonton (CA)

(73) Assignee: UNIVERSITY OF OTTAWA, Ottawa (CA)

( * ) Notice: Subject to any disclaimer, the term of this patent is extended or adjusted under 35 U.S.C. 154(b) by 0 days.

(21) Appl. No.: 14/704,289

(22) Filed: May 5, 2015

(65) Prior Publication Data

US 2015/0316557 A1 Nov. 5, 2015

Related U.S. Application Data

(60) Provisional application No. 61/988,383, filed on May 5, 2014.

(51) Int. Cl.
*C07D 405/14* (2006.01)
*G01N 33/58* (2006.01)
*G01N 33/542* (2006.01)
*G01N 33/68* (2006.01)

(52) U.S. Cl.
CPC ......... *C07D 405/14* (2013.01); *G01N 33/542* (2013.01); *G01N 33/582* (2013.01); *G01N 33/6803* (2013.01)

(58) Field of Classification Search
CPC .................................................. C07D 405/14
USPC ....................................................... 549/287
See application file for complete search history.

(56) References Cited

U.S. PATENT DOCUMENTS

| 7,700,375 | B2 | 4/2010 | Keillor et al. |
| 8,835,641 | B2 | 9/2014 | Keillor et al. |
| 9,006,459 | B2 | 4/2015 | Keillor et al. |
| 2004/0171014 | A1 | 9/2004 | Smith |
| 2006/0147948 | A1 | 7/2006 | Keillor et al. |

OTHER PUBLICATIONS

Honda et al Anal. Chimica Acta (1985) vol. 177 pp. 111-120.*
Kellner et al 2013 PLoS.*
Caron, Karine et al., "Dramatic Increase of Quench Efficiency in "Spacerless" Dimaleimide Fluorogens", Organic & Biomolecular Chemistry, 2011, vol. 9, pp. 185-197.
Chen, Yingche et al., "Coumarin-Based Fluorogenic Probes for No-Wash Protein Labeling", Angewandte Chemie International Edition, 2014, vol. 53, pp. 13785-13788.
Girouard, Stéphane et al., "Synthesis and Characterization of Dimaleimide Fluorogens Designed for Specific Labeling of Proteins", J. Am. Chem. Soc., 2005, vol. 127, pp. 559-566.
Guy, Julia et al., "Convergent Preparation and Photophysical Characterization of Dimaleimide Dansyl Fluorogens: Elucidation of the Maleimide Fluorescence Quenching Mechanism", J. Am. Chem. Soc., 2007, vol. 129, pp. 11969-11977.
Guy, Julia et al., "De Novo Helical Peptides as Target Sequences for a Specific, Fluorogenic Protein Labelling Strategy", Molecular Biosystems, 2010, vol. 6, pp. 976-987.
Honda, Kazumasa et al., "Evaluation of Fluorescent Compounds for Peroxyoxalate Chemiluminescence Detection", Analytica Chimica Acta, 1985, vol. 177, pp. 111-120.
Kanaoka, Yuichi et al., "Studies on Protein-Sulfhydryl Reagents. I. Synthesis of Benzimidazole Derivatives of Maleimide; Fluorescent Labeling of Maleimide", Chemical & Pharmaceutical Bulletin, 1964, vol. 12, No. 2, pp. 127-134.
Kellner, Stefanie et al., "Structure-Function Relationship of Substituted Bromomethylcoumarins in Nucleoside Specificity of RNA Alkylation", Plos One, 2013, vol. 8, Issue 7, pp. 1-10.
Langmuir, Margaret et al., "New Naphthopyranone Based Fluorescent Thiol Probes", Tetrahedron Letters, 1995, vol. 36, No. 23, pp. 3989-3992.
Meimetis, Labros G. et al., "Ultrafluorogenic Coumarin—Tetrazine Probes for Real-Time Biological Imaging", Angewandte Chemie International Edition, 2014, vol. 53, pp. 7531-7534.
Liang, F. et al. "Gene index analysis of the human genome estimates approximately 120,000." Nat. Genet. 2000, 25, 239-240.
Roest Crollius, H. et al. "Estimate of human gene number provided by genome-wide analysis using." Nat. Genet. 2000, 25, 235-238.
Ewing, B. et al. "Analysis of expressed sequence tags indicates 35,000 human genes." Nat. Genet. 2000, 25, 232-234.
Haughland, R. P. "Handbook of Fluorescent Probes and Research Chemicals." Molecular Probes. Eugene. Oreg. 1992, 5th Edn.
Sipple, T. O. "New fluorochromes for thiols: maleimide and iodoacetamide derivatives of 3-phenyl coumarin fluorophore." J. Histochem. Cytochem. 1981, 29, 314-316.
Corrie, J. E. T. "Thiol-reactive Fluorescent Probes for Protein Labelling." J. Chem. Soc. Perkin Trans. 1, 1994, 2975-2982.
Zhang, J. et al. "Creating New Fluorescent Probes for Cell Biology." Nature Rev. 2002, 3, 906-918.

(Continued)

*Primary Examiner* — Taofiq A Solola
(74) *Attorney, Agent, or Firm* — BCF LLP

(57) ABSTRACT

There are provided fluorescent labelling agents comprising a dimaleimide core connected to a fluorophore, processes for preparation thereof, and uses thereof for labelling and/or detection of specific protein targets. Fluorescent labelling agents comprising a compound having the structure of Formula I, and salts thereof, are described.

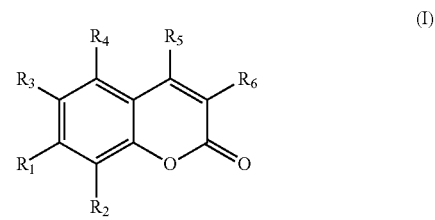

(I)

17 Claims, 14 Drawing Sheets

(56) References Cited

OTHER PUBLICATIONS

Tsien, R. Y. "The Green Fluorescent Protein." Annu. Rev. Biochem. 1998, 67, 509-544.
Griffin, B. A. et al. "Specific Covalent Labeling of Recombinant Protein Molecules Inside Live Cells." Science 1998, 281, 269-272.
Griffin, B. A. et al. "Fluorescent labeling of recombinant proteins in living cells with FlAsH." Methods Enzymol. 2000, 327, 565-578.
Gaietta, G. et al. "Multicolor and Electron Microscopic Imaging of Connexin Trafficking." Science 2002, 296, 503-507.
Girouard, S. et al. "Elaboration d'un fluorophore permettant une étude d'apposition protéique." M. Sc. Thesis. Université de Montréal. 2000.
Houle, M. H. et al. "Synthèse d'un composé fluorogénique permettant l'étude de l'apposition protéique." M. Sc. Thesis. Université de Montréal 2003.
Yang, J. R. et al. "Synthesis and Properties of a Maleimide Fluorescent Thiol Reagent Derived a Naphtopyranone." J. Heterocyclic Chem. 1991, 28, 1177.
Russo, A. et al. "Detection and quantitation of biological sulfhydryls." Methods Biochem. Anal. 1988, 33, 165-241.

\* cited by examiner

A

B

000# COUMARIN-BASED FLUOROGENIC AGENTS AND USES THEREOF FOR SPECIFIC PROTEIN LABELLING

CROSS-REFERENCE TO RELATED APPLICATIONS

This application claims the benefit of U.S. Provisional Patent Application No. 61/988,383 filed May 5, 2014, the entire contents of which are hereby incorporated by reference.

FIELD

The present disclosure broadly relates to novel fluorescent labelling agents. More specifically, but not exclusively, the present disclosure relates to fluorescent labelling agents comprising a dimaleimide core connected to a coumarin-based fluorophore and to a process for the preparation of such coumarin-based fluorogenic agents. The present disclosure also relates to the use of such fluorescent markers for the labelling and detection of specific protein targets.

BACKGROUND

The sequencing of the human genome has allowed the identification of a vast number of putative genes. However, the function of only a small number of these genes can be inferred from their primary sequences. New techniques and agents are needed to cope with the task of assigning functional roles to these gene products. This implies determination of how, when and where they are involved in specific biochemical pathways. Ideally, these techniques and agents will allow the rapid screening of substantial subsets of the sum of a genome's products. Some methods have been designed for broad and rapid screening, but they are generally limited to in vitro application and do not necessarily provide information that is relevant to the function of proteins in living cells. Visualizing and monitoring specific proteins, with minimal disruption of their biological function and distribution, remains one of the foremost challenges in chemical biology. More powerful methods of detection of specific proteins and monitoring their localization and interactions inside living cells are urgently required.

Fluorescent labelling of a specific protein of interest (POI) is one of the most widely used methods for studying expression, localization and trafficking. Several labelling techniques have been developed that involve, for example, the use of fluorescent dyes bearing reactive functional groups such as succinimidyl esters or maleimides, known to react with amines or thiols (see, for example, Takaoka, Y. et al., Angew. Chem. Int. Ed. 2013, 52(15), 4088-4106). However these techniques are typically non-specific, as many such functional groups exposed on the surface of any protein may be labeled, and they do not provide a general means for gathering information on specific protein targets.

Several fluorescent probes for imaging in cell biology have been developed, including small organic dyes, quantum dots, intrinsically fluorescent proteins, small genetically encoded tags that can be complexed with fluorochromes, and combinations of these probes (Giepmans, B. N. et al., Science 2006, 312, 217-24). The most widely applied methods for specific protein labelling include the following: 1) fluorescent protein fusion; 2) small-molecule labelling using protein targeting sequences; 3) enzyme substrate fusion; 4) small-molecule labelling using unnatural amino acids; and 5) small-molecule labelling using peptide targeting sequences.

The first of these methods involves the genetic fusion of target proteins to fluorescent proteins such as jellyfish green fluorescent protein (GFP). This technique has seen broad application because of its intrinsic specificity (O'Hare, H. M. et al., Curr OPin Struc Biol 2007, 17, 488-494; Zhang, J. et al., Nat Rev Mol Cell Bio 2002, 3, 906-918). However, there are limitations to this method, including GFP's slow folding, tendency to aggregate (Tsien, R. Y. et al., Annu Rev Biochem 1998, 67, 509-544) and its steric bulk, all of which can perturb the native biology of a protein of interest.

The second method comprises the genetic fusion of an enzyme to a protein of interest. The pendant enzyme, for example, phosphopantetheine transferase (PPtase) (Yin, J. et al., J Am Chem Soc 2004, 126, 7754-7755 George, N. et al., J Am Chem Soc 2004, 126, 8896-8897), O6-alkylguanine-DNA alkyltransferase (ATG) (Keppler, A. et al., Proc Natl Acad Sci USA 2004, 101, 9955-9959) or mutant haloalkane dehalogenase (HALO) (Los, G. V. et al., Acs Chem Biol 2008, 3, 373-82) can then be irreversibly labelled with a fluorescent ligand. However, with this method background labelling of native enzymes can be problematic and the native biology of a labelled protein of interest can be seriously affected by the bulk of pendant enzyme. Moreover, attenuation of the fluorescent signal is still a problem for the ATG-based method, while the PPtase-based method is restricted to the labelling of cell surface proteins.

In the third method, a protein of interest in fused with a short peptide sequence that serves as a substrate for an enzyme that catalyzes the covalent labelling of the peptide tag with a substrate that bears a reactive functional group. This reactive group must then be subsequently attached to a fluorophore though bioorthogonal chemistry. A Q-tag/transglutaminase system (Lin, C. W. et al., J Am Chem Soc 2006, 128, 4542-4543) and a biotin acceptor peptide/biotin ligase system (Sueda, S. et al., Chembiochem 2011, 12, 1367-1375) are the most successful examples of this class of labelling methods. This method can only be used for cell surface proteins because of the incompatibility of the enzymes in intracellular labelling.

The fourth method is to introduce unnatural amino acids in a site-specific manner (Wang, L. and Schultz, P. G., Chem Commun (Camb), 2002, 1-11). These unnatural amino acids usually contain ketones, azides or alkynes, which can undergo reactions through hydrazone formation, Staudinger reaction or azide/alkyne cycloaddition to add a fluorophore. This method has some advantages with respect to bioorthogonality and versatility for small molecule labelling. However, unnatural amino acid mutagenesis is not yet widely applicable and is highly dependent on host cell type.

Finally, the fifth method mentioned above is the use of small organic fluorophores for labelling proteins that harbour a specific, genetically encoded motif, representing the development of powerful alternative labelling methods (Chen, I. et al., Curr Opin Biotech 2005, 16, 35-40). Among these, the "FlAsH" method developed by Tsien and co-workers employs certain organoarsenic compounds that have been shown to form specific complexes with a target sequence containing four proximal cysteine residues (Zhang, J. et al., Nat Rev Mol Cell Bio 2002, 3, 906-918). This method demonstrates specific labelling using a minimised, small molecule approach. However, several drawbacks have been noted, including the inherent toxicity of organoarsenic compounds, background staining that may persist despite extensive washing, the sensitivity of the tetracysteine motif to oxidizing extracellular environments, and its tendency to form inactive intermolecular disulfide-linked aggregates.

Maleimide groups have long been used in applications that exploit their propensity to react selectively with thiol groups, undergoing Michael addition reactions through their C2=C3 double bond (Kanaoka, Y. et al., Chem. Pharm. Bull. 1964, 12, 127). Maleimides are also known to quench fluorescence, probably due to their participation in a photoinduced electron transfer (PET), allowing non-radiative relaxation of the fluorophore's excited state. The thiol addition reaction breaks the conjugation of the maleimide group, altering the energy levels of its molecular orbitals and removing its capacity to quench fluorescence (Guy, J. et al., J. Am. Chem. Soc. 2007, 129, 11969). These properties were demonstrated in the characterization of a naphthopyranone derivative bearing a maleimide group whose fluorescence increased dramatically upon reaction with glutathione (Langmuir, M. E. et al., Tetrahedron Lett. 1995, 36, 3989).

Labelling techniques based on the use of fluorescent dyes bearing reactive functional groups like maleimides, known to react with thiols, have been described (Tsien, R. Y., Annu. Rev. Biochem. 1998, 67, 509-544). However, these methods are typically non-specific, labelling the surface-exposed functional groups of many different proteins. Based on this chemical reaction, we previously developed a strategy for protein labelling based on a reactive unit bearing two maleimide groups linked to a fluorophore, such that fluorescence is quenched by photoinduced electron transfer (PET) until both maleimide groups undergo specific thiol addition reactions (Keillor, J. W. et al., Org Biomol Chem 2011, 9, 185-197; Keillor, J. W. et al., J Am Chem Soc 2007, 129, 11969-11977; Girouard, S. et al., J Am Chem Soc 2005, 127, 559-566). Additionally, complementary alpha-helical peptide tags have been designed, bearing two cysteine residues whose thiol side chains are appropriately positioned to react with the novel fluorogens (Keillor, J. W. et al., Mol Biosyst 2010, 6, 976-987). Genetically fusing these helical peptides to test proteins of interest (POI), we were able to selectively label the target sequence.

These early dimaleimide dyes react with the di-cysteine peptide tag faster than with two equivalents of other thiols such as glutathione (GSH) because the second maleimide-thiol reaction with the tag is an intramolecular reaction, while the second reaction with other thiol compounds is an intermolecular reaction. However, due to the high (millimolar) concentration of GSH inside living cells, some non-specific reaction with GSH is still possible, leading to background fluorescence. This may limit the application of these first generation fluorogens to cell surface labelling (Keillor, J. W. et al., Mol Biosyst 2010, 6, 976-987), highlighting the need for more selective labelling agents that can be used for intracellular applications.

It was also reported previously that efficient quenching was observed with a dansyl-based fluorogen (Keillor, J. W. et al., Org Biomol Chem 2011, 9, 185-197). However, dansyl is an environment-sensitive fluorophore and its excitation and emission wavelengths do not correlate well with the filter sets of most fluorescent microscopes.

SUMMARY

It is an object of the present invention to ameliorate at least some of the deficiencies present in the prior art.

Embodiments of the present technology have been developed based on the inventors' appreciation that there is a need for improved fluorogenic compounds for labelling proteins of interest (POIs).

The present disclosure relates broadly to novel fluorescent labelling compounds comprising a dimaleimide core connected to a fluorophore, and to processes for preparation of such fluorescent labelling compounds and uses thereof. We report herein the design and synthesis of a small library of novel fluorogen compounds based on coumarin, a commonly used fluorophore. Compounds have been screened for their selectivity for protein of interest (POI) labelling. In one embodiment of the invention, there are provided coumarin-based "turn-on" fluorogens that exhibit negligible background reactivity and/or high selectivity for site-specific protein labelling, and uses thereof for the labelling and detection of specific protein targets. In some embodiments, fluorogenic compounds provided herein are capable of intracellular application.

In a broad aspect, there are provided fluorescent labelling agents of Formula I:

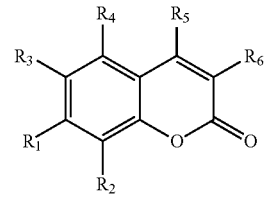

Formula I wherein:

$R_1$ is $OR_1'$ or $NR_2'R_3'$, wherein $R_1'$, $R_2'$ and $R_3'$ are independently selected from hydrogen, alkyl, alkenyl, alkynyl, cycloalkyl, cycloalkenyl, cycloalkynyl, aryl, alkaryl, arylalkyl, and carboxy alkyl, alkyl being optionally substituted by hydroxyl, amino, carboxyl, carboxylic ester, amide, carbamate, or aminoalkyl; or $R_1'$ and $R_2$ or $R_1'$ and $R_3$ come together to form a 5, 6 or 7-membered ring which is selected from aryl, heterocyclic, heteroaryl, and heteroaromatic; or $R_2'$, $R_2$, $R_3'$, and $R_3$ come together independently to form at least one 5, 6 or 7-membered ring which is selected from aryl, heterocyclic, heteroaryl and heteroaromatic;

$R_2$, $R_3$ and $R_4$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, alkyl being optionally substituted by hydroxyl, amino, carboxyl, carboxylic ester, amide, carbamate, or aminoalkyl;

$R_5$ and $R_6$ are independently selected from hydrogen, halogen, alkyl, alkoxy, keto, carboxylate, carboxylic ester, carbamate, amide, amino, alkylamino, polyether, alkylthio, cyano, nitro, sulfonyl, $X_1$, and $X_2$, wherein one of $R_5$ and $R_6$ is $X_1$ or $X_2$, and alkyl is optionally substituted by hydroxyl, amino, carboxyl, carboxylic ester, amide, carbamate, or aminoalkyl;

$X_1$ is

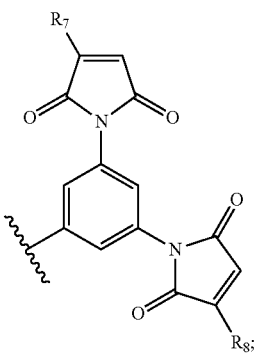

$X_2$ is

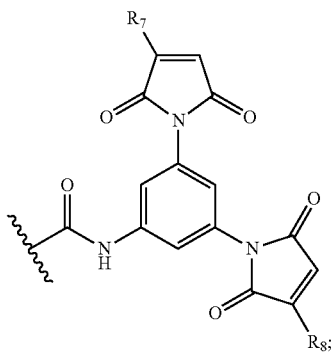

and $R_7$ and $R_8$ are independently $R_9$ or $OR_{10}$, wherein $R_9$ is selected from hydrogen, halogen, and alkyl, alkyl being optionally substituted by hydroxyl, amino, carboxyl, carboxylic ester, amide, carbamate, or aminoalkyl, and $R_{10}$ is alkyl, alkyl being optionally substituted by hydroxyl, amino, carboxyl, carboxylic ester, amide, carbamate, or aminoalkyl.

In some embodiments, only one of $R_5$ and $R_6$ is $X_1$ or $X_2$. In some embodiments, $R_5$ and $R_6$ are both $X_1$ or $X_2$, or one of $R_5$ and $R_6$ is $X_1$ and the other is $X_2$.

In an embodiment, there is provided a fluorescent labelling agent comprising a compound of Formula II, or a salt thereof:

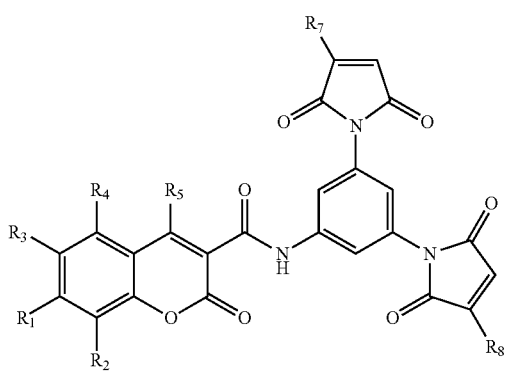

(II)

wherein $R_1$, $R_2$, $R_3$, $R_4$, $R_7$, and $R_8$ are as defined above; and $R_5$ is selected from hydrogen, halogen, alkyl, alkoxy, keto, carboxylate, carboxylic ester, carbamate, amide, amino, alkylamino, polyether, alkylthio, cyano, nitro, and sulfonyl, wherein alkyl is optionally substituted by hydroxyl, amino, carboxyl, carboxylic ester, amide, carbamate, or aminoalkyl.

In another embodiment, there is provided a fluorescent labelling agent comprising a compound of Formula III, or a salt thereof:

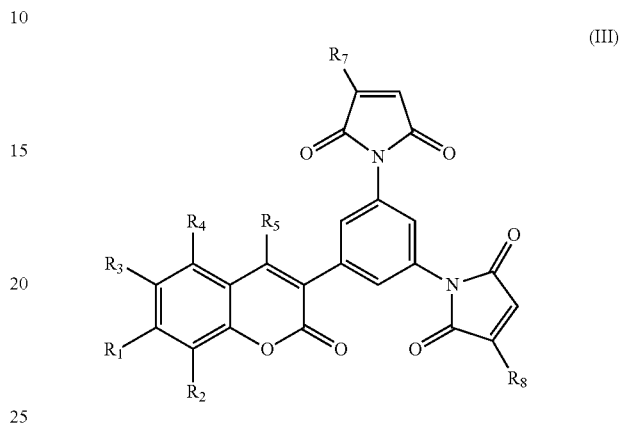

(III)

wherein $R_1$, $R_2$, $R_3$, $R_4$, $R_7$, and $R_8$ are as defined above; and $R_5$ is selected from hydrogen, halogen, alkyl, alkoxy, keto, carboxylate, carboxylic ester, carbamate, amide, amino, alkylamino, polyether, alkylthio, cyano, nitro, and sulfonyl, wherein alkyl is optionally substituted by hydroxyl, amino, carboxyl, carboxylic ester, amide, carbamate, or aminoalkyl.

In some embodiments, at least one of $R_7$ and $R_8$ is $OR_{10}$. In some embodiments, when $R_7$ is $OR_{10}$, $R_8$ is $R_9$. In some embodiments, when $R_7$ is $R_9$, $R_8$ is $OR_{10}$. In some embodiments, $R_7$ and $R_8$ are the same. In some embodiments, $R_9$ and $R_{10}$ are the same. In some embodiments, $R_5$ is $X_1$ or $X_2$ and $R_6$ is hydrogen. In alternative embodiments, $R_5$ is hydrogen and $R_6$ is $X_1$ or $X_2$. In further embodiments, $R_5$ is hydrogen; $R_6$ is $X_2$; $R_7$ is methyl; and $R_8$ is methoxy. In still further embodiments, $R_5$ is hydrogen; $R_6$ is $X_2$; and $R_7$ and $R_8$ are methoxy.

In some embodiments, $R_2$, $R_3$, and $R_4$ are hydrogen. In some embodiments, $R_5$ is hydrogen. In some embodiments, $R_2$, $R_3$, $R_4$ and $R_5$ are hydrogen.

In some embodiments, $R_1$ is selected from:

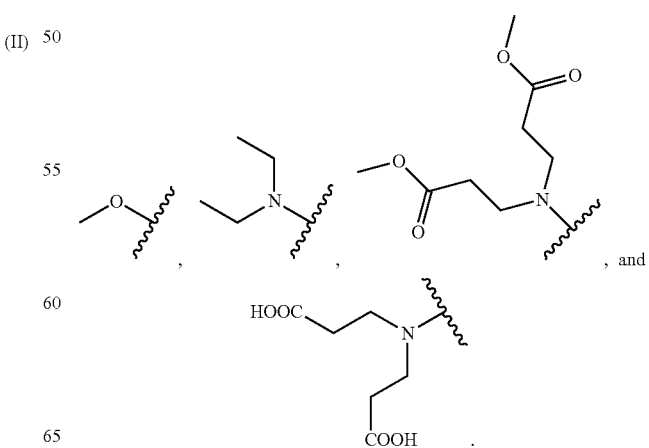

In some embodiments, $R_1$ is selected from:

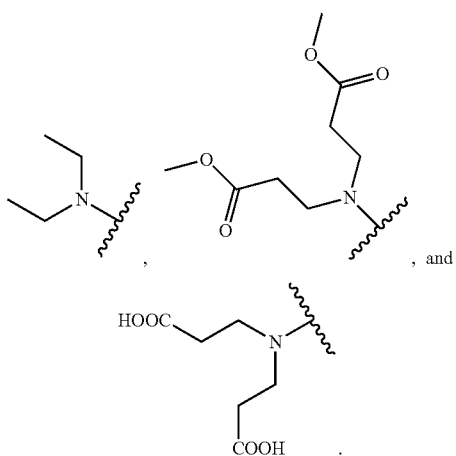

, and

In some embodiments, $R_1$ is an amino substituent, and oxygen substituent, or an ester. In some embodiments, $R_1$ is selected from:

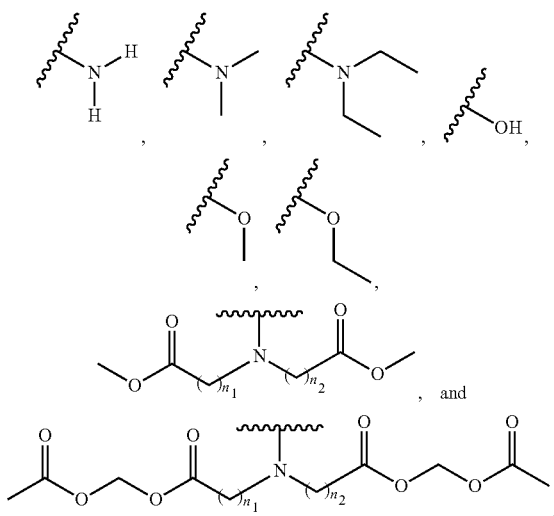

, and where $n_1$ and $n_2$ are independently 1 or higher than 1. In some embodiments, $n_1$ and $n_2$ are 1 to 5, 1 to 10, 1 to 20, or 1 to 50.

In some embodiments, $R_2$, $R_3$, and $R_4$ are hydrogen, and $R_1$ is selected from:

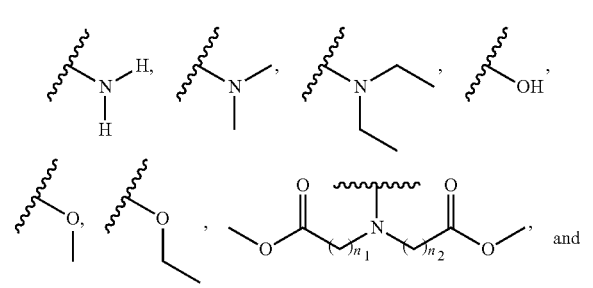

, and

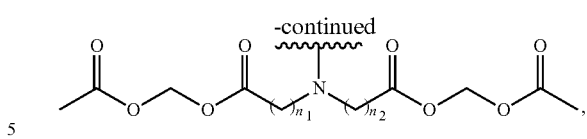

where $n_1$ and $n_2$ are independently 1 or higher than 1. In some embodiments, $n_1$ and $n_2$ are 1 to 5, 1 to 10, 1 to 20, or 1 to 50.

In some embodiments, $R_7$ is methyl and $R_8$ is methoxy. In some embodiments, both $R_7$ and $R_8$ are methoxy.

In some embodiments, $R_2$, $R_3$, and $R_4$ are hydrogen, and $R_1$ is selected from:

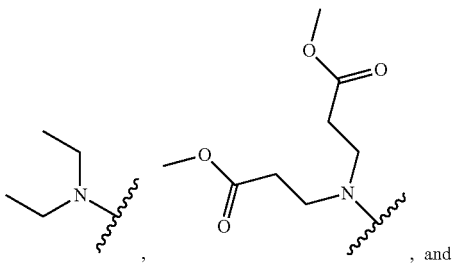

, and

In some embodiments, $R_2$, $R_3$, and $R_4$ are hydrogen, and $R_1$ is selected from:

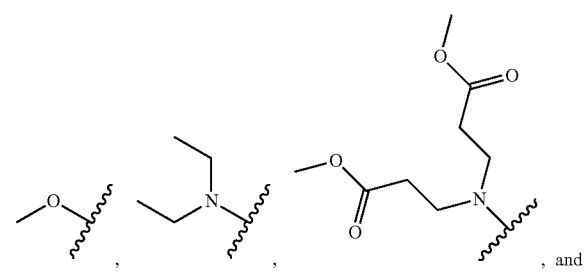

, and

In some embodiments, $R_2$, $R_3$, $R_4$, and $R_5$ are hydrogen; $R_7$ is methyl or methoxy; $R_8$ is hydrogen, methyl or methoxy; and $R_1$ is selected from:

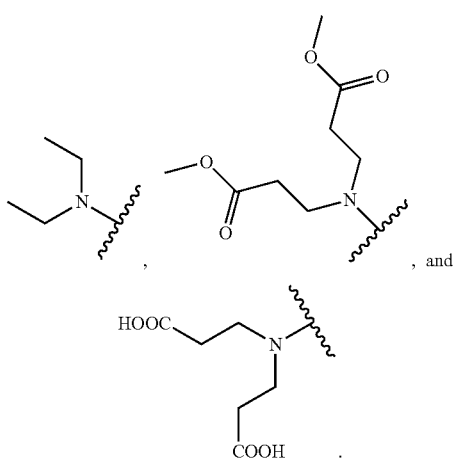
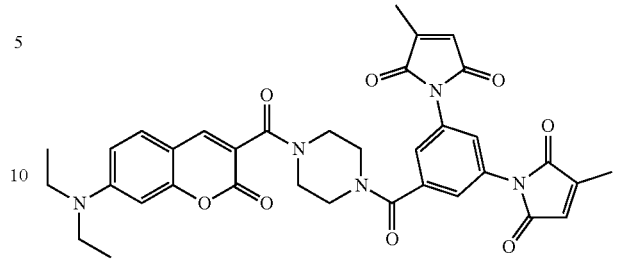
In some embodiments, $R_2$, $R_3$, $R_4$, and $R_5$ are hydrogen; $R_7$ is methyl or methoxy; $R_8$ is hydrogen, methyl or methoxy; and $R_1$ is selected from:
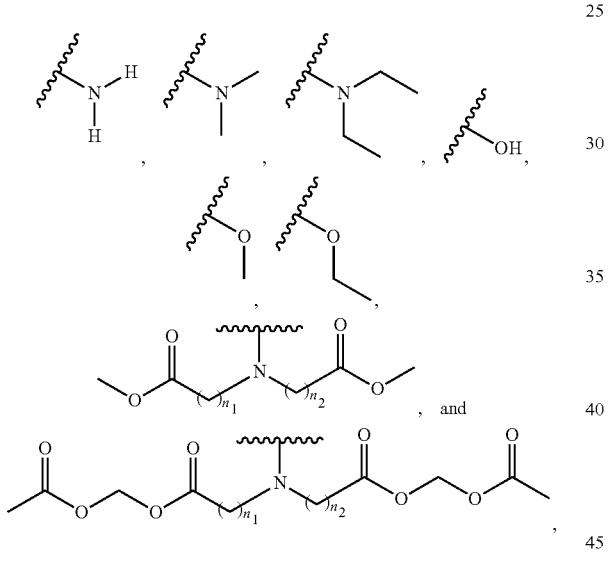
where $n_1$ and $n_2$ are independently 1 or higher than 1. In some embodiments, $n_1$ and $n_2$ are 1 to 5, 1 to 10, 1 to 20, or 1 to 50.
In an embodiment, there are provided fluorescent labelling agents comprising one or more compound selected from:
YC24
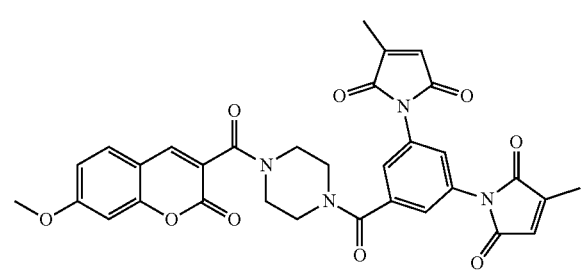
YC25
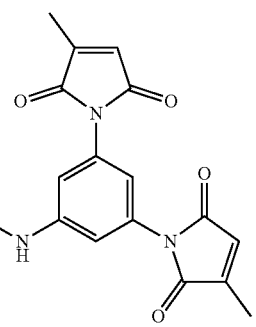
YC26
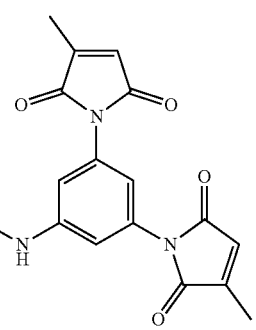
YC5
YC9
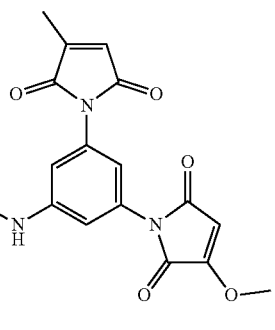

-continued

YC9M

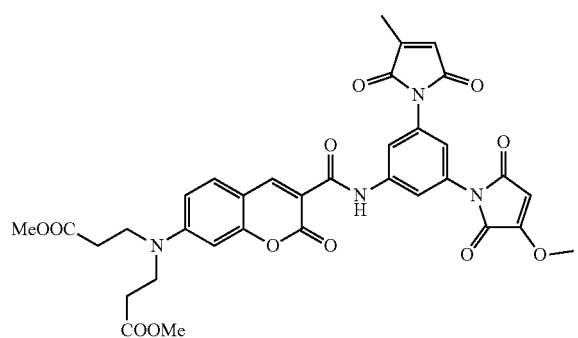

YC9A

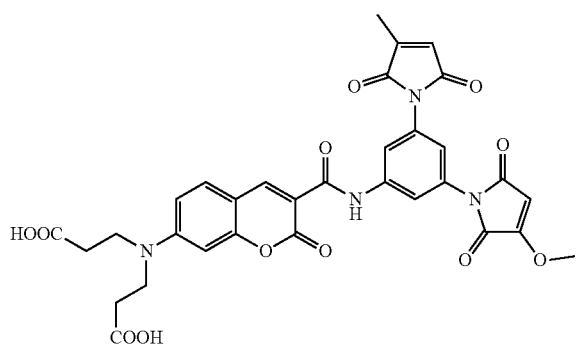

YC21A

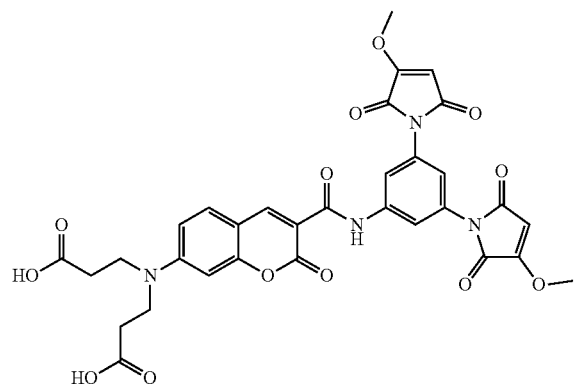

-continued

YC15-YC19

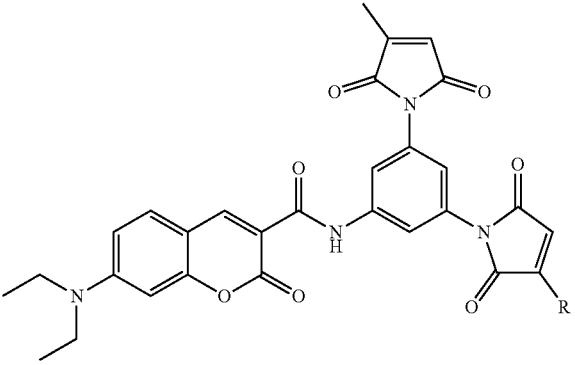

R = Et YC15
$^i$Pr YC16
OEt YC17
Br YC18
O$^i$Pr YC19

YC20

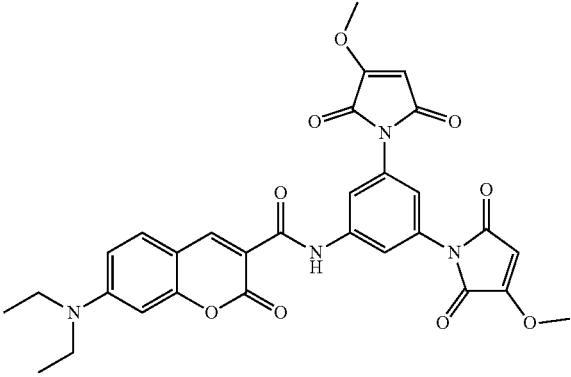

YC21M

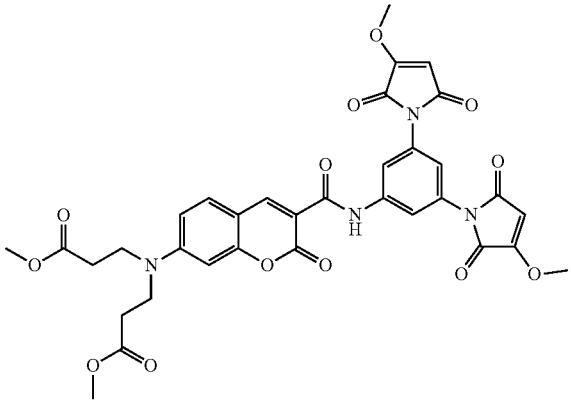

and salts thereof.

In some embodiments of the technology, fluorescent labelling agents are not toxic to animal cells, e.g., fluorescent labelling agents are not toxic to mammalian cells, invertebrate cells, vertebrate cells, human cells, rodent cells, mouse cells, rat cells, insect cells, nematode cells, or fish cells.

In some embodiments of the technology, a fluorescent labelling agent's fluorescence is quenched when the fluorescent labelling agent is in its conjugated form, and not quenched in the form of a thiol adduct. In some embodiments, the fluorescence of the fluorescent labelling agent increases after reaction with sulfhydryl groups on a protein. In some embodiments, a fluorescent labelling agent specifically reacts with two Cys residues separated by about 10 Å or a dC10α tag. In some embodiments, a fluorescent labelling agent does not react appreciably with cellular proteins or with glutathione (GSH). In some embodiments, a fluorescent labelling agent has one or more of the following characteristics: aqueous solubility; non-toxic to animal cells; low background fluorescence before reaction with a target protein; increased fluorescence after reaction with a target protein; bright fluorescence after reaction with a target protein; cell permeability; non-reactivity with GSH; and specific binding to two sulfhydryl residues separated by about 10 Å or a dC10α tag.

In an aspect, there are provided herein methods for labelling and/or detecting a target protein, comprising: a) contacting the target protein with a fluorescent labelling agent provided herein, under conditions where the fluorescent labelling agent reacts with sterically unhindered sulfhydryl groups on the target protein; and b) detecting a fluorescent signal from the fluorescent labelling agent, wherein the fluorescence of the fluorescent labelling agent is quenched in the absence of reaction with the target protein, and detection of the fluorescent signal indicates that reaction of the fluorescent labelling agent with the target protein.

In an embodiment, there are provided methods for labelling and/or detecting a target protein, comprising: a) contacting the target protein with a fluorescent labelling agent provided herein, under conditions where the fluorescent labelling agent reacts with sterically unhindered sulfhydryl groups on the target protein; and b) detecting a fluorescent signal from the fluorescent labelling agent, wherein the fluorescence of the fluorescent labelling agent increases after reaction with the target protein.

In embodiments of methods of the invention, the contacting may occur in vivo, ex vivo, or in vitro. In some embodiments, the contacting may occur in a cultured cell expressing a protein of interest (POI) or target protein. The target protein may be, for example, an intracellular protein, or an extracellular or cell-surface protein. The contacting may occur intracellularly in some embodiments.

In some embodiments, a target protein comprises two Cys residues separated by about 10 Å, e.g., dC10α tag. For example, a target protein may have been genetically engineered to comprise two Cys residues separated by about 10 Å, or a dC10α tag.

There are also provided herein methods for live imaging of a target protein, comprising: a) contacting the target protein with a fluorescent labelling agent provided herein, under conditions where the fluorescent labelling agent reacts with sterically unhindered sulfhydryl groups on the target protein; and b) detecting a fluorescent signal from the fluorescent labelling agent, wherein the fluorescence of the fluorescent labelling agent increases after reaction with the target protein, or is detectable only after reaction with the target protein. In some embodiments, the target protein has been engineered to comprise two Cysteine residues separated by about 10 Å or a dC10α tag prior to the contacting step.

In a further aspect, there are provided kits for labelling and/or detecting a target protein, comprising a fluorescent labelling agent provided herein, and instructions for use thereof.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
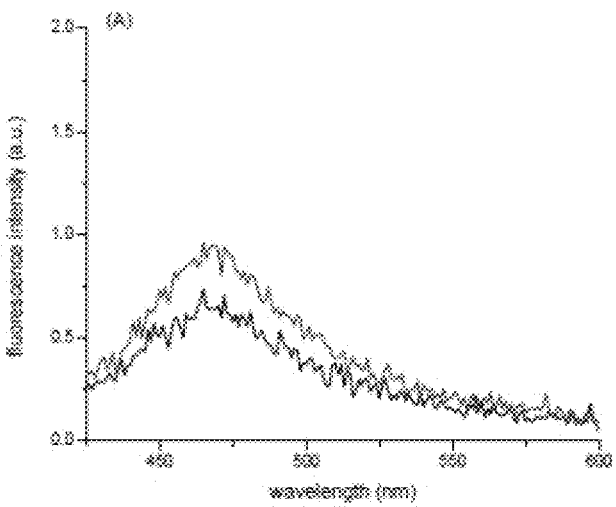
FIG. 1 is an illustration of the fluorescent emission spectra of 25 μM of fluorogens (A) YC24, (B) YC25, (C) YC5 before (black line) and after (red line) labelling with 25 μM model target protein MBP-dC10 in 50 mM HEPES buffer (pH 7.4). $\lambda_{ex}$=440 nm.
Figure 1:
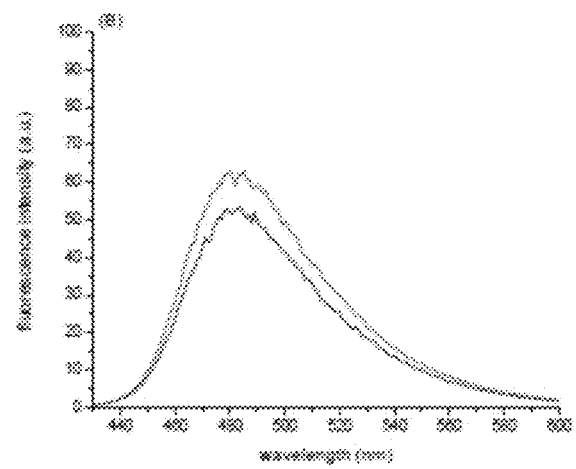
Figure 1:
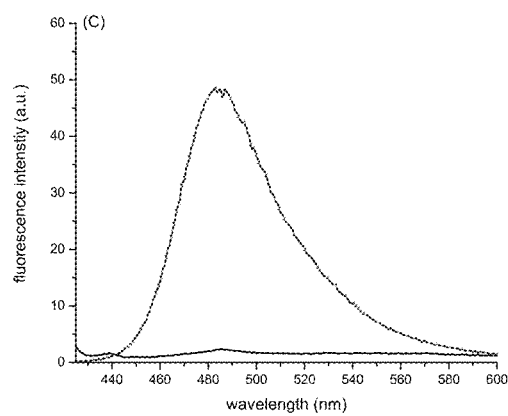

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "alkyl" can be straight-chain or branched. Examples of alkyl residues containing from 1 to 6 carbon atoms are methyl, ethyl, propyl, butyl, pentyl, hexyl, the n-isomers of all these residues, isopropyl, isobutyl, isopentyl, neopentyl, isohexyl, 3-methylpentyl, sec-butyl, tert-butyl, or tert-pentyl. Alkyl residues may be substituted or unsubstituted. In some embodiments, for example, alkyl may be substituted by hydroxyl, amino, carboxyl, carboxylic ester, amide, carbamate, or aminoalkyl.

As used herein, the term "cycloalkyl" can be monocyclic or polycyclic, for example monocyclic, bicyclic or tricyclic, i.e., they can for example be monocycloalkyl residues, bicycloalkyl residues and tricycloalkyl residues, provided they have a suitable number of carbon atoms and the parent hydrocarbon systems are stable. A bicyclic or tricyclic cycloalkyl residue has to contain at least 4 carbon atoms. In an embodiment, a bicyclic or tricyclic cycloalkyl residue contains at least 5 carbon atoms. In a further embodiment, a bicyclic or tricyclic cycloalkyl residue contains at least 6 carbon atoms and up to the number of carbon atoms specified in the respective definition. Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_1$-$C_4$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

As used herein, the term "aryl" means an aromatic substituent that is a single ring or multiple rings fused together. When formed of multiple rings, at least one of the constituent rings is aromatic. In an embodiment, aryl substituents include phenyl, naphthyl and anthracyl groups.

The term "heteroaryl", as used herein, is understood as being unsaturated rings of five or six atoms containing one or two O- and/or S-atoms and/or one to four N-atoms, provided that the total number of hetero-atoms in the ring is 4 or less. The heteroaryl ring is attached by way of an available carbon or nitrogen atom. Non-limiting examples of heteroaryl groups include 2-, 3-, or 4-pyridyl, 4-imidazolyl, 4-thiazolyl, 2- and 3-thienyl, and 2- and 3-furyl. The term "heteroaryl", as used herein, is understood as also including bicyclic rings wherein the five or six membered ring containing O, S and N-atoms as defined above is fused to a benzene or pyridyl ring. Non-limiting examples of bicyclic rings include but are not limited to 2- and 3-indolyl as well as 4- and 5-quinolinyl.

In a broad aspect, the present disclosure relates to fluorogens or fluorogenic reagents formed as the combination of a coumarin derivative and a linker bearing a dimaleimide reactive unit. Compounds presented herein are designed to provide coumarin fluorophores that demonstrate efficient quenching and "turn on" when bound to a protein, providing fluorescent labelling reagents.

Maleimide groups are known for undergoing specific thiol addition reactions and have been widely applied, although typically non-specifically, in protein labelling. Maleimide groups are also known to quench fluorescence in their conjugated form, but not as their thiol adduct products. Accordingly, fluorogenic labelling agents provided herein are designed to comprise a fluorophore and a dimaleimide moiety, such that their latent fluorescence is quenched by photoinduced electron transfer (PET) until both maleimide groups undergo specific thiol addition reactions. The quenching efficiency of the dimaleimide allows the fluorogenic labelling agents provided herein to be used as "turn-on" agents whose fluorescence is induced, or "turned-on", upon reaction with a specific POI that has been linked to, e.g., genetically fused to, an appropriate Cysteine-containing tag. It is noted that linkage of the fluorophore and the dimaleimide scaffold is critical for quenching efficiency.

A dimaleimide fluorogen must undergo two thiol addition reactions before its latent fluorescence is restored. For fluorogenic labelling agents provided herein, a fluorogenic response is selective for a POI genetically fused to a short peptide sequence that presents two Cys residues, separated by two turns of the α-helix (~10 Å) (such as, for example, a dC10α tag), because very few native proteins present two free Cys residues on their surface, ~10 Å apart. This selectively allows use of the fluorogenic labelling agents specifically to label POIs having an appropriate two-Cysteine tag (such as a dC10α tag).

High specificity and/or absence of non-specific, background reactivity, as well as efficient quenching of fluorescence for an unbound fluorogen, are required in order to provide selective labelling agents capable of intracellular application. Fluorogenic labelling agents provided herein have been designed to increase their selectivity for site-specific protein labelling, reduce their non-specific background reactivity, and/or increase their quenching efficiency, in order to provide improved agents for fluorescent labelling of a specific protein of interest (POI). In an embodiment, fluorescent labelling agents provided herein demonstrate sufficiently high selectivity, sufficiently low background reactivity, and/or sufficiently efficient quenching that they can be used for intracellular labelling of a specific POI.

Fluorescent labelling agents described herein provide some or all of the following advantages. First, in some embodiments, they are highly specific for target protein labelling; even in the presence of high concentrations of GSH or other thiol compounds, they do not react to give an increased fluorescent signal. Thus, they can be used for intracellular labelling, where other fluorogens that do not show this high specificity cannot be used. It is noted that some dimaleimide fluorogens which have been described previously demonstrate lower specificity and/or higher background reactivity and are therefore not suitable for intracellular labelling (presumably because a dimaleimide fluorogen could react with one Cys residue of an adventitious protein followed by a reaction with one equivalent of the ubiquitous GSH, or with two equivalents of GSH, leading to a non-specific fluorogenic reaction). Thus, in some embodiments, fluorogenic labelling agents presented herein are improved as compared to other dimaleimide fluorogens that have been described, having improvement in one or more of the following characteristics: specificity; background reactivity; and quenching efficiency. Second, in some embodiments, fluorescent labelling agents provided herein are non-toxic, which makes them advantageous for cellular application and safer to use than other known labelling agents such as, for example, organoarsenic compounds (e.g., "FlAsH" labelling agents). Third, in some embodiments, fluorescent labelling agents provide highly efficient quenching of latent fluorescence of the fluorophore. In some embodiments, the latent fluorescence of the fluorophore (i.e., fluorescence before reaction with the POI, or before labelling) is fully quenched. In some embodiments, the latent fluorescence is fully quenched, and the fluorogen nevertheless produces a strong fluorescent signal after labelling or reaction with a POI. The fluorescent labelling agents provided herein are based on coumarin and derivatives thereof; in some embodiments, the latent fluorescence of coumarin or a coumarin derivative is fully quenched, and the fluorogens give strong fluorescent signal after labelling. Fourth, with coumarin or a derivative thereof as fluorophore, fluorescent labelling agents are not sensitive to the protein labelling environment and are amenable to fluorescence microscopy experiments, since their excitation and emission correlate with the filter sets available in most fluorescence microscopes.

In addition, fluorescent labelling agents described herein possess some or all of the following advantages of dimaleimide compounds: 1) the dicysteine tags used in the methods of the present disclosure have a far smaller potential to disrupt the localization and interactions of native proteins than the relatively large protein fragments used in other methods; 2) the signal reaction being a simple reaction between a pair of protein-thiols and a thiol-selective small molecule fluorogen, it is less sensitive to the effects of variation of cellular conditions than the folding of fluorescent protein applications; 3) the inherent flexibility of the method of the present disclosure to design fluorogenic probes with many different spectral qualities that react specifically with different protein targets provides for the encoding of protein interactions in a variety of ways, including the potential for multiplexed protein expression analysis in vivo and in vitro; 4) fluorescent labelling agents and methods are not limited in their application to a single assay, but are capable of being used in a series of assays in which the fluorogen and protein target sequence may be chosen according to their efficacy in a particular cell type appropriate to the study of the interactions of a given class of proteins; 5) methods of the disclosure can be automated and tailored for high-throughput fluorescent screening; and 6) markers are designed at the level of the atomic structure and three-dimensional conformation of the target protein motifs, allowing control over the flexibility and specificity of probe fragments (i.e., sulfhydryl tags) used.

"Coumarin derivative" is intended to encompass any chemically stable derivative of coumarin that is fluorogenic and suitable for linking to a dimaleimide moiety, as well as coumarin itself (also known as 2H-chromen-2-one or 1-benzopyran-2-one). Many coumarin derivatives are known in the art, such as but not limited to auraptene; ensaculin; umbelliferone coumarinoids; coumarin derivatives having a carboxylic acid at the 3-position; coumarin derivatives having an electron donating group at the 7-position such as 7-hydroxy, 7-amino, 7-diethylamino, 7-piperidine; coumarin derivatives having an alkyl group, e.g., methyl, at the 4-position such as 7-amino-4-methylcoumarin; etc. In some embodiments, a coumarin derivative includes an electron donating group (e.g., hydroxy, alkoxy, amino and substituted amino groups). In some embodiments, a coumarin derivative includes a fused ring substituent, as in coumarin 343, for example. Additional fluorescent coumarin derivatives are known in the art. In one embodiment, a coumarin derivative is 7-methoxycoumarin-3-carboxylic acid. In another embodiment, a coumarin derivative is 7-diethylaminocoumarin-3-carboxylic acid. These coumarin derivatives are named for exemplary purposes only and are not meant to limit the compounds of the invention, as other fluorescent coumarin derivatives can be used in flurogenic labelling agents of the invention.

"Dimaleimide moiety" is intended to encompass a dimaleimide reactive unit capable of linking to a coumarin derivative. It will be appreciated by the skilled artisan that many derivatives of a dimaleimide moiety exist or can be made. Such derivatives retaining ability to link to a fluorogenic coumarin derivative and provide efficient quenching are intended to be encompassed by the present invention.

Figure 9:
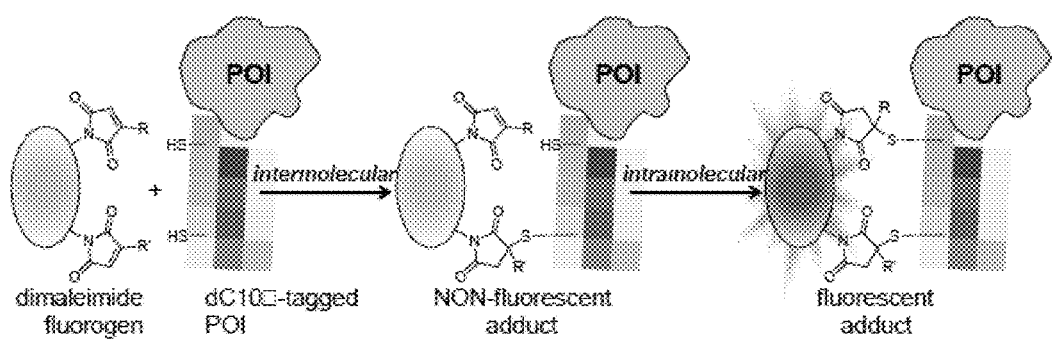
FIG. 9 shows a schematic diagram of protein labelling (where a specific protein of interest (POI) is labelled) with dimaleimide fluorogens.

A dimaleimide moiety may be asymmetric or symmetric. An "asymmetric" dimaleimide moiety is one wherein the intrinsic reactivity of one maleimide is reduced, such that its intermolecular reaction is suppressed (see FIG. 9). A non-limiting example of an asymmetric dimaleimide moiety is the following:

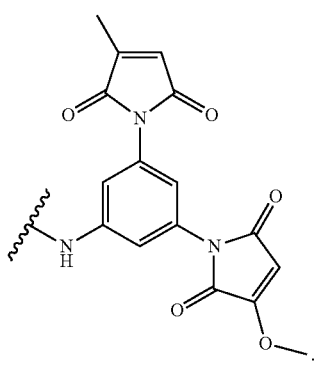 [SMILES: *Nc1cc(N2C(=O)C=C(C)C2=O)cc(N2C(=O)C=C(OC)C2=O)c1]

A non-limiting example of a symmetric dimaleimide moiety is the following:

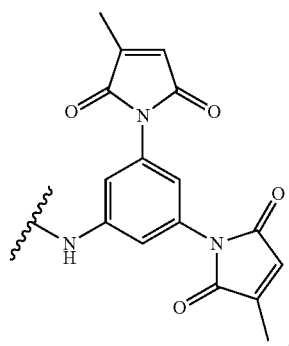

In some embodiments, fluorogenic labelling agents provided herein comprise an asymmetric dimaleimide moiety. Without wishing to be limited by theory, it is believed that, in an asymmetric dimaleimide moiety, the intrinsic reactivity of one maleimide is greatly reduced, effectively suppressing its intermolecular reaction. However, in the reaction with an appropriate dithiol, the reaction of the less reactive maleimide is intramolecular, and efficiently accelerated by the high effective molarity of the adjacent second thiol (see FIG. 9). It has been suggested previously that the reactivity of a maleimide group bearing an electron-donating substituent may be suitably attenuated (Girouard, S. et al., J Am Chem Soc 2005, 127, 559-566). Herein, we describe the synthesis and characterisation of coumarin-based labelling reagents bearing such an asymmetric dimaleimide moiety, and compare these to symmetric analogues.

In an embodiment, therefore, a fluorogenic labelling agent comprises an asymmetric dimaleimide moiety. In another embodiment, a fluorogenic labelling agent comprises a symmetric dimaleimide moiety.

It should be understood that a dimaleimide moiety may be covalently linked to a coumarin derivative directly or via a linker. Many linker moieties are known in the art and may be used in compounds of the invention. In an embodiment, a linker is piperazine (diamide). Other non-limiting examples of linkers include sulfonamide, alkyne (e.g., acetylene linkage), triazole, urea, thiourea, and ketone. In another embodiment, a coumarin derivative is linked directly to a dimaleimide moiety by a direct amide linkage with the common aryl on the dimaleimide moiety. In another embodiment, a coumarin derivative is linked directly to a dimaleimide aryl moiety. In some embodiments, a coumarin derivative is linked directly to a dimaleimide moiety by a single bond, such as diarylamine, diarylether, and diarylthioether.

For compounds provided herein, it is intended that, in some embodiments, salts thereof are also encompassed. Those skilled in the art will appreciate that many salt forms (e.g., TFA salt, tetrazolium salt, sodium salt, potassium salt, etc,) are possible; appropriate salts are selected based on reaction and labelling conditions and other considerations known in the art. It is intended that suitable salts of the compounds presented herein are encompassed by the present invention.

In an embodiment, there is provided a fluorogenic labelling agent of Formula I, or a salt thereof:

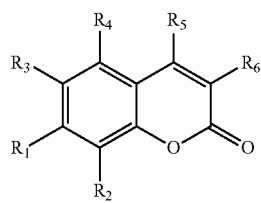

(I)

where:

$R_1$ is $OR_1'$ or $NR_2'R_3'$, wherein $R_1'$, $R_2'$ and $R_3'$ are independently selected from hydrogen, alkyl, alkenyl, alkynyl, cycloalkyl, cycloalkenyl, cycloalkynyl, aryl, alkaryl, arylalkyl, and carboxy alkyl, and $R_1'$, $R_2'$ and $R_3'$ are optionally substituted independently by hydroxyl, amino, carboxyl, carboxylic ester, amide, carbamate, or aminoalkyl; or $R_1'$ and $R_2$ or $R_1'$ and $R_3$ come together to form a 5, 6 or 7-membered ring which is selected from aryl, heterocyclic, heteroaryl, and heteroaromatic; or $R_2'$, $R_2$, $R_3'$, and $R_3$ come together independently to form at least one 5, 6 or 7-membered ring which is selected from aryl, heterocyclic, heteroaryl and heteroaromatic;

$R_2$, $R_3$ and $R_4$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, and $R_2$, $R_3$, and $R_4$ are optionally substituted independently by hydroxyl, amino, carboxyl, carboxylic ester, amide, carbamate, or aminoalkyl;

$R_5$ and $R_6$ are independently selected from hydrogen, halogen, alkyl, alkoxy, keto, carboxylate, carboxylic ester, carbamate, amide, amino, alkylamino, polyether, alkylthio, cyano, nitro, sulfonyl, $X_1$, and $X_2$, wherein one of $R_5$ and $R_6$ is $X_1$ or $X_2$, and $R_5$ and $R_6$ are optionally substituted independently by hydroxyl, amino, carboxyl, carboxylic ester, amide, carbamate, or aminoalkyl;

X$_1$ is

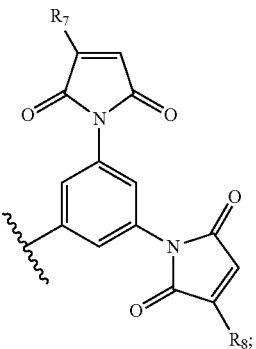

X$_2$ is

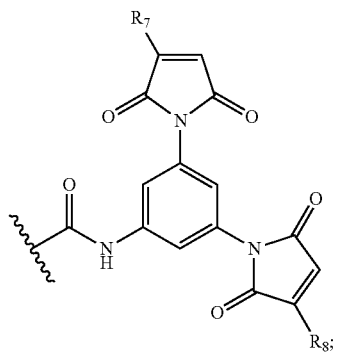

and

R$_7$ and R$_8$ are independently R$_9$ or OR$_{10}$, wherein R$_9$ is selected from hydrogen, halogen, and alkyl, alkyl being optionally substituted by hydroxyl, amino, carboxyl, carboxylic ester, amide, carbamate, or aminoalkyl, and R$_{10}$ is alkyl, alkyl being optionally substituted by hydroxyl, amino, carboxyl, carboxylic ester, amide, carbamate, or aminoalkyl.

In some embodiments, only one of R$_5$ and R$_6$ is X$_1$ or X$_2$. In some embodiments, R$_5$ and R$_6$ are both X$_1$ or X$_2$, or one of R$_5$ and R$_6$ is X$_1$ and the other is X$_2$.

In some embodiments, R$_9$ and R$_{10}$ are the same. In some embodiments, R$_9$ and R$_{10}$ are different.

In some embodiments, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are may be substituted by hydroxyl, amino, carboxyl, carboxylic ester, amide, carbamate, or aminoalkyl.

In an embodiment, at least one of R$_7$ and R$_8$ is OR$_{10}$. In another embodiment, when one of R$_7$ and R$_8$ is OR$_{10}$, then the other is R$_9$. In other words, in an embodiment, when R$_7$ is OR$_{10}$, R$_8$ is R$_9$. In another embodiment, when R$_8$ is OR$_{10}$, R$_7$ is R$_9$. In some embodiments, R$_7$ and R$_8$ are the same. In some embodiments, R$_9$ and R$_{10}$ are the same.

In some embodiments, R$_5$ and R$_6$ are both X$_1$ or X$_2$, or one of R$_5$ and R$_6$ is X$_1$, and the other is X$_2$.

In some embodiments, R$_2$, R$_3$, and R$_4$ are hydrogen.

In some embodiments, R$_1$ is selected from:

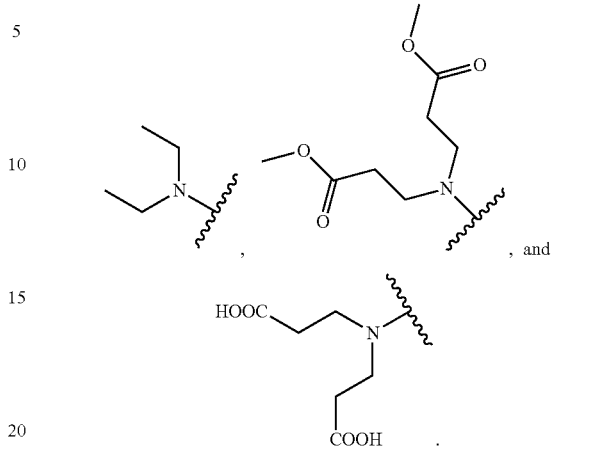

In some embodiments, R$_1$ is selected from:

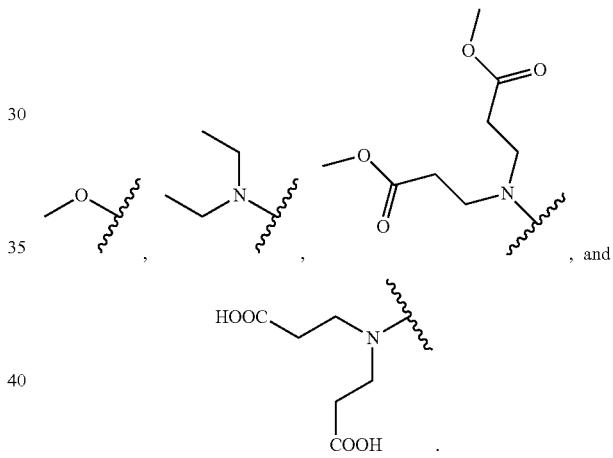

In some embodiments, R$_1$ is selected from:

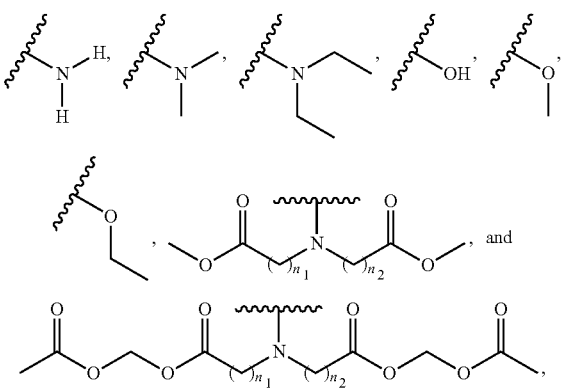

where n$_1$ and n$_2$ are independently 1 or higher than 1. In some embodiments, n$_1$ and n$_2$ are 1 to 5, 1 to 10, 1 to 20, or 1 to 50.

In an embodiment, $R_2$, $R_3$, and $R_4$ are hydrogen, and $R_1$ is selected from:

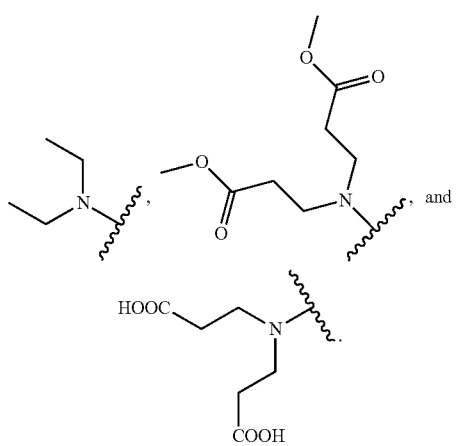

In another embodiment, $R_2$, $R_3$, and $R_4$ are hydrogen, and $R_1$ is selected from:

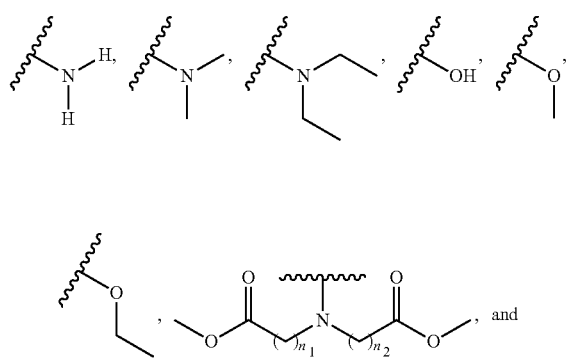

where $n_1$ and $n_2$ are independently 1 or higher than 1. In some embodiments, $n_1$ and $n_2$ are 1 to 5, 1 to 10, 1 to 20, or 1 to 50.

In some embodiments, $R_1$ is an amino substituent, and oxygen substituent, or an ester.

In some embodiments, $R_2$, $R_3$, and $R_4$ are hydrogen, and $R_1$ is selected from:

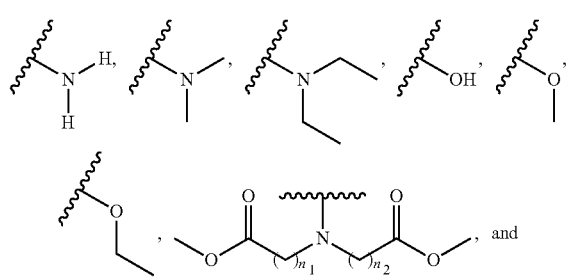

-continued

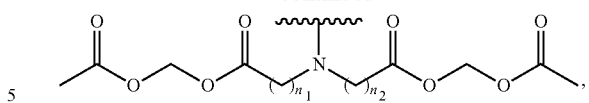

where $n_1$ and $n_2$ are independently 1 or higher than 1. In some embodiments, $n_1$ and $n_2$ are 1 to 5, 1 to 10, 1 to 20, or 1 to 50.

In some embodiments, $R_2$, $R_3$, $R_4$, and $R_5$ are hydrogen; $R_7$ is methyl or methoxy; $R_8$ is hydrogen, methyl or methoxy; and $R_1$ is selected from:

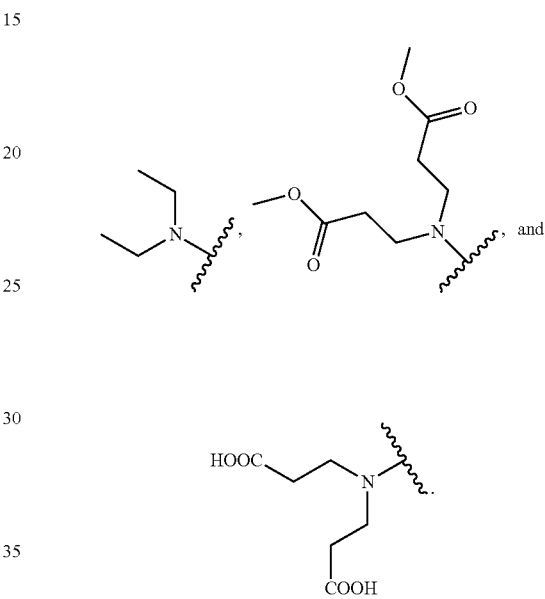

In some embodiments, $R_2$, $R_3$, $R_4$, and $R_5$ are hydrogen; $R_7$ is methyl or methoxy; $R_8$ is hydrogen, methyl or methoxy; and $R_1$ is selected from:

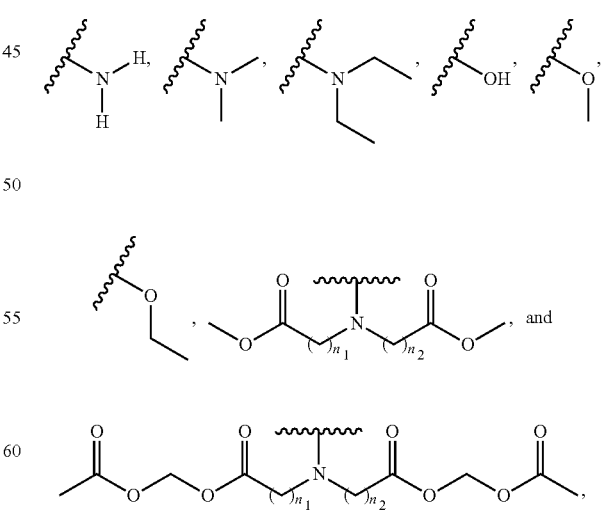

where $n_1$ and $n_2$ are independently 1 or higher than 1. In some embodiments, $n_1$ and $n_2$ are 1 to 5, 1 to 10, 1 to 20, or 1 to 50.

In an embodiment, there is provided a fluorogenic labelling agent of Formula (II), or a salt thereof:

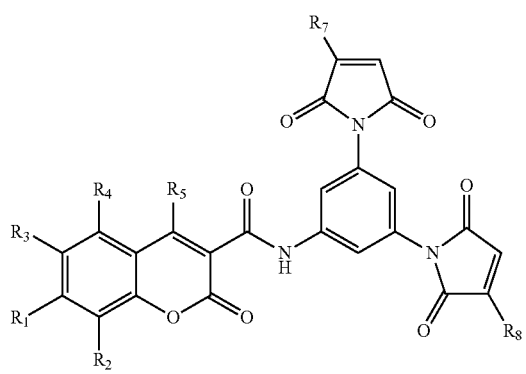

wherein $R_1$ to $R_8$ are as defined above.

In some embodiments of fluorogenic labelling agents of Formula (II), $R_2$, $R_3$, and $R_4$ are hydrogen.

In some embodiments of fluorogenic labelling agents of Formula (II), $R_1$ is selected from:

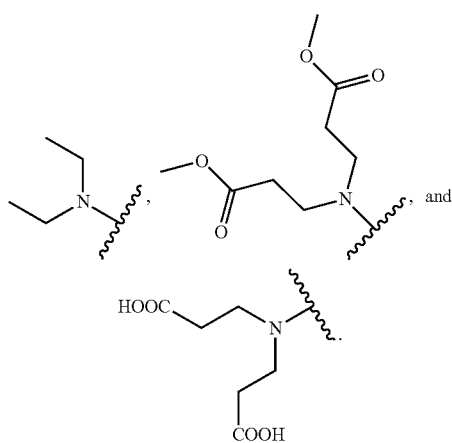

In some embodiments of fluorogenic labelling agents of Formula (II), $R_1$ is selected from:

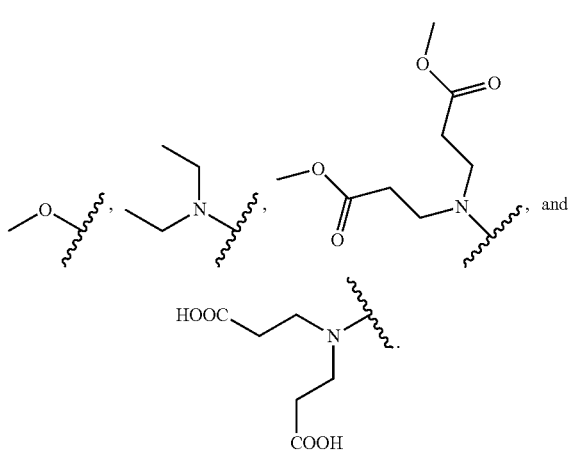

In an embodiment of fluorogenic labelling agents of Formula (II), $R_2$, $R_3$, and $R_4$ are hydrogen, and $R_1$ is selected from:

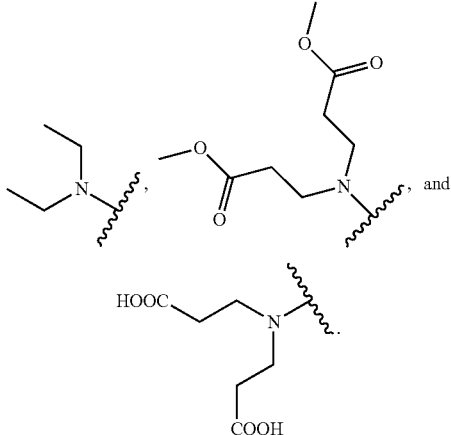

In another embodiment of fluorogenic labelling agents of Formula (II), $R_2$, $R_3$, and $R_4$ are hydrogen, and $R_1$ is selected from:

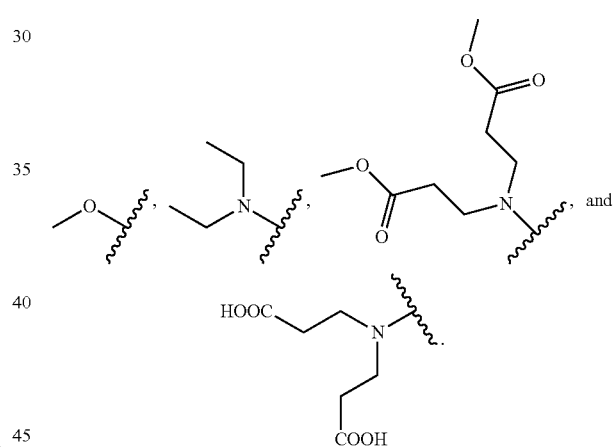

In some embodiments of fluorogenic labelling agents of Formula (II), $R_5$ and $R_6$ are both $X_1$ or $X_2$, or one of $R_5$ and $R_6$ is $X_1$, and the other is $X_2$.

In some embodiments of fluorogenic labelling agents of Formula (II), $R_2$, $R_3$, $R_4$, and $R_5$ are hydrogen; $R_7$ is methyl or methoxy; $R_8$ is hydrogen, methyl or methoxy; and $R_1$ is selected from:

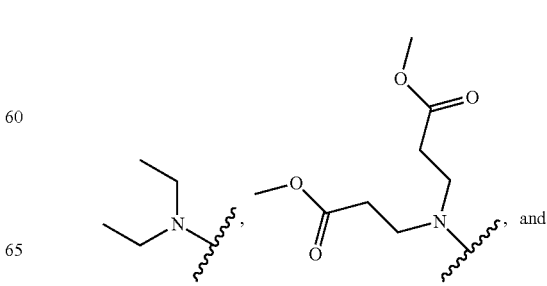

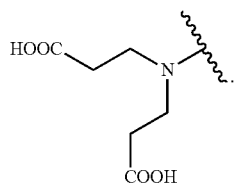

In some embodiments of fluorogenic labelling agents of Formula (II), $R_1$ is an amino substituent, and oxygen substituent, or an ester. In some embodiments of fluorogenic labelling agents of Formula (II), $R_1$ is selected from:

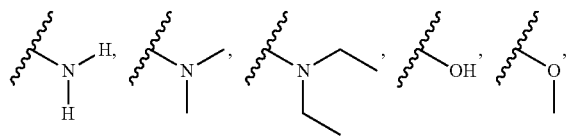

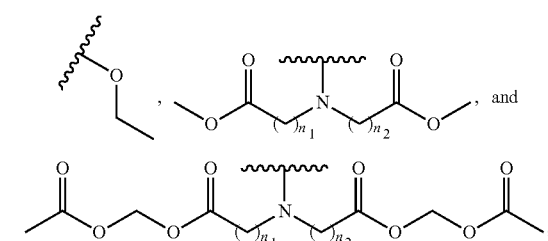

where $n_1$ and $n_2$ are independently 1 or higher than 1. In some embodiments, $n_1$ and $n_2$ are 1 to 5, 1 to 10, 1 to 20, or 1 to 50.

In some embodiments of fluorogenic labelling agents of Formula (II), $R_2$, $R_3$, and $R_4$ are hydrogen, and $R_1$ is selected from:

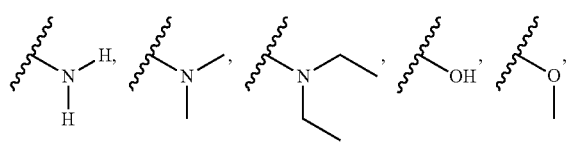

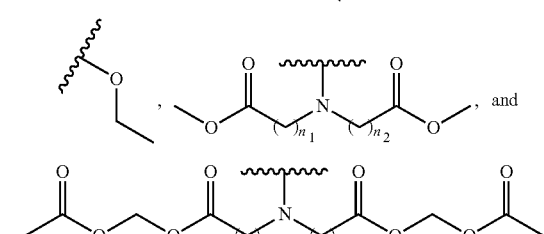

where $n_1$ and $n_2$ are independently 1 or higher than 1. In some embodiments, $n_1$ and $n_2$ are 1 to 5, 1 to 10, 1 to 20, or 1 to 50.

In some embodiments of fluorogenic labelling agents of Formula (II), $R_2$, $R_3$, $R_4$, and $R_5$ are hydrogen; $R_7$ is methyl or methoxy; $R_8$ is hydrogen, methyl or methoxy; and $R_1$ is selected from:

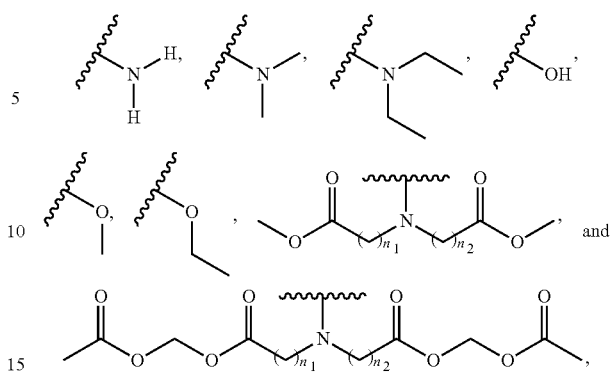

where $n_1$ and $n_2$ are independently 1 or higher than 1. In some embodiments, $n_1$ and $n_2$ are 1 to 5, 1 to 10, 1 to 20, or 1 to 50.

In another embodiment, there is provided a fluorogenic labelling agent of Formula (III), or a salt thereof:

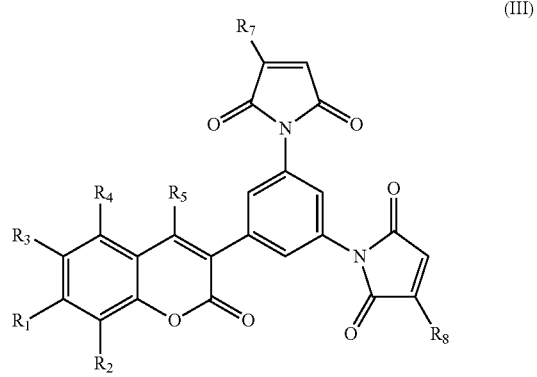

(III)

wherein $R_1$ to $R_8$ are as defined above.

In some embodiments of fluorogenic labelling agents of Formula (III), $R_2$, $R_3$, and $R_4$ are hydrogen.

In some embodiments of fluorogenic labelling agents of Formula (III), $R_1$ is selected from:

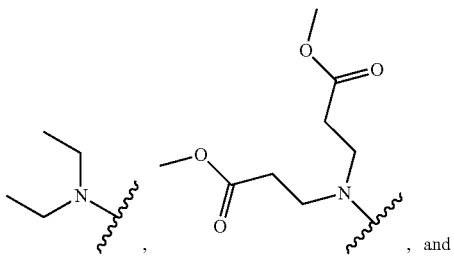

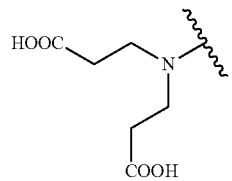

In some embodiments of fluorogenic labelling agents of Formula (III), $R_1$ is selected from:

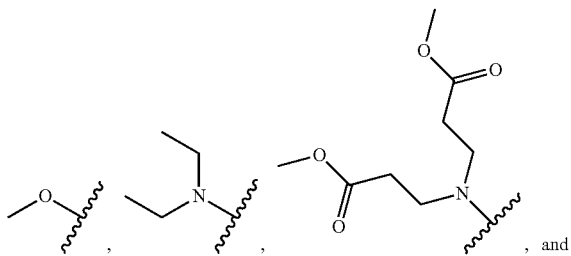
, and

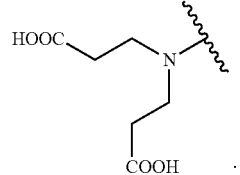
.

In an embodiment of fluorogenic labelling agents of Formula (III), $R_2$, $R_3$, and $R_4$ are hydrogen, and $R_1$ is selected from:

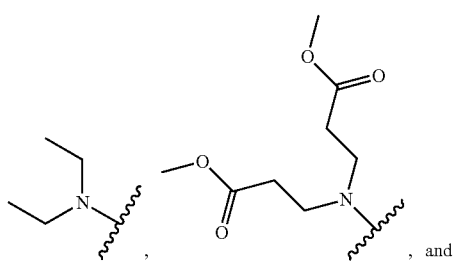
, and

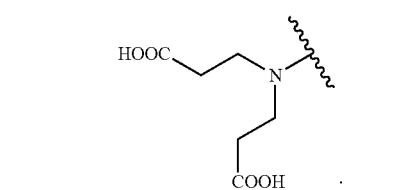
.

In another embodiment of fluorogenic labelling agents of Formula (III), $R_2$, $R_3$, and $R_4$ are hydrogen, and $R_1$ is selected from:

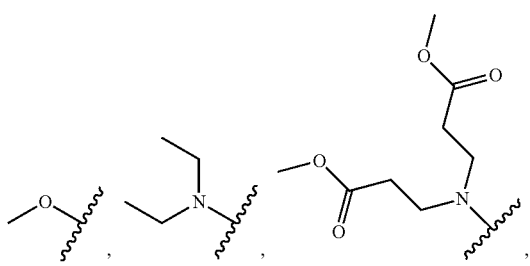
, and

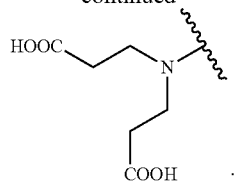
.

In some embodiments of fluorogenic labelling agents of Formula (III), $R_1$ is an amino substituent, and oxygen substituent, or an ester. In some embodiments of fluorogenic labelling agents of Formula (II), $R_1$ is selected from:

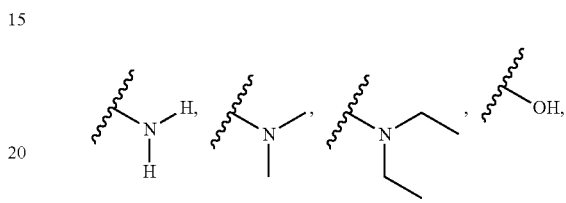

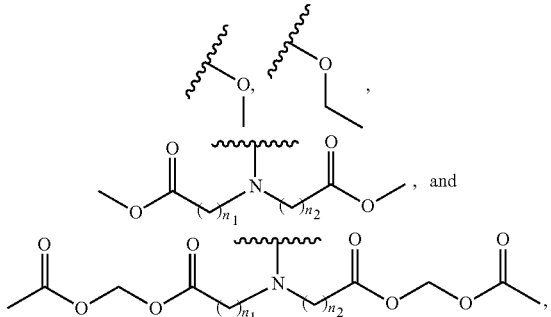

where $n_1$ and $n_2$ are independently 1 or higher than 1. In some embodiments, $n_1$ and $n_2$ are 1 to 5, 1 to 10, 1 to 20, or 1 to 50.

In some embodiments of fluorogenic labelling agents of Formula (III), $R_2$, $R_3$, and $R_4$ are hydrogen, and $R_1$ is selected from:

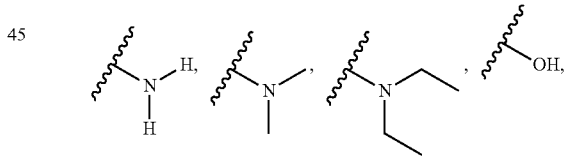

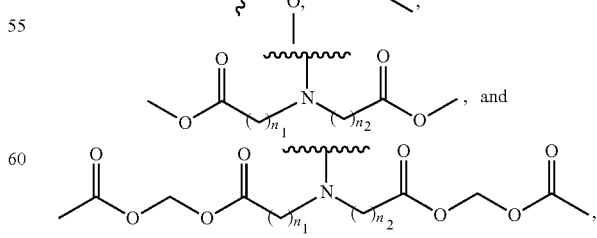

where $n_1$ and $n_2$ are independently 1 or higher than 1. In some embodiments, $n_1$ and $n_2$ are 1 to 5, 1 to 10, 1 to 20, or 1 to 50.

In some embodiments of fluorogenic labelling agents of Formula (III), $R_5$ and $R_6$ are both $X_1$ or $X_2$, or one of $R_5$ and $R_6$ is $X_1$, and the other is $X_2$.

In some embodiments of fluorogenic labelling agents of Formula (III), $R_2$, $R_3$, $R_4$, and $R_5$ are hydrogen; $R_7$ is methyl or methoxy; $R_8$ is hydrogen, methyl or methoxy; and $R_1$ is selected from:

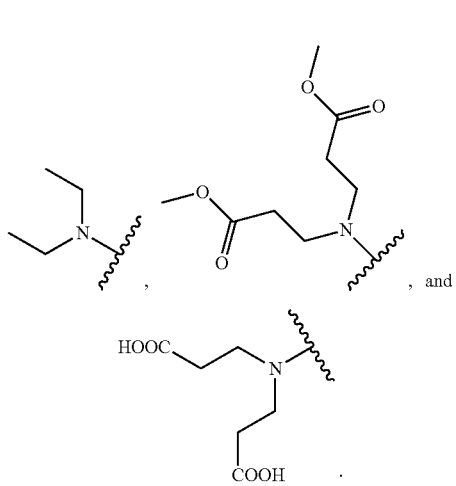

In some embodiments of fluorogenic labelling agents of Formula (III), $R_2$, $R_3$, $R_4$, and $R_5$ are hydrogen; $R_7$ is methyl or methoxy; $R_8$ is hydrogen, methyl or methoxy; and $R_1$ is selected from:

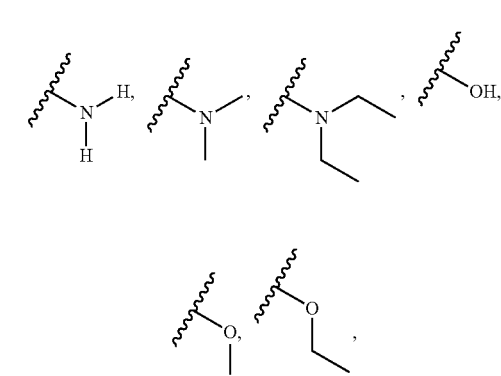

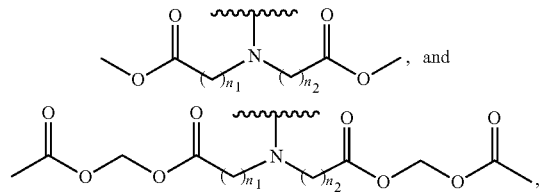

where $n_1$ and $n_2$ are independently 1 or higher than 1. In some embodiments, $n_1$ and $n_2$ are 1 to 5, 1 to 10, 1 to 20, or 1 to 50.

In an embodiment, there is provided a fluorogenic labelling agent which is at least one of the compounds shown in Scheme 1, or a salt thereof:

Scheme 1

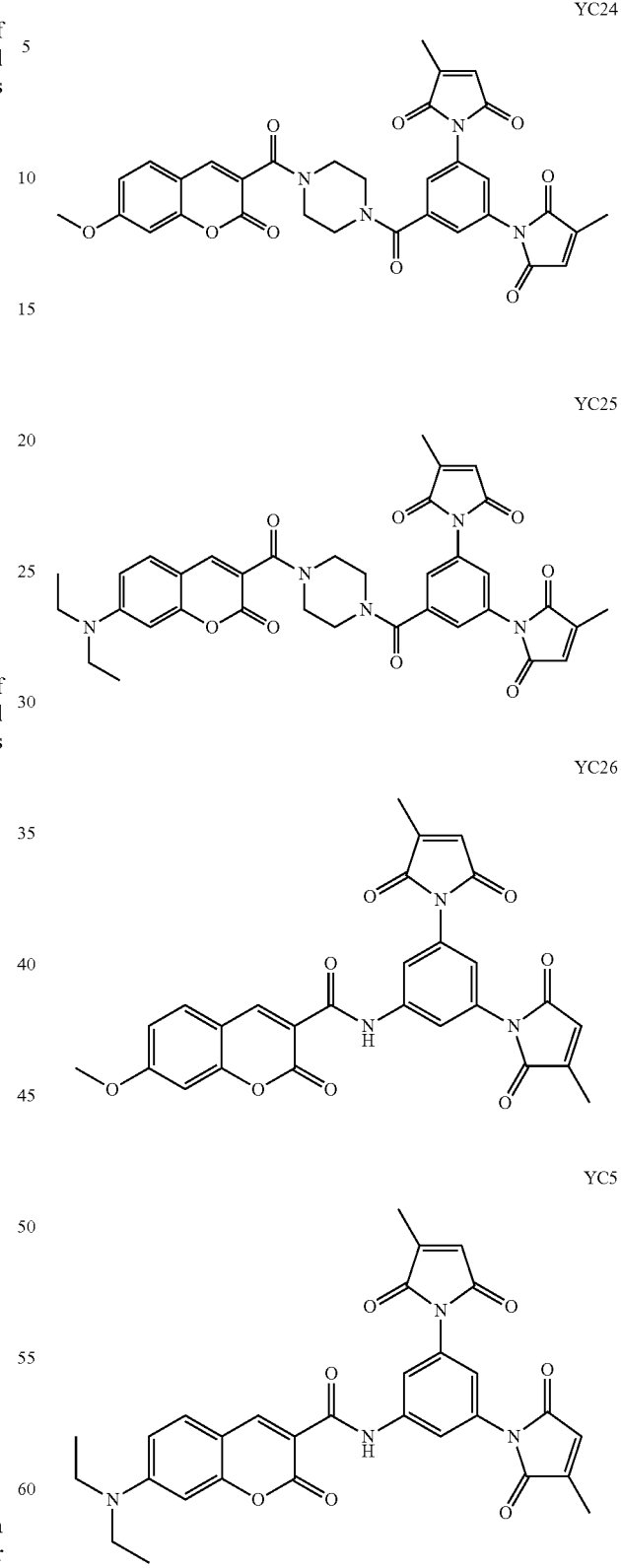

In another embodiment, there is provided a fluorogenic labelling agent comprising the compound shown in Scheme 4, or a salt thereof:

Scheme 4

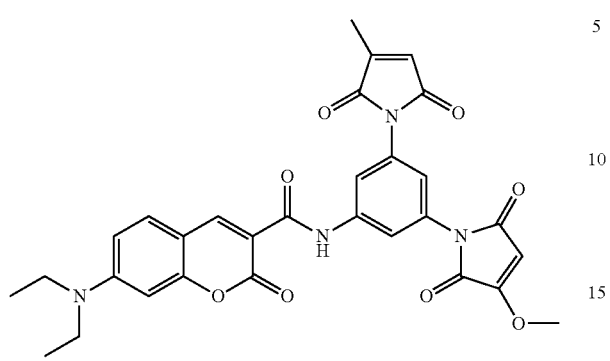

YC9

In another embodiment, there is provided a fluorogenic labelling agent comprising the compound shown in Scheme 5, or a salt thereof:

Scheme 5

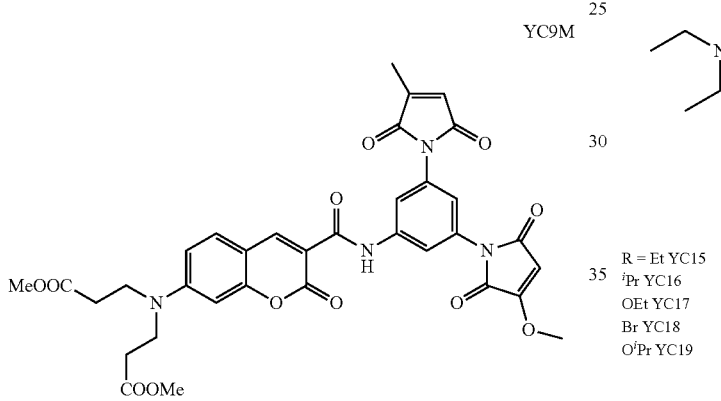

YC9M

In another embodiment, there is provided a fluorogenic labelling agent comprising the compound shown in Scheme 6, or a salt thereof:

Scheme 6

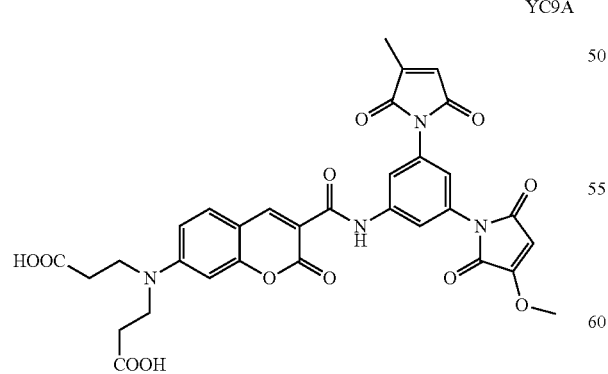

YC9A

It is noted that compound YC9A is the presumed intracellular form of compound YC9M. Without wishing to be bound by theory, it is expected that the methyl esters may be hydrolyzed by esterases within a cell, and that the resulting YC9A compound, which contains at least one negative charge at physiological pH, may be retained inside the cell.

In another embodiment, there is provided a fluorogenic labelling agent which is at least one of the compounds shown in Scheme 8, or a salt thereof:

Scheme 8

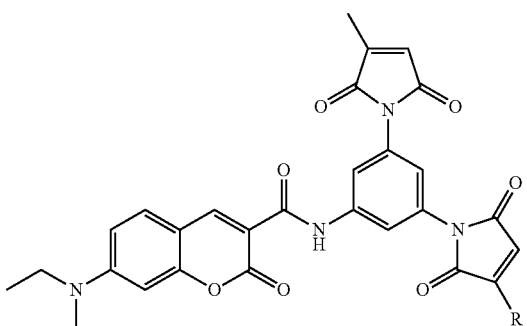

YC15-YC19

R = Et YC15
$^i$Pr YC16
OEt YC17
Br YC18
O$^i$Pr YC19

In another embodiment, there is provided a fluorogenic labelling agent of which is at least one of the compounds shown in Scheme 11, or a salt thereof:

Scheme 11

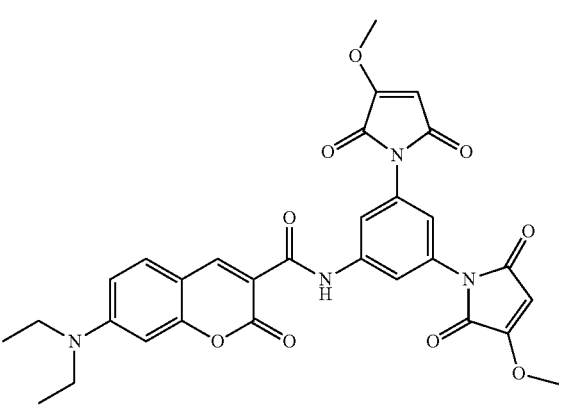

YC20

YC21M

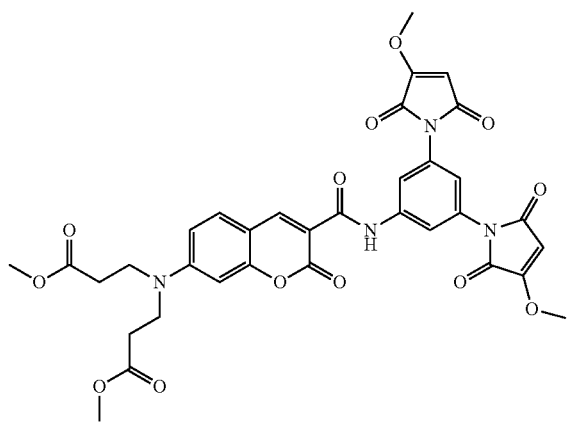

In another embodiment, there is provided a fluorogenic labelling agent comprising the compound shown in Scheme 14, or a salt thereof:

Scheme 14

YC21A

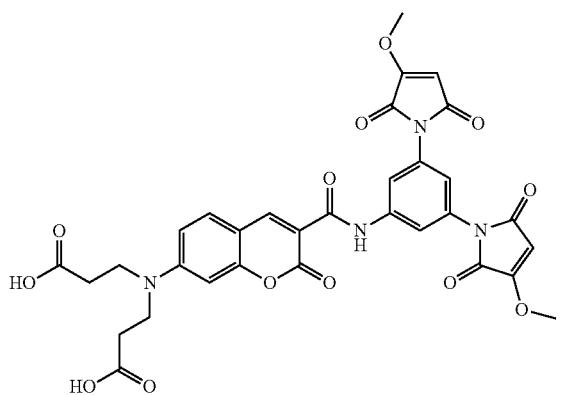

It is noted that compound YC21A is the presumed intracellular form of compound YC21M. Without wishing to be bound by theory, it is expected that the methyl esters may be hydrolyzed by esterases within a cell, and that the resulting YC21A compound, which contains at least one negative charge at physiological pH, may be retained inside the cell.

In another broad aspect, there are provided herein methods of labelling and/or detecting specific protein targets, using fluorogenic compounds provided herein. In one embodiment, methods for labelling and/or detecting a target protein are provided, comprising contacting the target protein with a fluorescent labelling agent of the invention, under conditions where the fluorescent labelling agent reacts with sterically unhindered sulfhydryl groups on the target protein, and detecting a fluorescent signal from the fluorescent labelling agent, wherein the fluorescence of the fluorescent labelling agent is quenched in the absence of reaction with the target protein, and detection of the fluorescent signal indicates that reaction of the fluorescent labelling agent with the target protein has occurred. In some embodiments, the fluorescence of the fluorescent labelling agent is quenched before reaction with a target protein, such that fluorescence is only detected after the fluorescent labelling agent has reacted with the target protein, so that detection of fluorescence indicates that reaction has occurred and indicates presence of the target protein. In some embodiments, some fluorescence may be detected before the fluorescent labelling agent has reacted with the target protein (e.g., before labelling), and fluorescence increases after the fluorescent labelling agent has reacted with the target protein, such that an increase in fluorescence indicates that reaction has occurred, thereby indicating presence of the target protein.

Fluorescent labelling agents may be used to label and/or detect specific protein targets in vitro, in vivo, or ex vivo. In some embodiments, fluorescent labelling agents are used in living cells for "live imaging," allowing visualization of a target protein's expression, localization, trafficking, and/or interactions inside a cell, or inside a living organism. Fluorescent labelling agents and methods of use thereof may therefore provide valuable information about the function of target proteins that cannot be uncovered in vitro. Thus in some embodiments, reaction of a fluorescent labelling agent and a target protein occurs in a living cell. A living cell may be a cultured cell, of which many types are known (e.g., a primary culture, a cell line, a transformed cell line, etc.). A living cell may be present in an organism, such as a transgenic animal, etc.

In some embodiments, a cell, e.g., a living cell, is an animal cell. Non-limiting examples of animal cells include mammalian cells, invertebrate cells, vertebrate cells, human cells, rodent cells, mouse cells, rat cells, insect cells, nematode cells, and fish cells.

In some embodiments, a fluorescent labelling agent is not toxic to cells, e.g., is not toxic to animal cells.

In some embodiments of methods provided herein, a target protein is an intracellular protein. In some embodiments, a target protein is an extracellular or cell-surface protein. It will be understood that a fluorescent labelling agent may react with, or label, a target protein intracellularly or extracellularly, depending on where the target protein is localized. In some embodiments, characteristics of the fluorescent labelling agent are sufficient to allow intracellular labelling. For example, the fluorescent labelling agent may have one or more of the following characteristics: selectivity/high specificity for the target protein; lack of background reactivity (e.g., lack of reaction with cellular proteins or glutathione); and efficient quenching of fluorescence before reaction with the target protein, coupled with bright fluorescence after reaction with the target protein. In the context of background reactivity, "lack of reaction with cellular proteins" is meant to refer to lack of reaction with native cellular proteins that are not linked, e.g., genetically fused, to a short peptide sequence or tag having two sterically unhindered sulfhydryl groups, e.g., Cys residues, separated by a corresponding distance.

In some embodiments, a target protein comprises a short peptide sequence having two sterically unhindered sulfhydryl groups, e.g., two Cysteine (Cys) residues, separated by an appropriate distance for reaction with a fluorescent labelling agent of the invention. In one embodiment, the distance between the two sulfhydryl groups or Cys residues is about 10 Å. In an embodiment, a target protein comprises a dC10α tag. It should be understood that other tags may be used, as long as a tag includes two sulfhydryl groups separated by a corresponding distance, and reacts efficiently and appropriately to a fluorescent labelling agent, such that quenching of fluorescence is removed upon binding of the agent.

Generally, in methods provided herein, a target protein has been engineered to include a short peptide sequence or tag having two sterically unhindered sulfhydryl groups, e.g., Cys residues, separated by a corresponding distance. For methods conducted in vitro, for example, such a target protein may be synthesized in vitro or may be purified from a cell genetically engineered to express the target protein comprising the peptide sequence or tag. For methods conducted in vivo or ex vivo, in some embodiments a cell or organism may be genetically engineered to express the target protein comprising the peptide sequence or tag. Many such methods are known in the art.

In some embodiments, agents and methods provided herein are particularly advantageous for live imaging, due to the small size of the peptide sequence or tag linked to the target protein. In some embodiments, the peptide sequence or tag on the target protein does not significantly alter the function or localization of the target protein.

Many methods for detecting fluorescence are known and may be used in methods provided herein. Non-limiting examples of techniques used to detect fluorescence include fluorescence microscopy (e.g., with a fluorescence microscope, a confocal microscope, a total internal reflection fluorescence microscope (TIRFM), etc.); fluorescence spectroscopy (e.g., with a filter fluorometer, a spectrofluorometer, etc.); fluorescence resonance energy transfer (FRET); plate readers (e.g., microplate readers); HPLC fluorescence detectors; and so on. One skilled in the art will select the appropriate method of detecting fluorescence in accordance with the particular application or target protein being studied.

In some embodiments, an agent or method provided herein may be used in conjunction with a second labelling agent to detect a second target protein, for example in a double labelling experiment to allow simultaneous detection or visualization of two different target proteins, or to assay biomolecular interactions between two target proteins. In such experiments, typically the second labelling agent fluoresces at a different wavelength from the first fluorescent labelling agent, so that the two fluorescent signals can be distinguished. For example, there are provided methods for assaying biomolecular interactions between a first target protein and a second target protein, wherein the first target protein and the second target protein are each linked to a peptide having two sterically unhindered sulfhydryl groups separated by an appropriate distance for binding to a first fluorescent labelling agent and a second fluorescent labelling agent, respectively; the first target protein and the second target protein are contacted with the first fluorescent labelling agent and the second fluorescent labelling agent, respectively; and fluorescence of the first fluorescent labelling agent and the second fluorescent labelling agent are detected. The first and second fluorescent labelling agents may comprise two different fluorogens, permitting detection of their interaction through a FRET-based fluorescent assay, for example. It will be appreciated that in addition to protein-protein interactions, other molecular interactions, such as protein-small molecule, protein-nucleic acid and protein-carbohydrate interactions, may be detected using similar methods.

In another broad aspect of the invention, there are provided kits for labelling and/or detecting a target protein comprising a fluorescent labelling agent of the invention and instructions for use thereof. A kit may also include reagents, solvents, buffers, etc., required for carrying out the methods described herein. In some embodiments, a kit includes a peptide comprising a dC10α tag. In some embodiments, a kit includes a vector encoding a dC10α tag suitable for use in cloning or expressing a protein of interest comprising the dC10α tag. Kits for live imaging of target proteins and for assaying biomolecular interactions are also provided.

Synthesis of Fluorogens

An overview of compound synthesis is given here. More detailed protocols for synthesis of compounds described herein are given in the Examples below.

Synthesis of YC5, YC24-YC26

The synthesis of YC24-YC25 is shown in Scheme 2. 7-Diethylaminocoumarin-3-carboxylic acid (1) or 7-methoxycoumarin-3-carboxylic acid (2), tert-butyl piperazine-1-carboxylate and 3,5-bis(3-methyl-2,5-dioxo-2,5-dihydro-1H-pyrrol-1-yl)benzoic acid (8) were synthesized according to literature reports (Keillor, J. W. et al., Org Biomol Chem 2011, 9, 185-197; Ma, Y. M. et al., J Med Chem 2004, 47, 6349-6362; Fixon-Owoo, S. et al., Phytochemistry 2003, 63, 315-334). Coumarin compounds 1 or 2 reacted with tert-butyl piperazine-1-carboxylate 3 with the assistance of coupling reagents HOBt and EDC.HCl to form compounds 4 or 5. After removal of the Boc group with TFA, product 6 or 7 underwent another amide coupling reaction with dimaleimide compound 8 to form fluorogen YC24 or YC25.

For the synthesis shown in Scheme 2, reagents and conditions were as follows: (a) malonic acid, aniline, pyridine, rt, overnight, 42%; (b) 2,2-dimethyl-1,3-dioxane-4,6-dione, piperidine, AcOH, reflux, 85%; (c) compound 3, HOBt, EDC.HCl, DMF, r.t., overnight, 90%-100%; (d) TFA, CH$_2$Cl$_2$, 100%; (e) compound 8, HOBt, EDC.HCl, DMF, r.t., overnight, 9%-22%.

Scheme 2

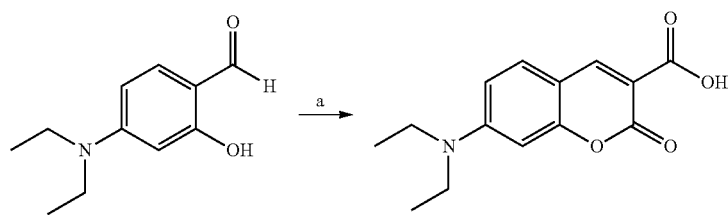

1

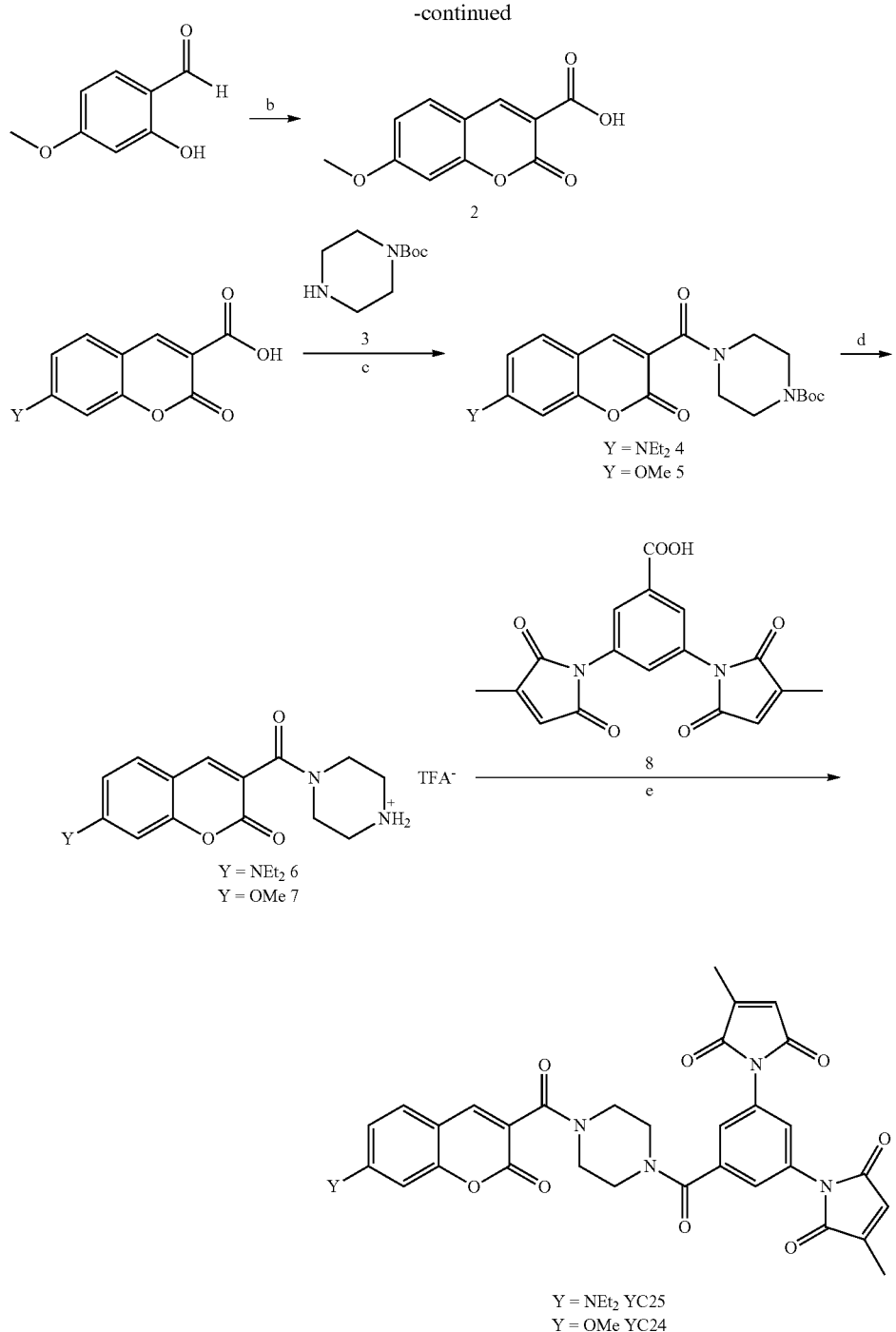

The synthesis of YC5 and YC26 is shown in Scheme 3. Synthesis of 3,5-dinitroaniline (9) followed the procedure developed in our group (Keillor, J. W. et al., Org Biomol Chem 2011, 9, 185-197) and then the amino group was Boc protected over two steps. Then the two nitro groups were reduced by palladium-catalyzed hydrogenation, followed by a two-step maleimide addition with good yield in the presence of $ZnCl_2$ and HMDS (Keillor, J. W. et al., Org Biomol Chem 2011, 9, 185-197). The Boc protecting group was removed with TFA to give free amine, which was then reacted with coumarin derivatives to obtain fluorogens YC5 and YC26.

For the synthesis shown in Scheme 3, reagents and conditions were as follows: (f) $NaN_3$, $H_2SO_4$ (fuming), 12 M $H_2SO_4$, $CHCl_3$, reflux, 3 h, 54%; (g) (1) $Boc_2O$, $Et_3N$, DMAP, THF, reflux, 1 h, (2) $K_2CO_3$, MeOH, 65° C., 5 h, 92% (two steps); (h) $H_2$, Pd/C, THF/MeOH, r.t., 3 h, 100% (i) (1) citraconic anhydride, acetone, 25° C., 2 h, (2) HMDS, $ZnCl_2$, Tol/DMF, 135° C., 4 h, 70%; (j) TFA, $CH_2Cl_2$, r.t., 2 h, 88%; (k) coumarin compound 1 or 2, TBTU, DIPEA, DMF, r.t., 12 h, 14%-50%.

Scheme 3

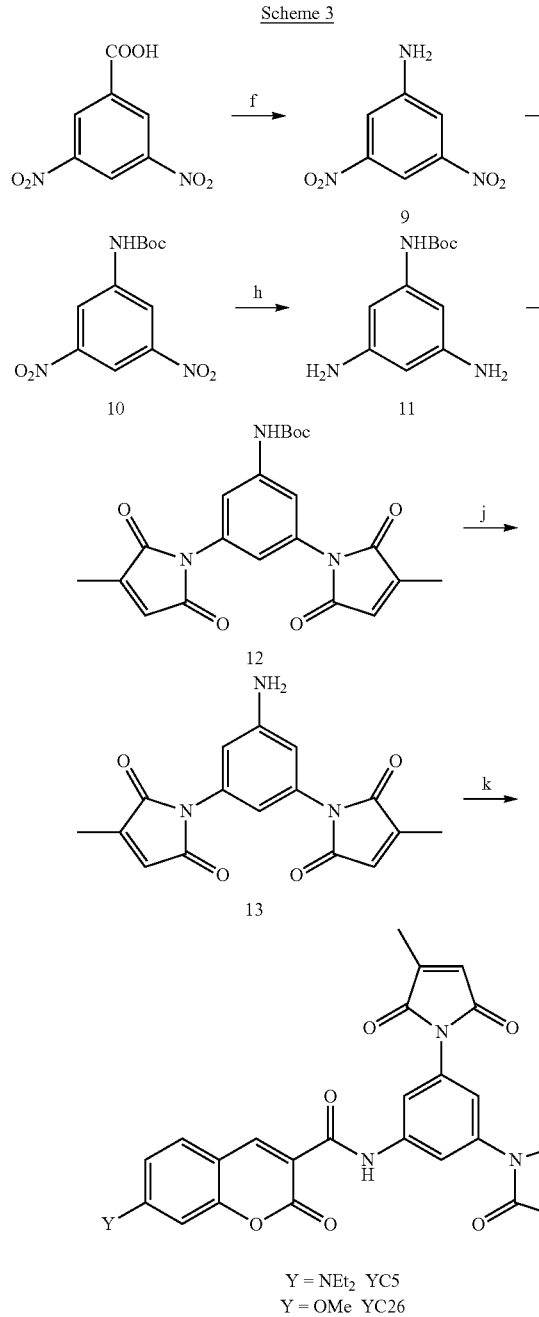

ange, C. et al., Chem Commun 2008, 1217-1219). At the end, the coumarin derivative (21) and the dimaleimide moiety (18) were coupled using the same method as described for the synthesis of YC9 below.

For the synthesis shown in Scheme 3, reagents and conditions were as follows: (a) $NaN_3$, $H_2SO_4$ (fuming), 12 M $H_2SO_4$, $CHCl_3$, reflux, 3 h, 54%; (b) (1) $Boc_2O$, $Et_3N$, DMAP, THF, reflux, 1 h, (2) $K_2CO_3$, MeOH, 65° C., 5 h, 92% (two steps); (c) Pd/C, $Et_3N$, HCOOH, ACN, reflux, 10 min, 91% yield; (d) (1) citraconic anhydride, $CHCl_3$, r.t., 3 h, (2) HMDS, $ZnCl_2$, Tol/DMF, 135° C., 2 h, 82% (two steps); (e) $SnCl_2$, EtOH, 70° C., 1 h, 80%; (f) (1) methoxymaleimide, $CHCl_3$, r.t., 3 h; (2) HMDS, $ZnCl_2$, Tol/DMF, 135° C., 2 h, 100% (two steps); (g) TFA, $CH_2Cl_2$, 2 h, 99%; (h) acrylic acid, $H_2O$, 70° C.; $H_2SO_4$, methanol, 67%; (b) $POCl_3$, DMF, 0° C. to rt, 40° C. to rt; $H_2O$, 50° C., 47%; (c) malonic acid, aniline, pyridine, rt, 56%; (f) (1) $POCl_3$, DCE, 94° C., 4 h; (2) 7-(bis(3-methoxy-3-oxopropyl)amino) coumarin-3-carboxylic acid (3), acetonitrile, r.t., overnight, 56% (two steps)

Scheme 7

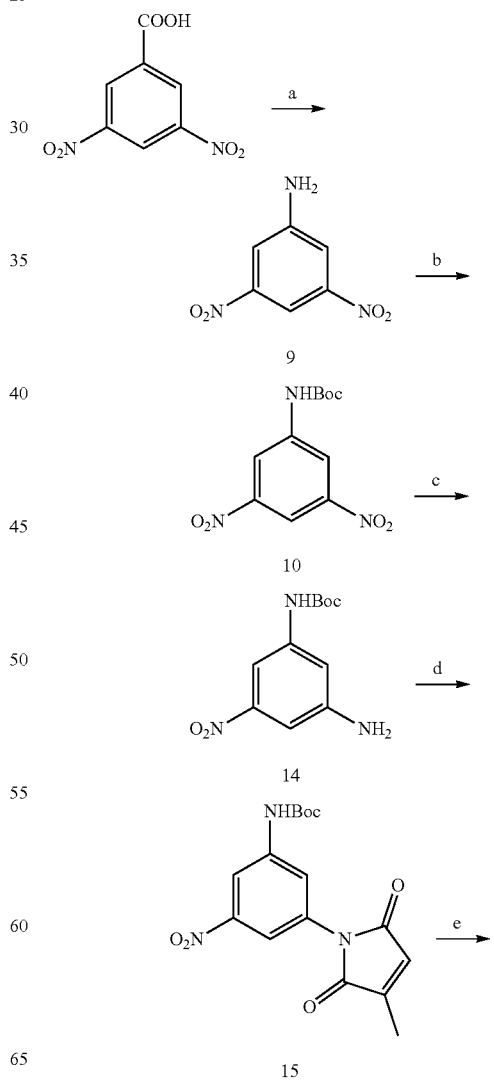

Synthesis of YC9M

The synthesis of YC9M is shown in Scheme 7. Methoxymaleic anhydride was synthesized according to a literature procedure (Sahoo, M. K. et al., Synthesis-Stuttgart 2003, 346-349). The synthesis of the dimaleimide moiety (18) was the same as described for YC9 below. The synthesis of modified coumarin 21 started with 3-aminophenol. 3-Aminophenol underwent a facile Michael addition with acrylic acid to give a diacid product (Jose, J. et al., J Org Chem 2006, 71, 7835-7839), which was followed by an acid-catalyzed methylation. Ortho-formylation of the phenol gave compound 20. The 7-(bis(3-methoxy-3-oxopropyl) amino)-2-oxo-2H-chromene-3-carboxylic acid (21) skeleton was constructed using a base catalyzed aldol reaction (Or-

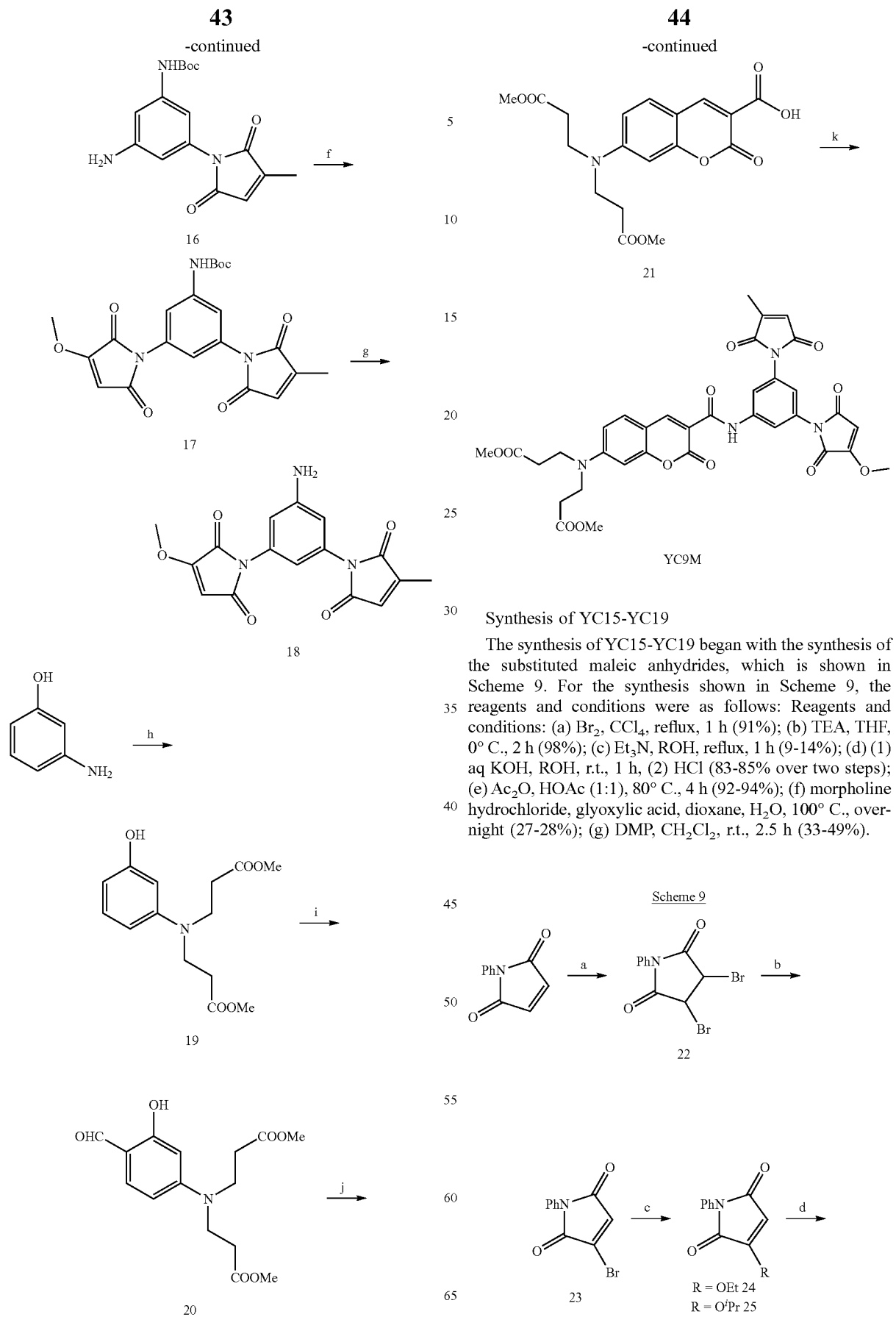

Synthesis of YC15-YC19

The synthesis of YC15-YC19 began with the synthesis of the substituted maleic anhydrides, which is shown in Scheme 9. For the synthesis shown in Scheme 9, the reagents and conditions were as follows: Reagents and conditions: (a) Br$_2$, CCl$_4$, reflux, 1 h (91%); (b) TEA, THF, 0° C., 2 h (98%); (c) Et$_3$N, ROH, reflux, 1 h (9-14%); (d) (1) aq KOH, ROH, r.t., 1 h, (2) HCl (83-85% over two steps); (e) Ac$_2$O, HOAc (1:1), 80° C., 4 h (92-94%); (f) morpholine hydrochloride, glyoxylic acid, dioxane, H$_2$O, 100° C., overnight (27-28%); (g) DMP, CH$_2$Cl$_2$, r.t., 2.5 h (33-49%).

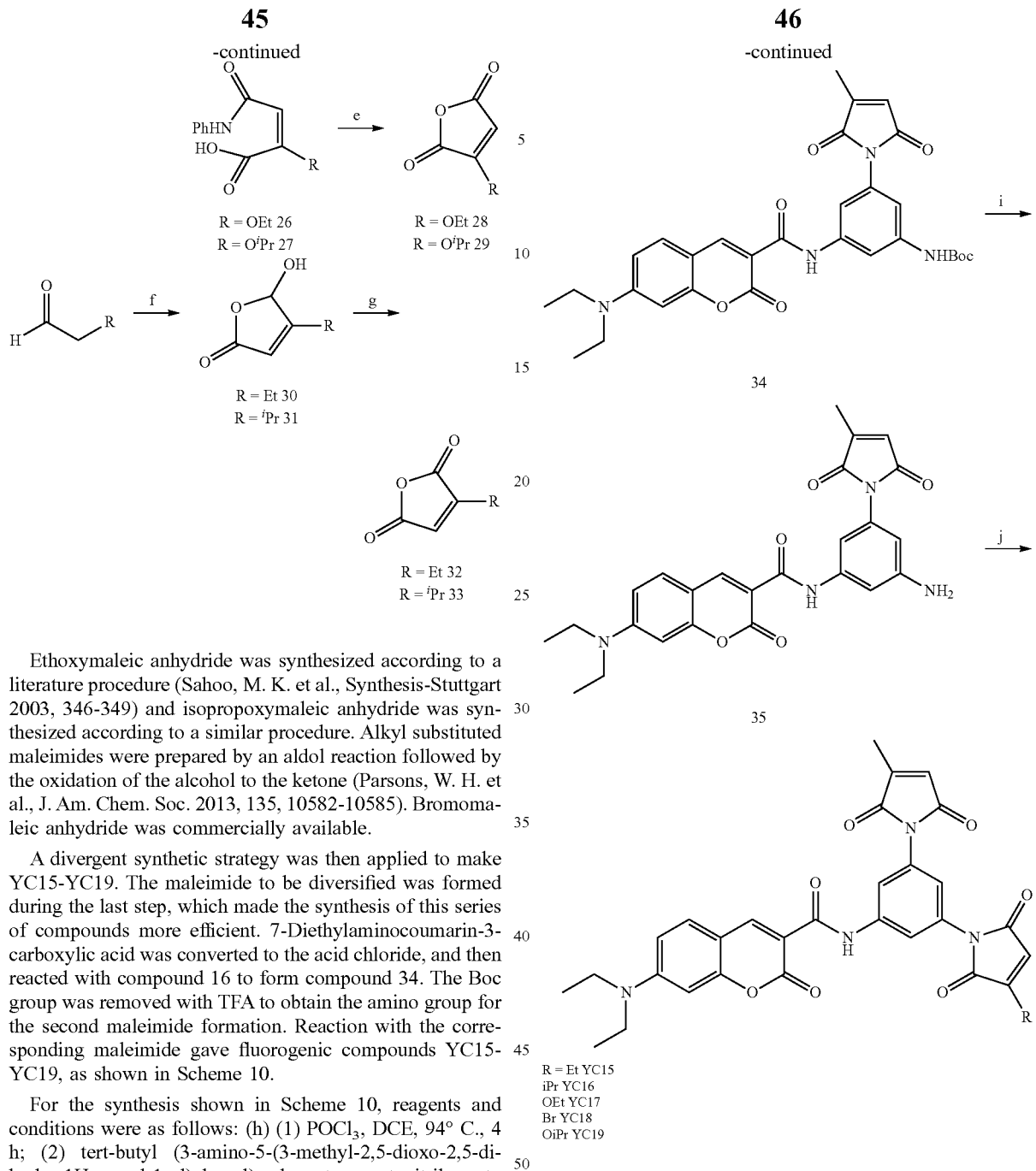

Ethoxymaleic anhydride was synthesized according to a literature procedure (Sahoo, M. K. et al., Synthesis-Stuttgart 2003, 346-349) and isopropoxymaleic anhydride was synthesized according to a similar procedure. Alkyl substituted maleimides were prepared by an aldol reaction followed by the oxidation of the alcohol to the ketone (Parsons, W. H. et al., J. Am. Chem. Soc. 2013, 135, 10582-10585). Bromomaleic anhydride was commercially available.

A divergent synthetic strategy was then applied to make YC15-YC19. The maleimide to be diversified was formed during the last step, which made the synthesis of this series of compounds more efficient. 7-Diethylaminocoumarin-3-carboxylic acid was converted to the acid chloride, and then reacted with compound 16 to form compound 34. The Boc group was removed with TFA to obtain the amino group for the second maleimide formation. Reaction with the corresponding maleimide gave fluorogenic compounds YC15-YC19, as shown in Scheme 10.

For the synthesis shown in Scheme 10, reagents and conditions were as follows: (h) (1) POCl$_3$, DCE, 94° C., 4 h; (2) tert-butyl (3-amino-5-(3-methyl-2,5-dioxo-2,5-dihydro-1H-pyrrol-1-yl)phenyl)carbamate, acetonitrile, r.t., overnight (82% over two steps); (i) TFA, CH$_2$Cl$_2$, r.t., 3 h (95%); (j) (1) maleic anhydride, acetone, r.t., 4 h; (2) ZnCl$_2$, HMDS, DMF/Toluene, 135° C. (35-62% over two steps).

Scheme 10

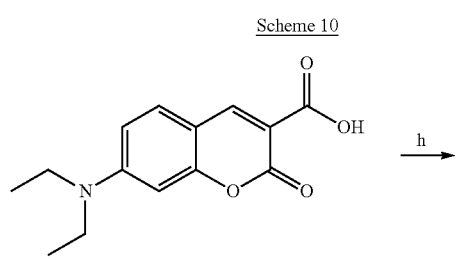

Synthesis of YC20 and YC21M

The synthesis of YC20 is shown in Scheme 12. The synthesis of YC20 began with compound 11 as described in the previous sections. Compound 11 can react with methoxymaleic anhydride to obtain compound 36. After removal of the Boc group, compound 37 was then coupled with either 7-diethylaminocoumarin-3-carboxylic acid or compound 10 to form YC20 or YC21M.

For the synthesis shown in Scheme 12, the reagents and conditions were as follows: (a) (1) 3-methoxyfuran-2,5-dione, CHCl$_3$, r.t., 3 h, (2) HMDS, ZnCl$_2$, Tol/DMF, 135° C., 3 h (31% over two steps); (b) TFA/DCM, r.t., 2 h (48%); (c) (1) POCl$_3$, DCE, 94° C., 4 h; (2) tert-butyl (3-amino-5-(3-methyl-2,5-dioxo-2,5-dihydro-1H-pyrrol-1-yl)phenyl)carbamate, pyridine, r.t., overnight (38%-55% over two steps).

Scheme 12
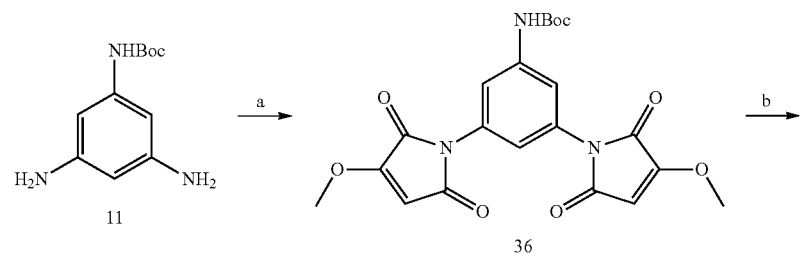
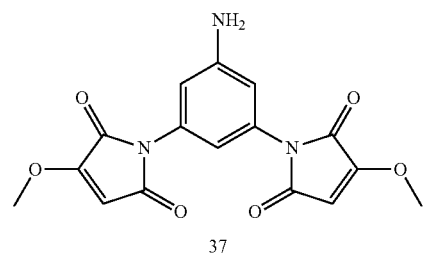
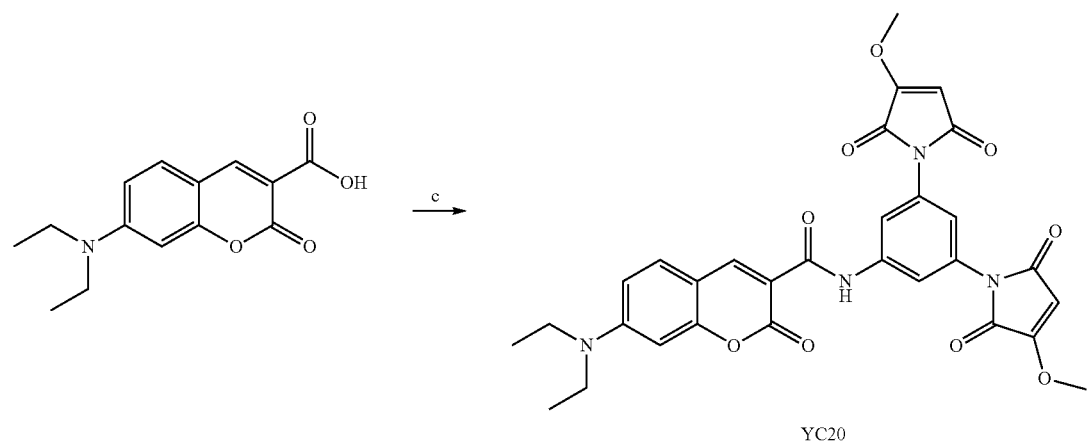
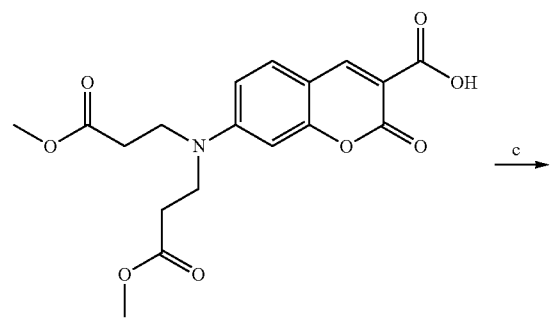

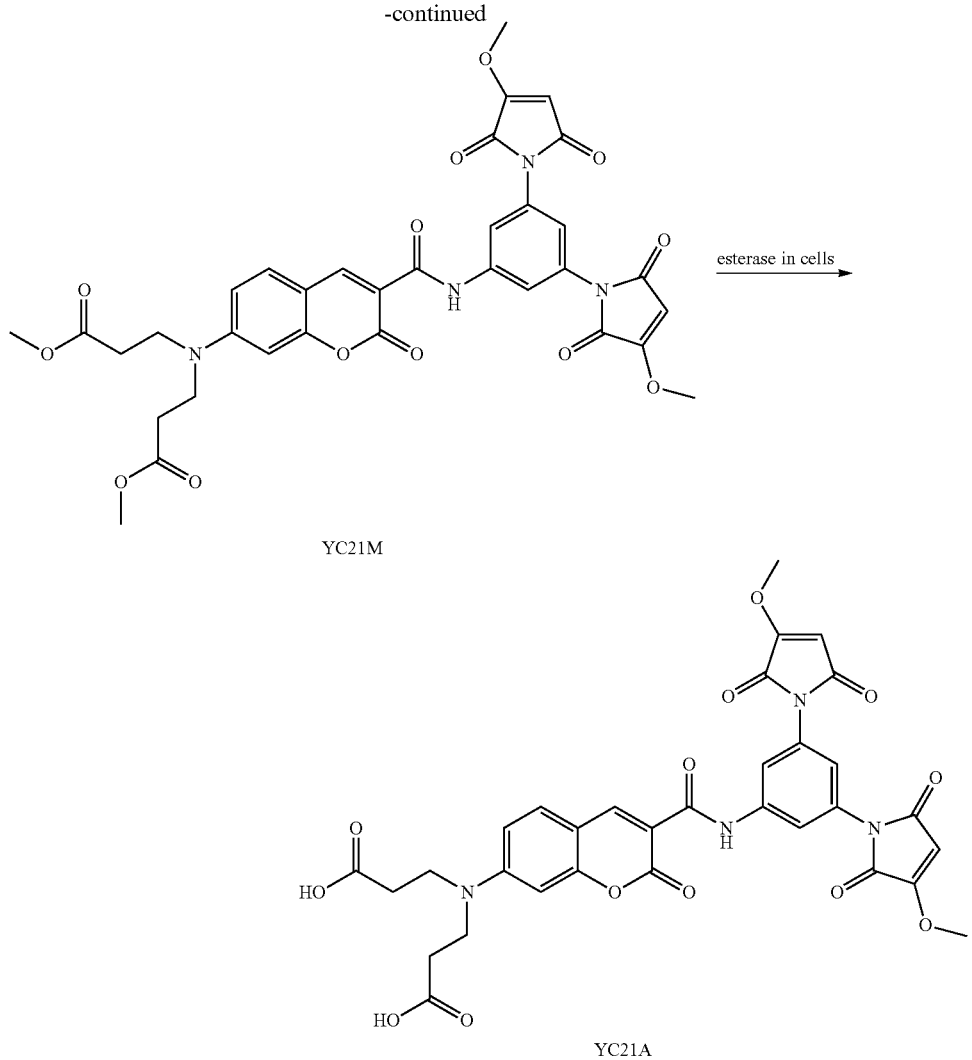

YC21M

YC21A

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention. A list of abbreviations used herein is given in Table 4.

Photophysical Properties of YC5, YC24-YC26 Before and after Protein Labelling

For experiments described herein, maltose-binding protein (MBP) was chosen as a highly-soluble test protein and the dC10α tag was fused to its C-terminus (MBP-dC10α) as described previously (Guy, J. et al., Mol. Biosyst. 2010, 6, 976-987).

The fluorescence emission spectra of fluorogens YC5, YC24-YC25 before and after labelling with model target protein MBP-dC10α are shown in FIG. 1. It is noted that YC26 had poor aqueous solubility, making such photophysical characterization impractical.

For YC24, the fluorescence of the pendant coumarin fluorophore was quenched very efficiently by the dimaleimide unit, but the fluorescence after the labelling reaction was also weak, which is not ideal for a fluorogenic probe. On the other hand, the quenching of fluorescence of the coumarin fluorophore was not strong for YC25, meaning the fluorogenic reagent had strong background fluorescence. Thus, YC25 is also not ideal as a "turn-on" fluorogenic labelling reagent. Only YC5 satisfied both criteria for a "turn-on" fluorogen: its intrinsic fluorescence was negligible, meaning it would present low background fluorescence, but it showed strong fluorescence after the labelling reaction, meaning it would allow sensitive detection. Thus, the combination of 7-diethylaminocoumarin-3-carboxylic acid and its direct amide linkage to the reactive aryl dimaleimide moiety was retained for the design of successive fluorogens.

Selectivity of YC9 and Comparison with YC5

The asymmetric labelling agent YC9 and the symmetric analogue YC5 were tested using the MBP-dC10α test protein. Both YC5 and YC9 were found to exhibit negligible background fluorescence, indicating that their dimaleimide moieties were both capable of quenching coumarin fluorescence highly effectively, regardless of the substituents on the pendant maleimide groups. Furthermore, both fluorogenic reagents became strongly fluorescent after reaction with the test protein MBP-dC10α, showing acceptable fluorescence enhancement (FE) ratios of 69 for YC5 and 62 for YC9.

Kinetic studies were then performed for the thiol addition reactions of YC5 and YC9 with 3-mercaptopropionic acid (MPA) as a water-soluble, nucleophilic model thiol (Scheme 13). Reactions were run in the presence of a large excess of MPA, making them pseudo-first order in fluorogen. The resulting time-dependent increase in fluorescence was fit to a model for consecutive first order reactions, providing pseudo-first order rate constants for both addition steps. The concentration of MPA was then varied, allowing second order rate constants to be calculated for both steps. As shown in Table 2, for YC5 the first thiol addition was 7 times faster than the second addition, possibly due to a steric effect; however, for YC9 the second addition was 63 times slower than the first. This confirmed our assumption that for an asymmetric dimaleimide moiety with a less reactive maleimide, the second intermolecular thiol addition was significantly slower.

Kinetic studies of reactions of YC5 and YC9 with test thiol MPA are shown in Scheme 13, and Table 2 shows second order rate constants measured for the consecutive thiol addition reactions of MPA with fluorogens YC5 and YC9.

Scheme 13

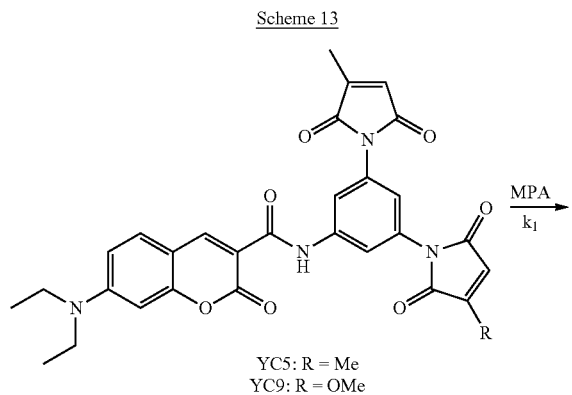

YC5: R = Me
YC9: R = OMe

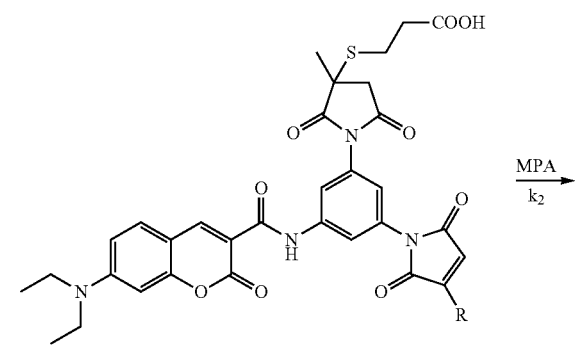

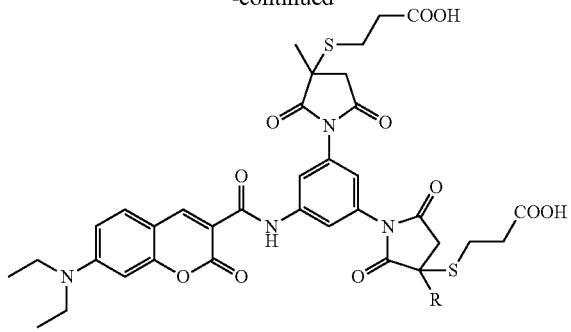

TABLE 2

| Fluorogen | $k_1$ (M$^{-1}$s$^{-1}$) | $k_2$ (M$^{-1}$s$^{-1}$) |
|---|---|---|
| YC5 | 1.208 ± 0.249 | 0.1571 ± 0.0510 |
| YC9 | 2.480 ± 0.216 | 0.0388 ± 0.0133 |

Figure 10:
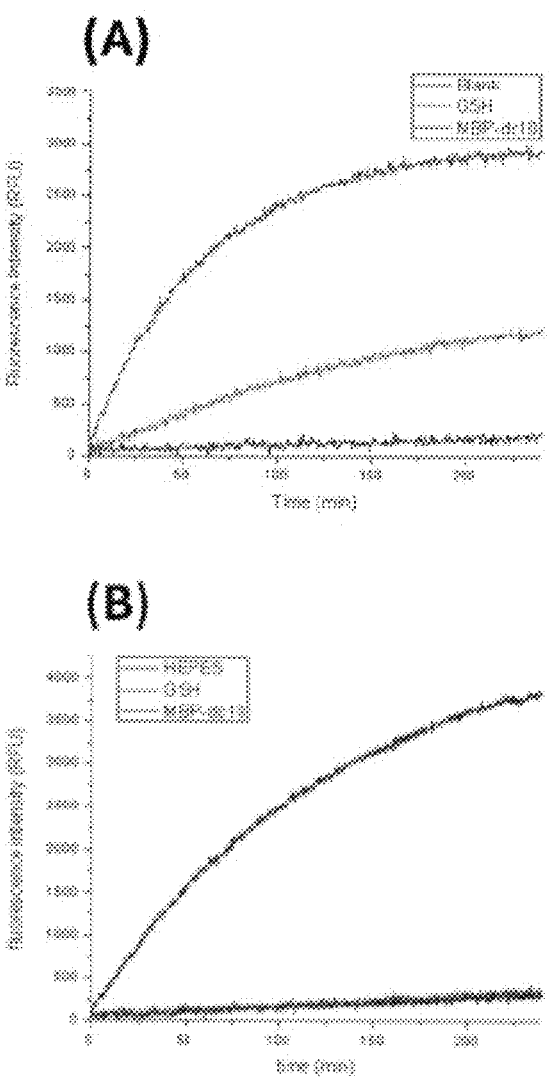
FIG. 10 shows selective reactions of fluorogens YC5 (A) and YC9 (B) with test protein MBP-dC10α (blue) over the tripeptide thiol GSH (red).

Selectivity of the fluorogens was then tested by measuring the rate constants of their reactions with test protein MBP-dC10α and GSH. As shown in FIG. 10, YC5 reacted faster with MBP-dC10α than with GSH, but the latter reaction was still appreciable. However, for YC9, the reaction with GSH was completely suppressed, while the reaction with MBP-dC10α was still rapid.

Figure 11:
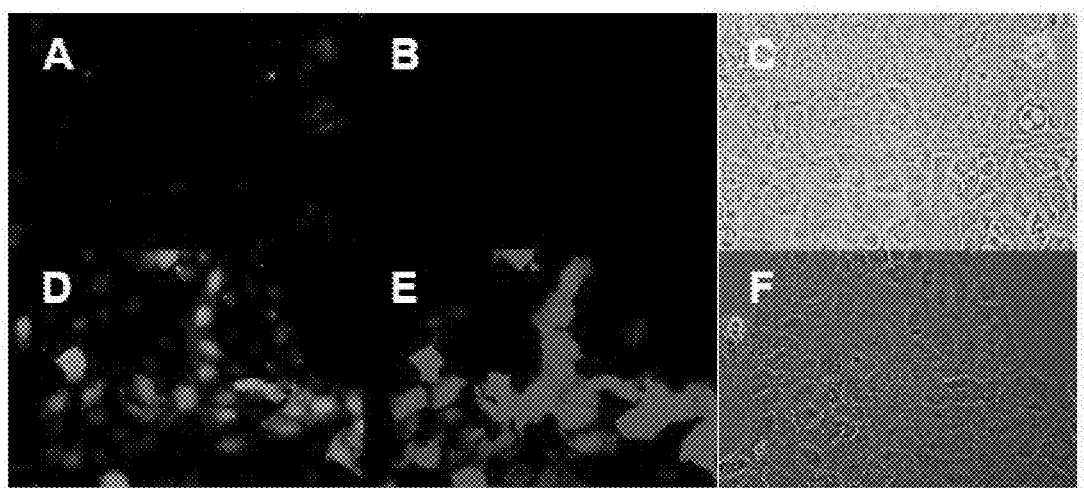
FIG. 11 shows intracellular labelling of test protein cmyc-mNeptune-dC10α with fluorogen YC9. Images A-C show cells transfected with empty (mock) vector, while images D-F show cells transfected with the test protein. Images A & D were obtained in the green channel (YC9 emission) and images B & E were obtained in the red channel (mNeptune emission). Images C & F were under bright field (visible) illumination.

We then tested the highly selective labelling reagent YC9 in cell labelling studies. The red fluorescent protein mNeptune was chosen as a target protein so that its intrinsic fluorescence would serve as a control for the transfection and expression of the target protein. The target sequence dC10α was cloned to its C-terminus and the cmyc epitope (which would ensure the protein was also at least partially directed to the nucleus) was cloned to its N-terminus. As shown in FIG. 11, ~80% of the HEK293 cells transfected with the plasmid coding for expression of the cmyc-mNeptune-dC10α test protein showed red fluorescence throughout the cell (cytosol and nucleus), indicative of test protein expression (FIG. 11E). FIG. 11A shows that minimal background fluorescence was observed, indicative of the low level of non-specific fluorescent labelling. Furthermore, fluorescent labelling was most intense and nearly limited to cells (FIG. 11D) that expressed the target red fluorescent test protein (FIG. 11E). Taken together, these results confirm the high selectivity of fluorogen YC9 for labelling a dC10α-tagged target protein in living cells.

These results indicate that YC9 is a novel protein labelling reagent comprising an asymmetric dimaleimide unit that fluorescently labels a POI bearing a dC10α tag, with great selectivity in living cells. Kinetic studies clearly showed that this improved selectivity for the dC10α tag over mono-thiol compounds was due to the attenuated reactivity of one of the two maleimide groups. YC9 and other fluorogenic labelling agents provided herein thus show great potential for general application to labelling proteins in living cells.

Photophysical Properties of YC15-YC19 Before and after Protein Labelling

Fluorogens YC15-YC19 showed minimal background fluorescence and exhibited strong fluorescence after labelling a dC10-tagged target protein. These properties make fluorogens YC15-YC19 excellent "turn-on" fluorescent labelling reagents with negligible background fluorescence.

Figure 2:
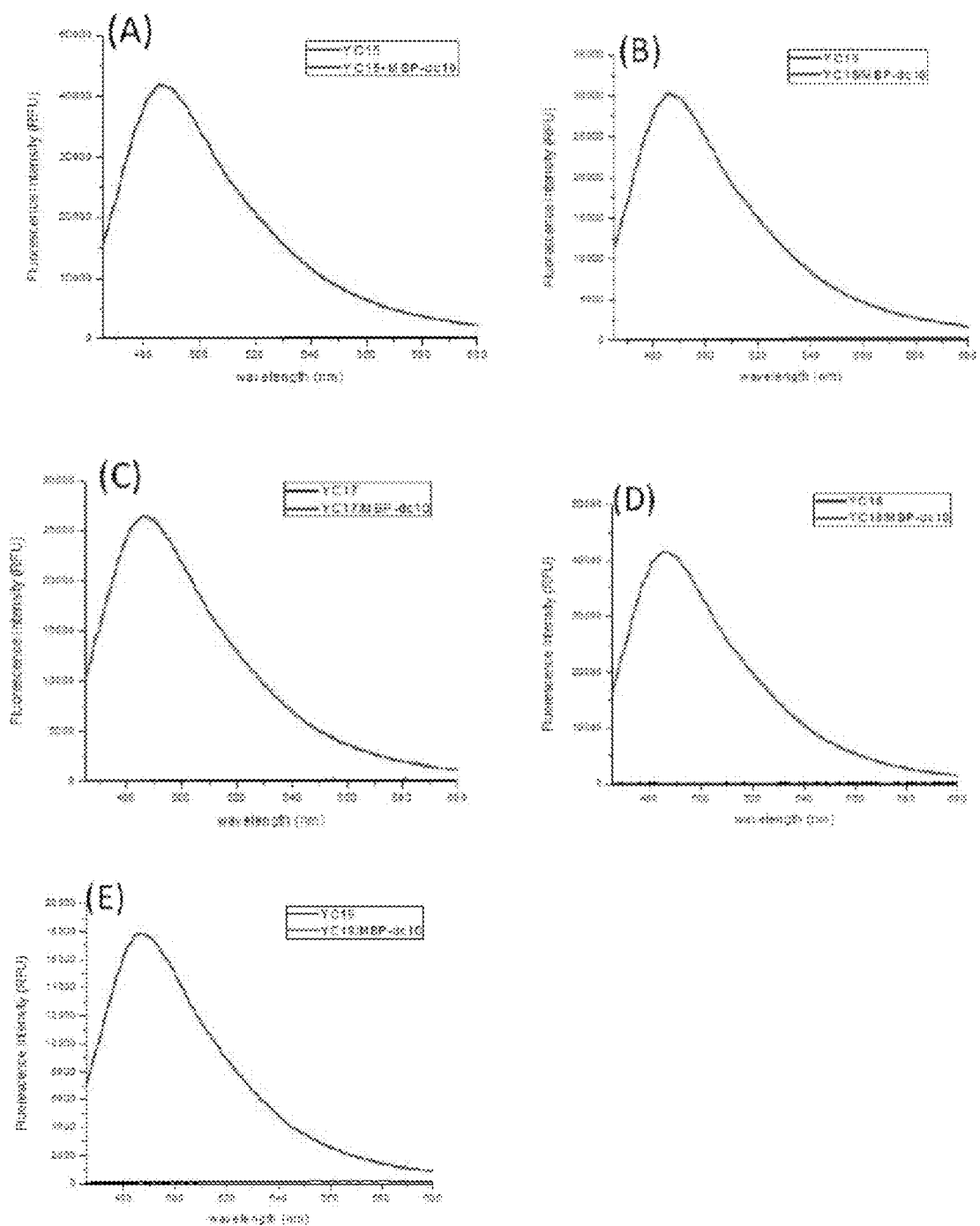
FIG. 2 is an illustration of the fluorescent emission spectra of 25 μM of fluorogens (A) YC15, (B) YC16, (C) YC17, (D) YC18 and (E) YC19 before (black line, near x-axis) and after (red line) labelling with 25 μM model target protein MBP-dC10 in 50 mM HEPES buffer (pH 7.4). $\lambda_{ex}$=440 nm.

The fluorescence emission spectra of fluorogens YC15-YC19 before and after labelling with model target protein MBP-dC10 are shown in FIG. 2. Fluorescence intensity changes (fluorescence enhancement) for all these fluorogens at their maximum emission wavelengths are summarized in Table 1.

TABLE 1

Fluorescence enhancement (FE) of fluorogens YC15-YC19 after labeling with model target protein MBP-dC10 ($\lambda_{ex}$ = 440 nm, $\lambda_{em}$ = 485 nm)

| Fluorogens | YC15 | YC16 | YC17 | YC18 | YC19 |
| --- | --- | --- | --- | --- | --- |
| FE | 226 | 228 | 194 | 468 | 189 |

Kinetics of Fluorogens YC15-YC19 Labelling Target Protein and Reacting with GSH

Figure 3:
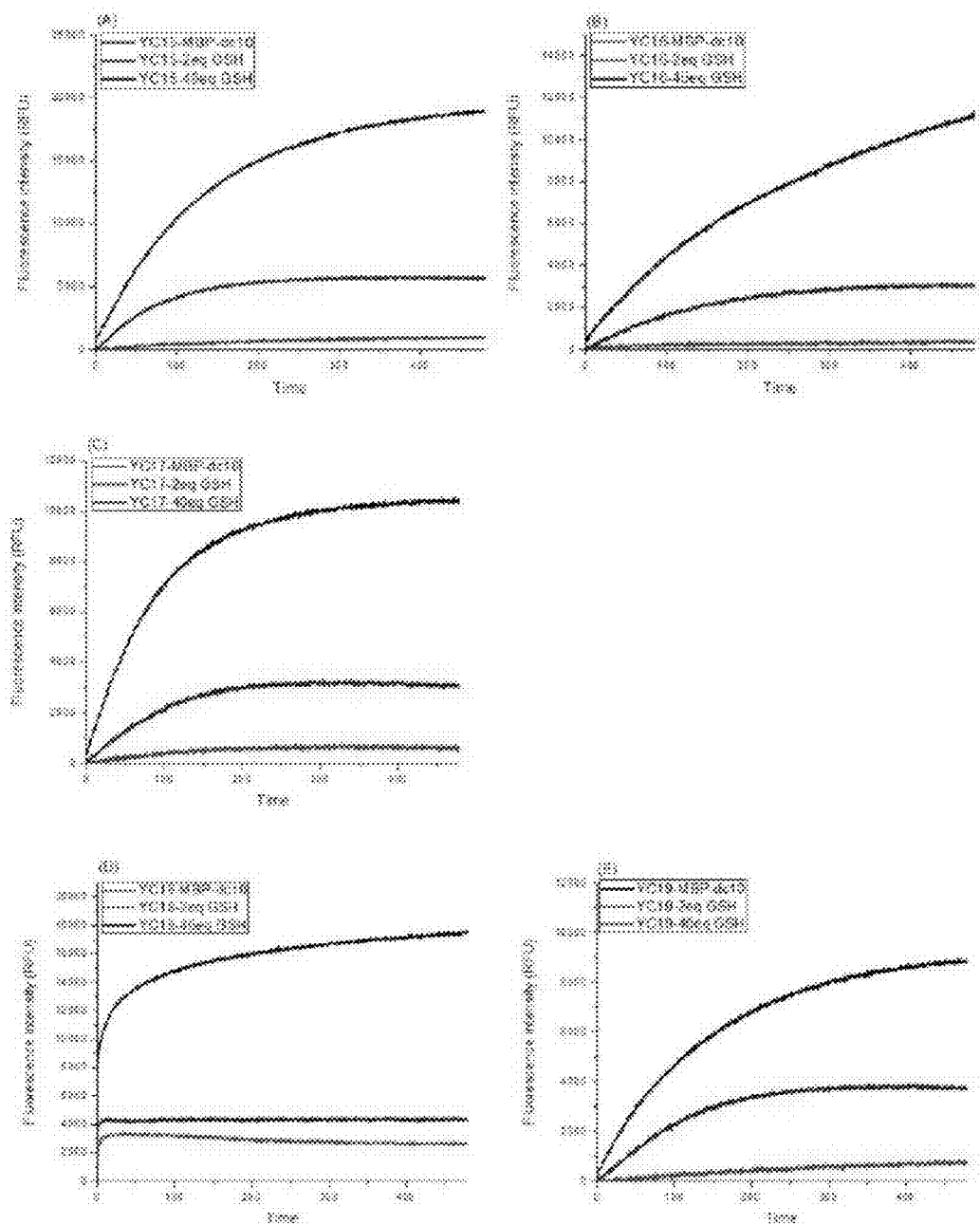
FIG. 3 is an illustration of selective reactions of 25 μM fluorogens YC15 (A), YC16 (B), YC17 (C), YC18 (D) and YC19 (E) with 25 μM test protein MBP-dC10 (black) over the 50 μM tripeptide thiol GSH (red) or 1 mM GSH (blue) in 50 mM HEPES buffer (pH 7.4). $\lambda_{ex}$=440 nm, $\lambda_{em}$=485 nm.

To study the kinetics of reactions of fluorogens YC15-YC19 with test proteins and with other thiols, the reactions of fluorogens YC15-YC19 with test protein MBP-dC10 or tripeptide thiol GSH were monitored by time-dependent fluorescence increase (FIG. 3). YC18 was much more reactive than other fluorogens, so it labelled tagged proteins most efficiently. However, it did not show much difference between the labelling of the target protein and other thiols. This is similar to what has been reported in the literature, namely that bromomaleimide undergoes different reactions with thiols (Youziel, J. et al., Org Biomol Chem 2013, 12, 557-60). All the other fluorogens showed much better reactivity towards target protein MBP-dC10 than the tripeptide thiol GSH. They had almost no reaction with one equivalent of GSH and still underwent a much slower reaction even in the presence of a large excess of GSH.

Figure 4:
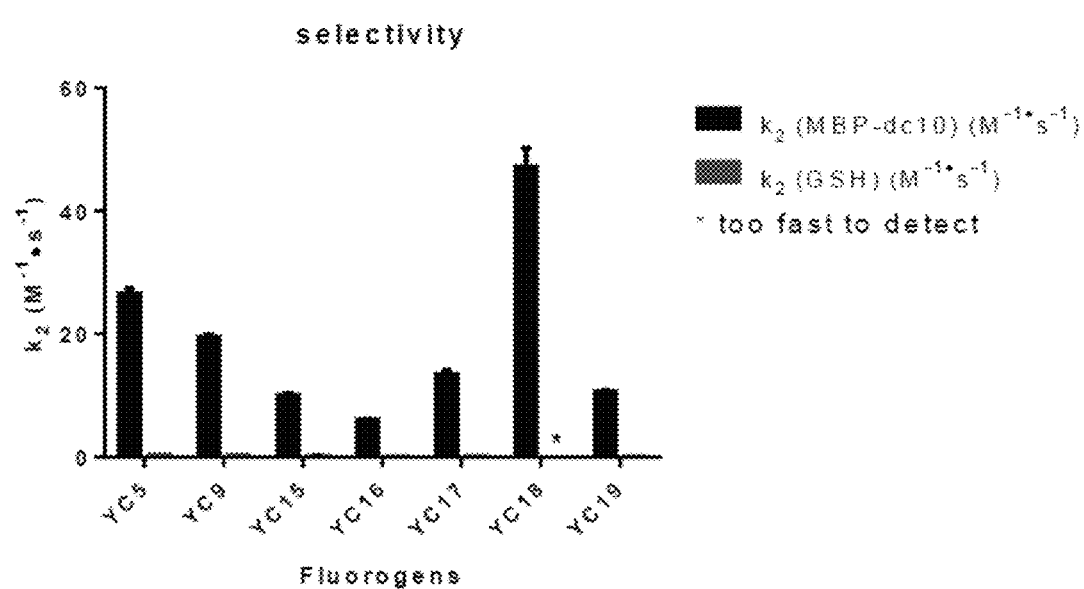
FIG. 4 shows rate constants (mean±SD) for the labelling reaction of fluorogens with test protein MBP-dC10 (black) or GSH (red, close to x-axis).

The rate constants of the labelling reactions of the fluorogens with target protein MBP-dC10 or with GSH were calculated and analyzed to compare fluorogen reactivity towards target protein and GSH (FIG. 4). This difference in reactivity represents the expected selectivity of labelling target protein over GSH. All fluorogens except YC18 were thus found to react highly selectively with target protein.

Figure 5:
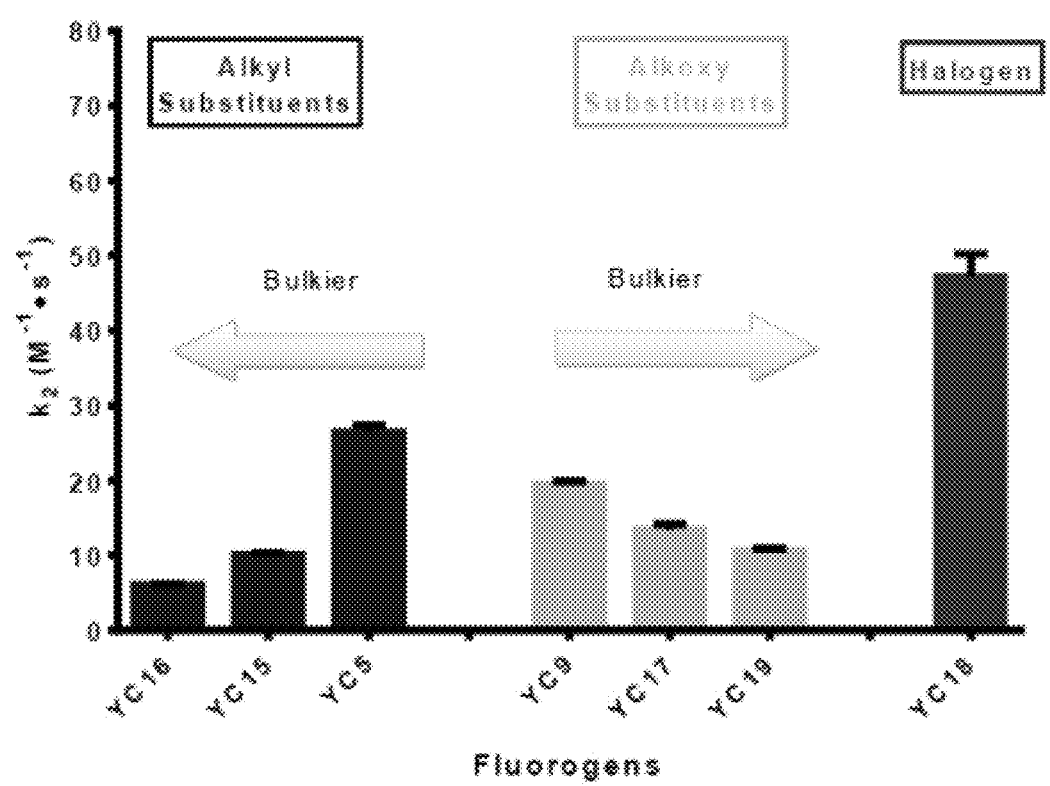
FIG. 5 shows rate constants for the labelling reaction of fluorogens with test protein MBP-dC10.

The rate constants of the labelling reactions of the fluorogens with target protein MBP-dC10 were then analyzed to reveal the effects on the labelling reactions related to the maleimide substituents (FIG. 5). As discussed above, the bromomaleimide group likely undergoes another type of reaction. For maleimides with alkyl or alkoxy substituents, the bulkier the substituents are, the slower the reactions were found to be, suggesting that steric effects played an important role for the reactivity of the labelling reaction. In contrast, there were no clear trends for the electronic effects comparing fluorogens with the alkyl-(YC5-YC15-YC16) or alkoxy-substituted maleimides (YC9-YC17-YC19).

Fluorescence Properties of YC20 and Fluorescence Changes after Labelling Target Protein As described above for other coumarin-based fluorogens, fluorogen YC20 also showed negligble background fluorescence and strong fluorescence after labelling a dC10-tagged target protein. It is thus an excellent "turn-on" fluorescent labelling reagent with negligible background fluorescence.

Figure 6:
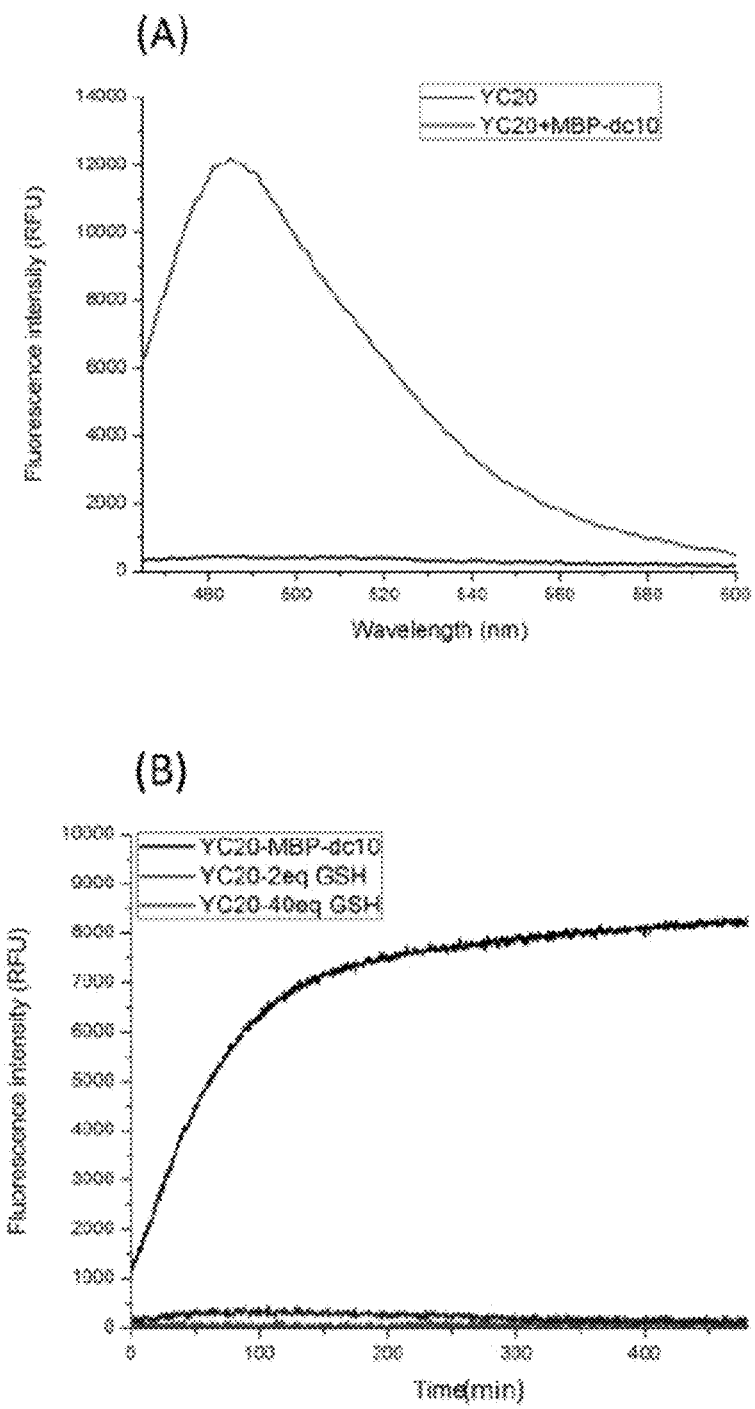
FIG. 6 shows (A) Fluorescence emission spectra of 25 μM fluorogen YC20 before (black line) and after (red line) labelling with 25 μM model target protein MBP-dC10 in 50 mM HEPES buffer (pH 7.4). $\lambda_{ex}$=440 nm; and (B) Selective reactions of 25 μM fluorogens YC20 with 25 μM test protein MBP-dC10 (black) over the 50 μM tripeptide thiol GSH (red) or 1 mM GSH (blue) in 50 mM HEPES buffer (pH 7.4). $\lambda_{ex}$=440 nm, $\lambda_{em}$=485 nm.

The fluorescence emission spectra of fluorogen YC20 before and after labelling with model target protein MBP-dC10 are shown in FIG. 6(A). The fluorescence intensity change (fluorescence enhancement) for YC20 was 29-fold.

Kinetics of Fluorogens YC20, Labelling Target Protein and its Reaction with GSH

To study the kinetics of the fluorogen YC20 labelling a target protein and its reactivity with another thiol, the reactions of fluorogens YC20 with test protein MBP-dC10 or tripeptide thiol GSH were monitored by time-dependent fluorescence increase (FIG. 6(B)). Its reaction with the target protein was similar to that of the other fluorogens, but its reaction with GSH was extremely slow, even in the presence of a large excess of GSH. YC20 thus represents the most selective labelling reagent identified to date.

Comparison of the Selectivity of YC20 for Labelling Target Protein Over GSH, Relative to Other Fluorogens.

Figure 7:
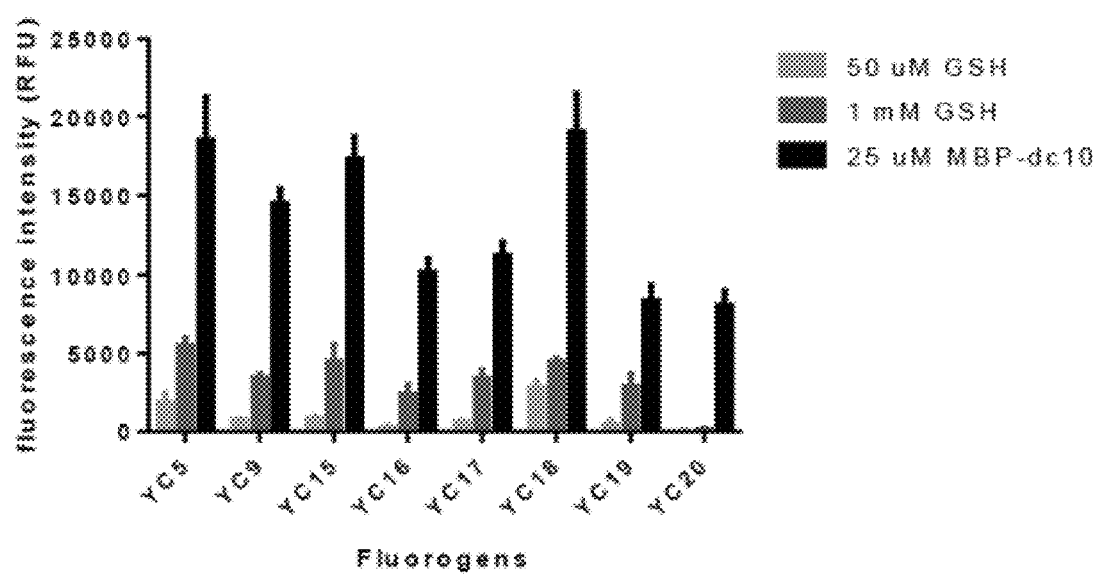
FIG. 7 shows fluorogens' selectivity of labelling target protein (MBP-dC10) over GSH. 25 μM Fluorogen reacted with 25 M MBP-dC10, 50 M GSH or 1 mM GSH in 50 mM HEPES buffer (pH 7.4). $\lambda_{ex}$=440 nm, $\lambda_{em}$=485 nm.

A comparison was made of the selectivity of each fluorogen to label a target protein rather than GSH (see FIG. 7). YC18 labelled the protein most efficiently, but not as selectively as other fluorogens. YC9, YC15, YC16, YC17 and YC19 showed similar selectivity of labelling target protein—namely, they did not react with a low concentration of GSH but showed some signal after incubation with a high concentration of GSH. YC20 was shown to be the most selective labelling reagent; even after incubation with a high concentration of GSH, it did not give any fluorescence signal.

Cytotoxicity Test for YC20 and YC21M

Figure 8:
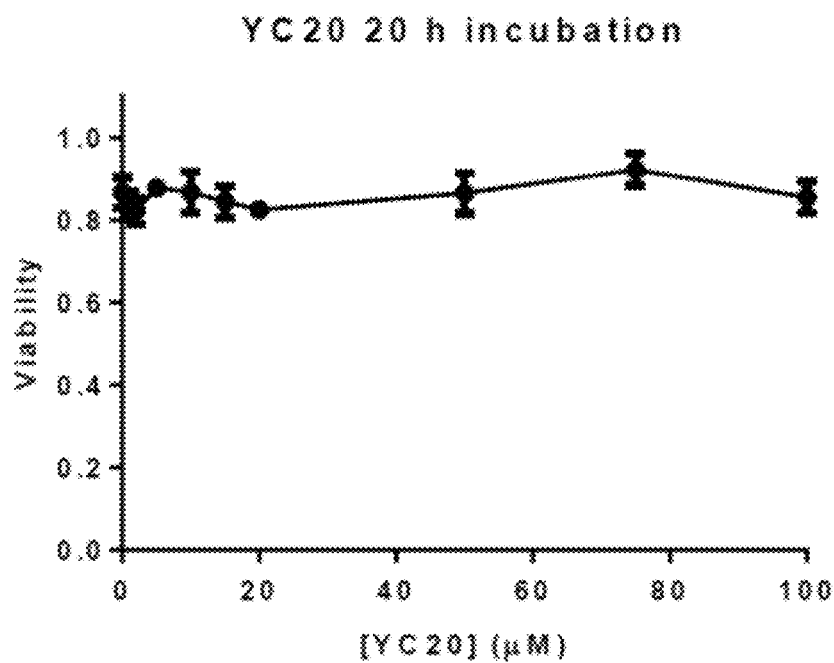
FIG. 8 shows cytotoxicity of YC20 and YC21M in cultured HEK293T cells. The cells were incubated with the fluorogens at corresponding concentrations for 20 h. Cell viability was measured by MTT assay and the results are reported as percentage relative to untreated cells (mean±SD). (A) Cytotoxicity of YC20 in cultured HEK293T cells. (B) Cytotoxicity of YC21M in cultured HEK293T cells.
Figure 8:
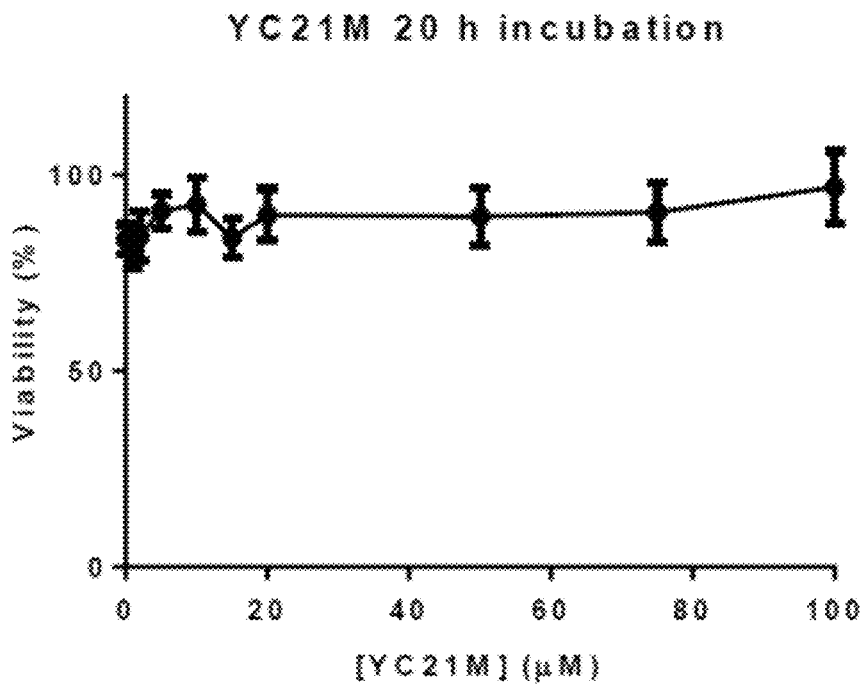

In view of the results shown above, YC20 and YC21M are promising candidates for no-wash intracellular protein labelling reagents and subcellular protein labelling reagents. Their cytotoxicity was therefore investigated. Using the MTT assay to determine the cytotoxicity of fluorogens YC20 and YC21M, neither showed any cytotoxicity up to 100 μM of fluorogen, after 20 h incubation with HEK293T cells (see FIG. 8). By way of reference, it is noted that a typical labelling experiment uses 25 μM labelling agent over a 3-h period.

Intracellular labelling of dC10α-actin and histone H2B-dC10α in HEK 293T Cells

Figure 13:
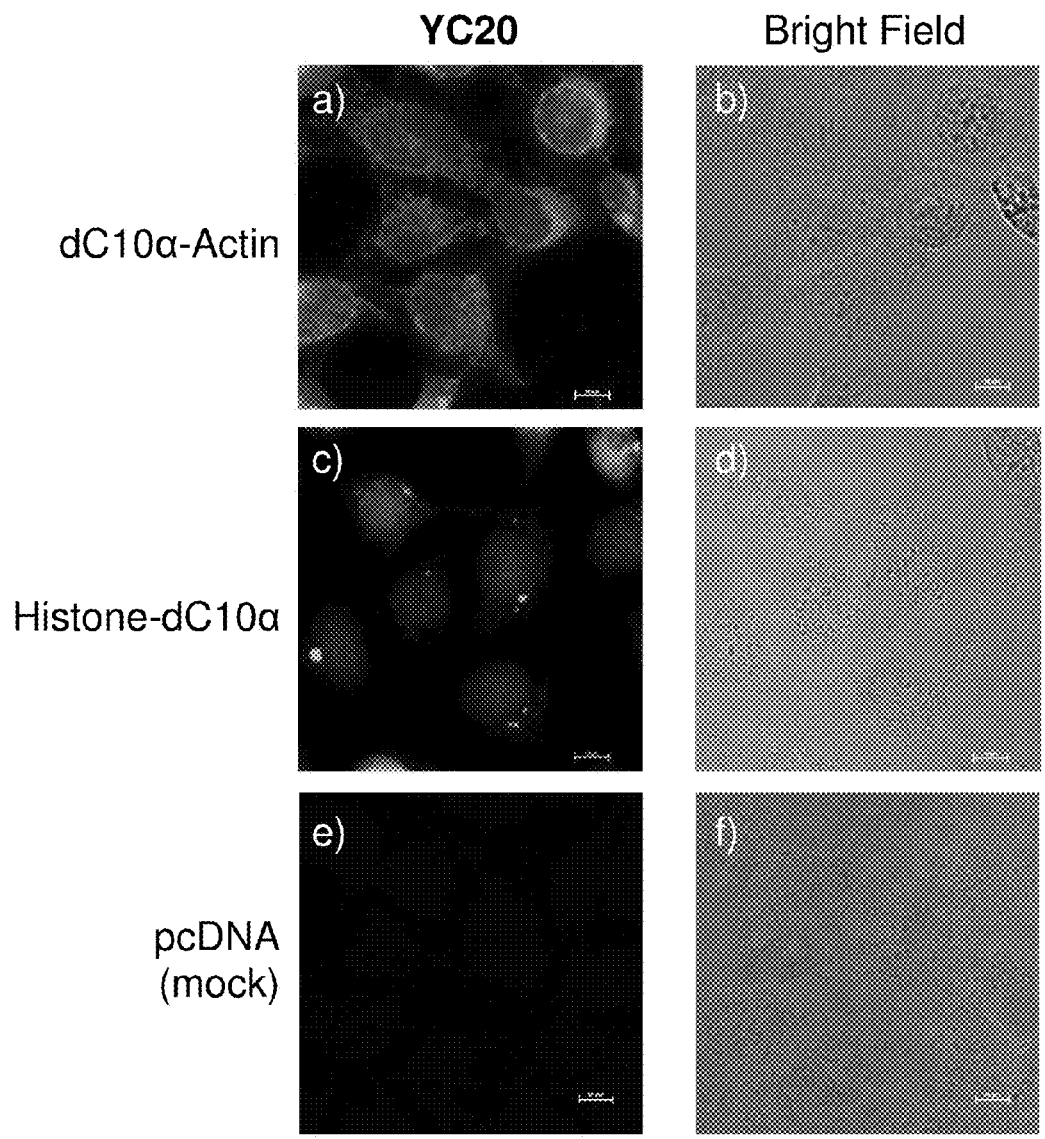
FIG. 13 shows fluorescence images (left column) and corresponding bright-field (right column) for no-wash cell labeling with YC20 on confocal microscope: (a, b) dC10α-actin transfected cells treated with YC20; (c, d) Histone H2B-dC10α transfected cells treated with YC20; (e, f) pcDNA transfected cells (mock cells) treated with YC20. Scale bars=10 µm. Cyan fluorescence conditions: Em 482 nm (bandwidth: 35 nm), dichromic mirror: 400-457 nm.

The no-wash fluorogenic labelling reagent YC20 was used to label cellular proteins localized in different parts of living HEK 293T cells. Histone-H2B, localized in the nuclei, and actin, localized as filaments in the cytosol, were chosen as the test proteins. The target sequence dC10α was cloned to the C-terminus of Histone-H2B and to the N-terminus of actin as described below, demonstrating that the target sequence can be fused to either terminus of a POI. HEK293T cells were transfected to express histone H2B-dC10α or dC10α-actin and then labeled with YC20 for 45 min and directly imaged by fluorescent microscopy without any washing steps (FIG. 13; see, also, Chen, Y. et al., Angew. Chem. Int. Ed. Engl., 2014, 53, 13785-13788, the entire contents of which are hereby incorporated by reference). For dC10α-actin transfected cells, filament structures in the cytosol were clearly visible in the cyan channel of the microscope, indicating the dC10α-actin was labeled by YC20. For cells transfected with histone H2B-dC10α, only the nuclei were fluorescently labeled and visible in the cyan channel, showing that YC20 specifically labeled histone H2B-dC10α in these cells. Cells transfected with pcDNA (mock cells) showed negligible fluorescence in this negative control, demonstrating the selectivity of the labeling method.

Transfection and labelling were performed as follows: HEK 293T cells were plated into 60-mm dishes and grown in MEM supplemented with 10% FBS, 100 units/mL of penicillin and 100 μg/mL of streptomycin for 16 h before transfection. Cells were transiently transfected with plasmid DNA encoding for dC10α-actin or histone H2B-dC10α or with pcDNA3.1 (mock) using lipofectamine 2000 following manufacturer's instructions. Twenty-four or forty-eight hours after transfection, the cells were incubated with 10 µM YC20 (in Opti-MEM with 0.2% DMSO) for 45 min at 37° C. Cells were observed and imaged on a Nikon confocal microscope with a 25× objective. Images were taken and analyzed with NIS-Elements software.

Intracellular Labelling of Histone H2B-dC10α in HeLa Cells

Figure 14:
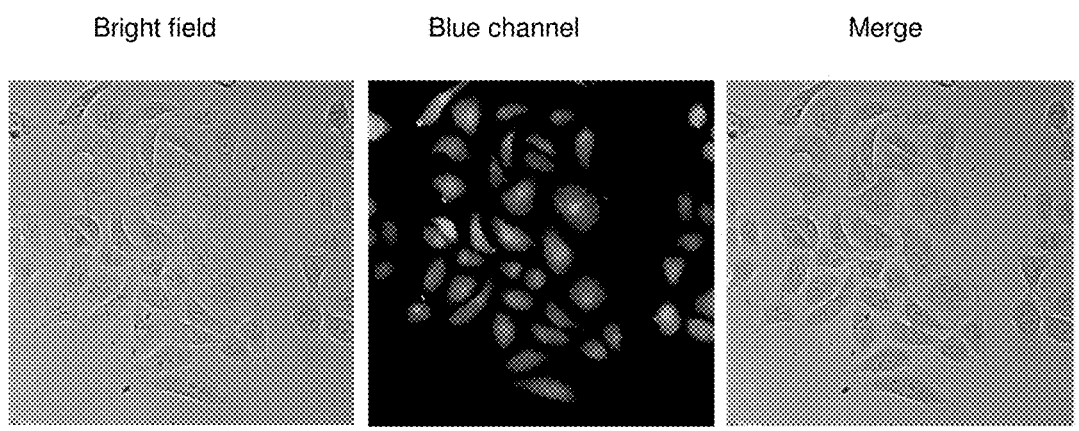
FIG. 14 shows bright-field (left), fluorescence (middle) and overlaid (right) images for no-wash cell labeling with YC20 on confocal microscope: Transfected HeLa cells expressing histone H2B-dC10α treated with 10 µM YC20 for 10 minutes labelling. Cyan fluorescence conditions: Em 482 nm (bandwidth: 35 nm), dichromic mirror: 400-457 nm.

The fluorogenic labelling agent YC20 was used to label the target protein histone H2B-dC10α in living HeLa cells, to demonstrate that a variety of cell lines are amenable to this labelling strategy. HeLa cells were transfected with plasmid DNA encoding histone H2B-dC10α as described below and labelled with 10 µM YC20 for 10 minutes. As shown in FIG. 14, the nuclei were strongly fluorescently labeled and visible in the cyan channel, showing that YC20 specifically labeled histone H2B-dC10α in the nuclei of these cells (FIG. 14, merged image).

Transfection and labelling were performed as follows: HeLa cells were propagated for 2-3 weeks until the cells were stable and healthy for the transfection and labelling experiments. Cells were plated in 35 mm culture dishes (approx. $1.3 \times 10^5$ cells/plate in 2 mL of MEM or DMEM media) and incubated at 37° C. (5% $CO_2$) for 12-16 h, after which they were transfected with the plasmid DNA encoding for the expression of histone H2B C-terminally tagged with dC10α, using 3-fold lipofectamine 2.8 µg (H2B-dC10α and 6 µg of lipofectamine). For the transfections the media was changed from MEM/DMEM to OPTI-MEM and the transfection time was 45 min. The media was then changed back to MEM/DMEM and the cells were allowed to express protein for 48 h (37° C. and 5% $CO_2$), after which the cells were treated with the corresponding fluorogen. For FlARe labelling, cells were treated with 10 µM of YC20 in 2 mL OPTI-MEM (containing 0.02% F127 and 0.2% DMSO) and incubated at 37° C. and 5% $CO_2$ for 10 minutes.

Materials and Methods

1. General Procedures.

All reagents and solvents for reactions were used as received unless otherwise stated. Dichloromethane, and acetonitrile were dried by the solvent purification system LC Technology Solution Inc. All reactions were performed under an inert atmosphere (e.g. $N_2$) in oven-dried apparatus unless otherwise stated.

Reactions were monitored by thin layer chromatography (TLC) using E. Merck silica gel 60F254 pre-coated aluminum plates. Components were visualized by illumination with a short-wavelength ultra-violet light or long-wavelength visible light after which staining in $KMnO_4$ solution followed by heating. Flash column chromatography was performed on ZEOCHEM® silica gel 60 (ECO 40-63 µm) using ethyl acetate/n-hexane or acetonitrile/dichloromethane as eluting solvents.

Nuclear magnetic resonance (NMR) spectra were recorded in deuteriochloroform with tetramethylsilane (TMS) as internal reference at ambient temperature unless otherwise stated. The experiments were performed mainly on a Bruker Avance 300 Fourier Transform Spectrometer operating at 300 MHz for $^1$H and at 75.47 MHz for $^{13}$C or Bruker Avance 400 Fourier Transform Spectrometer operating at 400 MHz for $^1$H and at 100.6 MHz for $^{13}$C.

EI-MS spectra were recorded on a Kratos concept mass spectrometer for both low resolution and high resolution mass spectra. ESI-MS spectra were recorded on a Waters Micromass Q-T of mass spectrometer.

Melting points were measured on an EZ-Melt automated melting point apparatus and uncorrected.

Ultraviolet absorption spectra and fluorescence spectroscopic studies were performed on a Synergy H4 Hybrid Multi-Mode Microplate Reader.

2. Cloning and Expression.

Cloning and expression of MBP-dC10α was done as described (Guy, J. et al., Mol. Biosyst. 2010, 6, 976-987).

3. Determination of Fluorescence Properties of Fluorogens, Fluorescence Changes after Labelling of Target Protein, and Fluorescence Enhancement Ratios.

Emission spectra and fluorescence intensity measurements were recorded at 37° C. with a Synergy H4 Hybrid Multi-Mode Microplate Reader with excitation and emission monochromators set at 9 nm bandpass. The mixture of 100 µM solution of fluorogen (YCx) and 100 µM MBP-dC10 in 50 mM HEPES buffer (pH 7.4) with 5% DMSO was incubated at 37° C. in the dark for 12 hours, after which the fluorescence emission spectrum of a dilution (25 µM final) in 50 mM HEPES buffer with 5% DMSO was recorded. The emission spectra of the corresponding labelling reagent in same solution without MBP-dC10α were also recorded. The ratio of fluorescence intensity at maximum emission gave the fluorescence enhancement (FE) ratio.

4. Kinetic Model for Consecutive Pseudo First Order Reactions.

The following model was used:

Reaction:

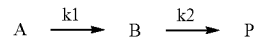

$$I = I_P + I_A + I_B$$

$$= p*[P] + a*[A] + b*[B]$$

$$= p\left\{[A]_0 - [A]_0 * e^{-k_1*t} - \frac{k_1*[A]_0}{(k_2-k_1)}(e^{-k_1*t} - e^{-k_2*t})\right\} + a[A]_0 * e^{-k_1*t} +$$

$$b*\frac{k_1*[A]_0}{(k_2-k_1)}(e^{-k_1*t} - e^{-k_2*t})$$

$$= p[A]_0 + (a-p)-[A]_0 * e^{-k_1*t} + (b-p)\frac{k_1*[A]_0}{(k_2-k_1)}(e^{-k_1*t} - e^{-k_2*t})$$

$$= [A]_0\left\{p+(a-p)*e^{-k_1*t} + (b-p)\frac{k_1}{(k_2-k_1)}(e^{-k_1*t} - e^{-k_2*t})\right\}$$

where I is fluorescence intensity, and the fluorescence intensity is linearly proportional to the concentration, since the concentration of fluorogen used here is within the linear range. So $I_A=a*[A]$; $I_B=b*[B]$; $I_P=p*[P]$; $[A]0=2.5*10^{-5}$. With this formula, there will be 5 parameters, but based on the nature of the reaction and the fluorescent properties of the compounds, the 5 parameters can be restrained as: $p>b>a>0$; $k_1>k_2>0$. Finally, the formula and the conditions were applied in Origin 6.0 to fit the curves by non-linear regression, yielding values for the $k_{obs}$ for each step.

5. Kinetic Studies.

Figure 12:
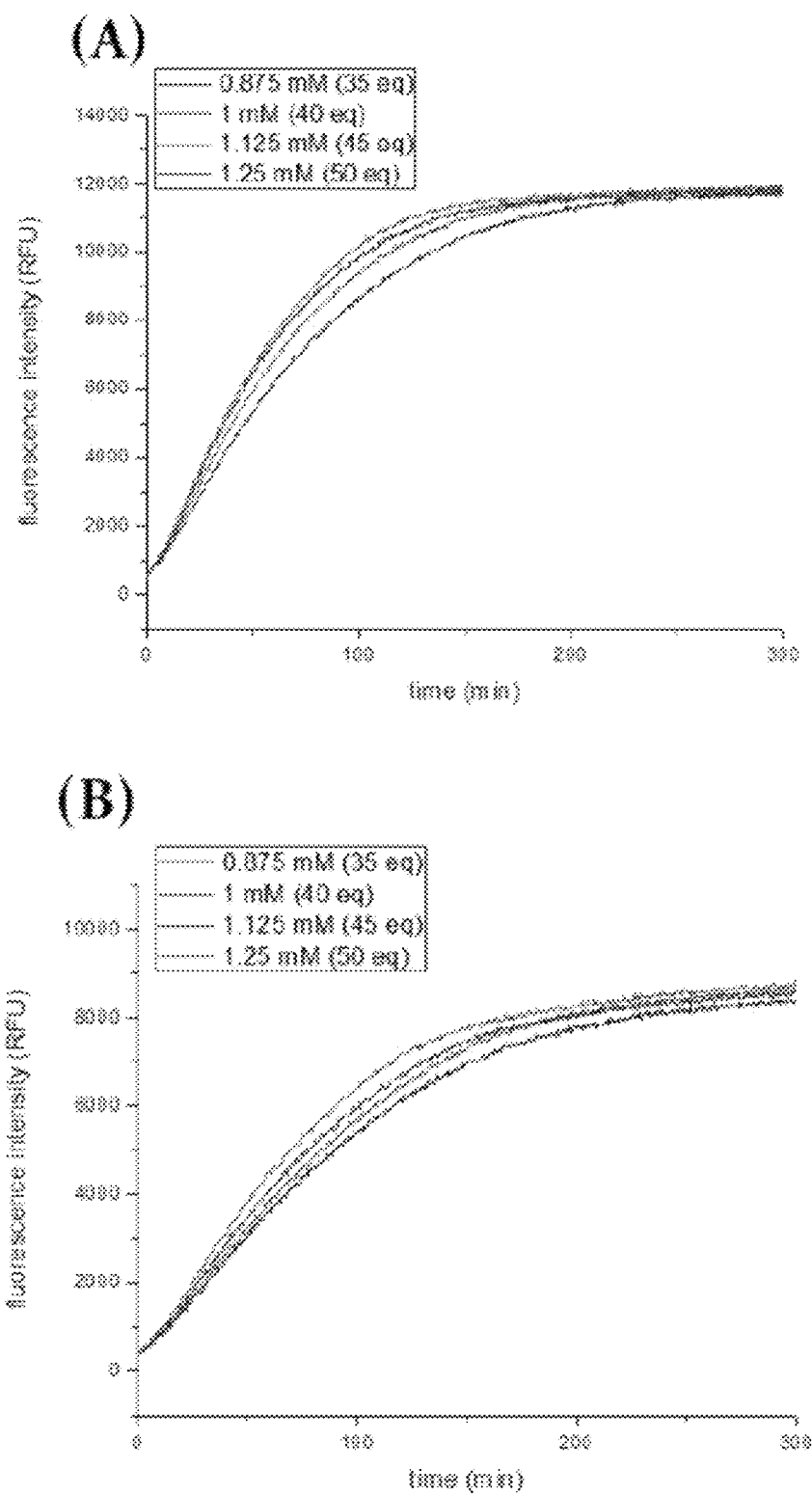
FIG. 12 shows time dependent fluorescence increase for YC5 (A) and YC9 (B) reacted with 0.875 mM, 1 mM, 1.125 mM or 1.25 mM in 50 mM MPA in 50 mM HEPES buffer (pH 7.4) with 5% DMSO. $\lambda_{ex}$=440 nm and $\lambda_{em}$=485 nm, 37° C.

Kinetic experiments were carried out at 37° C. using Synergy H4 Hybrid Multi-Mode Microplate Reader with excitation and emission monochromators 9 nm bandpass. Solutions with different MPA concentrations were prepared in 96-well plate and labelling reagent (YC5 or YC9) in DMSO was added immediately before recording. The final concentration of labelling reagent was 25 µM and the final concentrations of MPA were 0.875 mM, 1 mM, 1.125 mM or 1.25 mM in 50 mM HEPES buffer (pH 7.4) with 5% DMSO (FIG. 12). Samples were excited at 440 nm and fluorescence intensity was followed at 485 nm as a function of time. All the time-dependent fluorescence increase curves were fitted by non-linear regression according to the formula from the last section using Origin to get $k_{obs}$. $k_{obs}$ was plotted against MPA concentrations to obtain a second order rate constant.

6. Measuring Time-Dependent Fluorescence Increase.

Reactivity was tested through the time-dependent fluorescence increase at 37° C. using Synergy H4 Hybrid Multi-Mode Microplate Reader with excitation and emission monochromators set to 9 nm bandpass. All reactions were prepared in 50 mM HEPES buffer (pH 7.4) with 5% DMSO. Solutions of MBP-dC10α or GSH were prepared in 96-well plates and labelling reagent (YCx) in DMSO was added immediately before recording. The final concentration of labelling reagent was 25 μM, the final concentration of MBP-dC10α was 25 μM and the final concentration of GSH was 50 μM or 1 mM in 50 mM HEPES buffer (pH 7.4) with 5% DMSO. Samples were excited at 440 nm and fluorescence intensity was followed at 485 nm as a function of time.

7. Cellular Labelling.

HEK 293T cells were plated into 6-well plates equipped with 25 mm×25 mm coverslips and grown in DMEM supplemented with 10% FBS 16 h before transfection. Cells were transiently transfected with mNeptune-dC10α or pcDNA3.1 using lipofectamine 2000. Either 24 or 48 h after transfection, the cells were washed with complete DMEM and incubated with 25 μM YC9 in DMEM for 30 min at 37° C. The media with labelling reagent was removed and followed by 3 times washing over 3 h at 37° C. Cells were fixed after labelling for imaging on a Carl Zeiss Axiophot inverted microscope.

8. MTT Assay.

3-(4,5-Dimethylthiazol-2-yl)-2,5-diphenyl tetrazolium bromide (MTT) is a yellow tetrazolium salt and can be reduced to formazan crystals, which are insoluble in aqueous solutions, by active mitochondria in living cells. The resulting intracellular purple formazan can be dissolved in Triton X100, and therefore quantified by measuring absorption of the solution.

Cells were seeded in a 96-well plate and incubated with 100 μL of culture medium with different amounts of the fluorogen YCx for 16 h. No fluorogen was added to the positive control and no cells were plated in the negative control. Portions of 25 μL of MTT solution (5 mg in 1 mL of Hanks' balanced salt solution) were added to the wells and the cells were further incubated at 37° C. for 4 h. Solubilization solutions (100 μL) were then added and incubated in 96-well plates at room temperature in the dark overnight. The absorption of each well was measured using a plate reader at a wavelength of 570 nm with 690 nm as a reference. Cell viability was calculated according to the following equation: Cell viability=($A_{with\ fluorogen}$−$A_{negative\ control}$)/($A_{positive\ control}$−$A_{negative\ control}$).

9. Cloning of dC10α-Actin and H2B-dC10α.

The plasmid containing the gene encoding for the expression of β-actin with an N-terminal fused EGFP in mammalian cells is described in Charras, G. T. et al., J. Cell. Biol., 2006, 175, 477-90. The plasmid encoding for expression of human histone H2B linked to a C-terminal fused mCherry was purchased from Addgene (Cambridge, Mass.; Plasmid ID 20972).

Mammalian cell vectors for the expression of dC10α-actin or H2B-dC10α were prepared using double-stranded DNA gBlocks™ gene fragments. DNA gBlocks™ encoding for the dicysteine helical tag dC10α were synthesized (Integrated DNA technologies, Coralville, Iowa) (Table 3). DNA gBlocks™ were designed to contain the restriction sites NheI and XhoI (dC10α-actin gBlock) or BamHI and XbaI (H2B-dC10α gBlock). For the preparation of the dC10α-actin gene fusion construction, digestion of the dC10α-actin gBlock fragment with NheI/XhoI was followed by subcloning into NheI/XhoI digested and shrimp alkaline phosphatase-treated EGFP-Actin vector. Preparation of the H2B-dC10α construction involved digestion of the H2B-dC10α gBlock fragment with BamHI/XbaI followed by subcloning into BamHI/XbaI digested and shrimp alkaline phosphatase-treated H2B-mCherry. Digested destination vectors were gel-purified (1% agarose gel) using a Gel DNA Recovery Kit (Clontech, Mountain View, Calif.). Digested gBlock fragments were purified using QuickClean™ enzyme removal resin (Clontech, Mountain View, Calif.). The ligated DNA constructs were transformed into chemical competent E. coli DH5α. All DNA sequences were confirmed by Sanger sequencing (McGill Genome Quebec sequencing facility).

TABLE 3

Double stranded gBlock gene fragments.

dC10α-actin gBlock
5'-
TATAAGCAGAGCTGGTTTAGTGAACCGTCAGATCCGCTAGCGATGCT
GAGCGCTGCTGAGTGCGCTGCTAGAGAAGCTGCATGCAGAGAAGCTG
CAGCTAGAGCTGGAGGAAAGGGATCTTCACTCGAGGATGATGATATC
GCCGCGCTCGTCGTCGACAACGGCTCCGGCATGTGCAAGGCCGGCTT
CGCG-3'

H2B-dC10α gBlock
5'-
CATGCTGTGTCCGAGGGCACTAAGGCAGTTACCAAGTACACTAGCTC
TAAGGATCCAGGATCTTCACTGAGCGCTGCTGAGTGCGCTGCTAGAG
AAGCTGCATGCAGAGAAGCTGCAGCTAGAGCTGGAGGAAAGTAATCT
AGAGGGCCCTATTCTATAGTGTCACCTAAATGCTAGAGCTCGCTGAT
CAGC-3'

Synthesis Methods and Characterization

Synthesis of YC5, YC24-YC26.

The protocol for the synthesis of compound 8 and 9 has been reported (Keillor, J. W. et al., Org. Biomol. Chem. 2011, 9, 185-197); the synthesis of coumarin derivatives 1 and 2 has also been reported (Ma, Y. M. et al., J. Med. Chem. 2004, 47, 6349-6362); and tert-butyl piperzine-1-carboxylate 3 was also synthesized as reported (Yan, S. S. et al., Bioorg Med Chem Lett 2010, 20, 1302-1305).

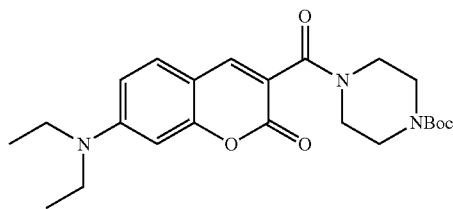

tert-butyl 4-(7-(diethylamino)-2-oxo-2H-chromene-3-carbonyl)piperazine-1-carboxylate (4)

7-Diethylaminocoumarin-3-carboxylic acid (52 mg, 0.2 mmol) and tert-butyl piperazine-1-carboxylate (3) (72 mg, 0.4 mmol) were mixed in anhydrous DMF (2 mL), HOBt (32.4 mg, 0.24 mmol) was added and the mixture was stirred at ambient temperature for 10 min, then EDC.HCl (54 mg, 0.28 mmol) was added. The mixture formed was stirred at ambient temperature in the dark overnight. The reaction mixture was diluted with CH₂Cl₂, washed with 0.1 N HCl, saturated NaHCO₃ (aq) and brine, dried over MgSO₄ and concentrated. The residue was purified by flash column chromatography to obtain compound 4 as an orange solid (85 mg, 100% yield). ¹H NMR (400 MHz, CDCl₃): δ (ppm) 7.78 (s, 1H), 7.31 (d, J=8.3 Hz, 1H), 6.60 (d, J=8.2 Hz, 1H), 6.47 (s, 1H), 3.72 (s, 2H), 3.52 (s, 4H), 3.44 (m, 6H), 1.47 (s, 9H), 1.25 (t, J=7.1 Hz, 6H); ¹³C NMR (100 MHz, CDCl₃): δ (ppm) 165.2, 159.1, 157.2, 154.5, 151.7, 145.3, 129.8, 115.8, 109.4, 107.6, 96.8, 80.1, 47.2, 44.9, 42.2, 29.6, 28.3, 12.3; LRMS (EI) m/z (%): 429.2 (M+, 8%); HRMS (EI): calcd for C₂₃H₃₁N₃O₅: 429.2264. found: 429.2282.

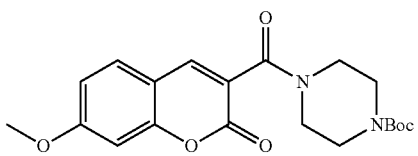

tert-butyl 4-(7-methoxy-2-oxo-2H-chromene-3-carbonyl)piperazine-1-carboxylate (5)

The synthesis of compound 5 followed the same protocol as the synthesis of compound 4 starting with 7-methoxy-coumarin-3-carboxylic acid and tert-butyl piperazine-1-carboxylate (3) to obtain compound 5 as a white viscous oil (77 mg, 100% yield). ¹H NMR (400 MHz, CDCl₃): δ (ppm) 7.93 (s, 1H), 7.45 (d, J=8.5 Hz, 1H), 6.89 (d, J=8.1 Hz, 1H), 6.83 (s, 1H), 3.90 (s, 3H), 3.74 (s, 2H), 3.52 (s, 4H), 3.38 (s, 2H), 1.47 (s, 9H); ¹³C NMR (100 MHz, CDCl₃): δ (ppm) 164.2, 163.9, 158.3, 156.2, 154.5, 144.3, 129.7, 120.8, 113.3, 111.9, 100.6, 80.3, 55.9, 47.1, 43.5, 42.2, 29.7, 28.3.

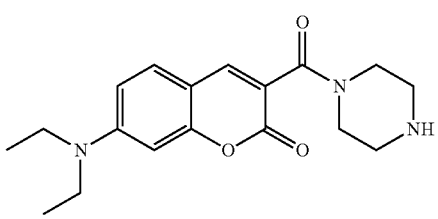

7-(diethylamino)-3-(piperazine-1-carbonyl)-2H-chromen-2-one (6)

TFA (2 mL) was added dropwise to a solution of compound 6 (85 mg, 0.2 mmol) in CH₂Cl₂ (2 mL), and the mixture was stirred at ambient temperature in the dark for 3 h. The volatile components were removed by rotary evaporation. The residue was dried under vacuum as the TFA salt of compound 6 (65 mg, 100%). ¹H NMR (400 MHz, CDCl3): δ (ppm) 7.76 (s, 1H), 7.22 (d, J=8.9 Hz, 1H), 6.52 (dd, J=8.8, 2.4 Hz, 1H), 6.40 (d, J=2.2 Hz, 1H), 3.67 (s, 2H), 3.34 (m, 6H), 2.88 (s, 2H), 2.84 (s, 2H), 1.16 (t, J=7.2 Hz, 6H); ¹³C NMR (100 MHz, CDCl₃): δ (ppm) 165.0, 159.1, 157.2, 151.6, 144.7, 129.8, 116.4, 109.3, 107.7, 96.9, 48.6, 46.2, 45.6, 44.9, 43.3, 29.7, 12.4; LRMS (EI) m/z (%): 329.2 (M⁺, 1%).

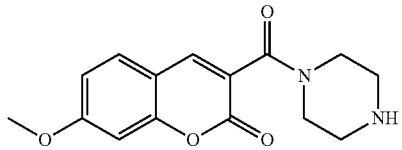

7-methoxy-3-(piperazine-1-carbonyl)-2H-chromen-2-one (7)

The synthesis of compound 7 followed the same protocol as for the synthesis of compound 6, starting with compound 5 to obtain compound 7 as a white viscous oil (58 mg, 100% yield). This product was used in following steps without further purification.

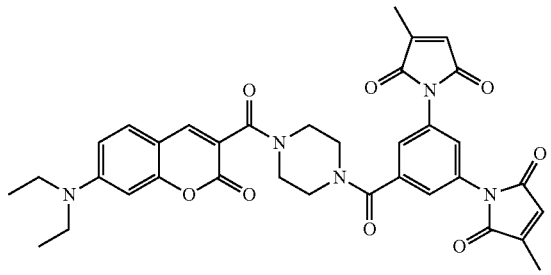

1,1'-(5-(4-(7-(diethylamino)-2-oxo-2H-chromene-3-carbonyl)piperazine-1-carbonyl)-1,3-phenylene)bis(3-methyl-1H-pyrrole-2,5-dione) (YC25)

TBTU and DIPEA were added to a solution of compound 6 and compound 8 in CH₂Cl₂, and this reaction mixture was stirred overnight at ambient temperature in the dark. The reaction mixture was diluted with CH₂Cl₂, washed with 0.1 N HCl (aq), sat. NaHCO₃ (aq) and brine, dried over MgSO₄ and concentrated with rotary evaporation. The residue was purified by flash chromatography to obtain YC25 as a light yellow oil (26 mg, 22% yield). ¹H NMR (400 MHz, CDCl₃): δ (ppm) 7.90 (s, 1H), 7.65 (s, 1H), 7.51 (s, 2H), 7.31 (d, J=8.9 Hz, 1H), 6.60 (dd, J=8.9, 2.1 Hz, 1H), 6.51 (d, J=1.4 Hz, 1H), 6.47 (s, 1H), 3.65 (m, 8H), 3.42 (q, J=7.0 Hz, 4H), 2.18 (s, 6H), 1.16 (t, J=6.8 Hz, 6H); ¹³C NMR (100 MHz, CDCl₃): δ (ppm) 169.9, 168.8, 168.5, 165.4, 159.2, 157.4, 151.9, 146.1, 145.8, 136.3, 132.6, 130.0, 127.7, 123.0, 122.8, 115.6, 109.5, 107.8, 97.00, 47.6, 45.0, 42.2, 38.6, 29.7, 12.4, 11.2; LRMS (ESI) m/z (%): 674 ([M+Na]⁺); HRMS (ESI): calcd for C₃₅H₃₃N₅NaO₈: 674.2227. found: 674.2227.

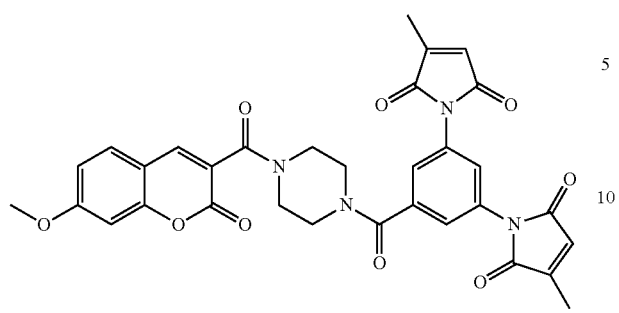

1,1'-(5-(4-(7-methoxy-2-oxo-2H-chromene-3-carbonyl)piperazine-1-carbonyl)-1,3-phenylene)bis(3-methyl-1H-pyrrole-2,5-dione) (YC24)

The synthesis of compound YC24 followed the same protocol as the synthesis of compound YC25, starting with compound 7 to obtain compound YC24 as a white gummy solid (10 mg, 9% yield). $^1$H NMR (400 MHz, CDCl$_3$): δ (ppm) 7.96 (s, 1H), 7.66 (s, 1H), 7.52 (s, 2H), 7.45 (d, J=8.6 Hz, 1H), 6.90 (d, J=8.7 Hz, 1H), 6.84 (s, 1H), 6.51 (s, 1H), 3.90 (s, 3H), 3.86 (br, 4H), 3.67 (br, 2H), 3.47 (br, 2H), 2.19 (s, 6H); $^{13}$C NMR (100 MHz, CDCl$_3$): δ (ppm) 169.9, 168.7, 168.5, 164.1, 158.4, 156.4, 146.1, 136.1, 132.6, 129.8, 127.7, 123.0, 122.8, 120.6, 113.5, 111.9, 100.6, 56.0, 29.7, 11.2.

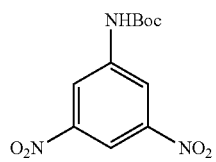

tert-butyl(3,5-dinitrophenyl)carbamate (10)

To a solution of 3,5-dinitroaniline (9) (1.1 g, 6 mmol) in THF (30 mL) was added Boc$_2$O (3.92 g, 18 mmol), DMAP (0.005 g, cat) and Et$_3$N (2.1 mL, 15 mmol); this reaction mixture was heated to reflux for 1 h. The mixture was evaporated to remove the solvents, and the residue was dissolved in Et$_2$O, washed with 1N HCl (aq), NaHCO$_3$ and brine, dried and concentrated to obtain a white solid. The solid obtained was re-dissolved in methanol, and the solution formed was treated with K$_2$CO$_3$ (2.48 g, 18 mmol). This mixture was heated to reflux for 1 h, and concentrated to dryness. The residue was partitioned between ethyl acetate and H$_2$O, and the aqueous layer was extracted with ethyl acetate twice. The combined organic layers were washed with 1N HCl and brine, dried over MgSO$_4$ and concentrated under vacuum to obtain compound 10 as a beige solid (1.56 g, 92% yield). m.p. 162.5-164.3° C.; $^1$H NMR (400M, CDCl$_3$): δ (ppm) 8.68 (t, J=2.0 Hz, 1H), 8.64 (d, J=1.9 Hz, 2H), 7.07 (s, 1H), 1.56 (s, 3H); $^{13}$C NMR (100M, CDCl$_3$): δ (ppm) 151.9, 149.0, 141.2, 117.8, 112.5, 83.1, 28.3; LRMS (EI) m/z (%): 283.1 (M$^+$, 0.7%); HRMS (EI): calcd for C$_{11}$H$_{13}$N$_3$O$_6$: 283.0804. found: 283.0793.

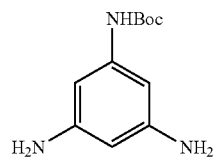

tert-butyl(3,5-diaminophenyl)carbamate (11)

tert-butyl(3,5-dinitrophenyl)carbamate (10) (2.09 g, 8 mmol) was dissolved in MeOH/THF (20 mL/30 mL), Pd/C (200 mg) was added to the solution and the mixture was stirred under H$_2$ overnight. The Pd/C was removed by filtering through celite, and the filtrate was evaporated to dryness. The residue was purified by column chromatography to yield compound 11 as a colourless oil (1.78 g, 100% yield). $^1$H NMR (400 MHz, CDCl$_3$): δ (ppm) 6.41 (br, 1H), 6.18 (s, 2H), 5.73 (m, 1H), 3.56 (br, 4H), 1.48 (s, 9H).

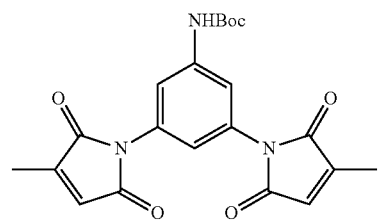

tert-Butyl N-3,5-di-(2-methylmaleimido)phenylcarbamate (12)

Citraconic anhydride (617 µL, 6.87 mmol) was added to a solution of 11 (510 mg, 2.29 mmol) in CHCl$_3$ (9 mL) and the resulting mixture was stirred at 25° C. for 3 h, after which volatiles were evaporated under reduced pressure. The crude mixture was suspended in Et$_2$O and filtered under reduced pressure giving the dimaleamic acid as a beige solid (800 mg, 80% yield) that was used in the next step without further purification. The dimaleamic acid (800 mg) and ZnCl$_2$ (748 mg, 5.5 mmol) were dissolved in toluene-DMF (90:10 mL) before a dilute solution of HMDS (1.72 mL, 8.25 mmol) in toluene (5 mL) was added over 20 min. The resulting mixture was then heated to reflux for 3 h after which the volatiles were evaporated under reduced pressure. The resulting residue was dissolved in EtOAc and washed successively with 0.1 M HCl and saturated Na$_2$CO$_3$. The crude product was then purified by flash chromatography on silica gel (hexane/EtOAc 6:4) giving 12 as an off-white solid (660 mg, 70% yield). $^1$H NMR (400M, CDCl$_3$): δ (ppm) 7.45 (s, 2H), 7.26 (m, 1H), 7.15 (m, 1H), 6.65 (br, 1H), 6.46 (m, 2H), 2.15 (s, 6H), 1.49 (s, 9H).

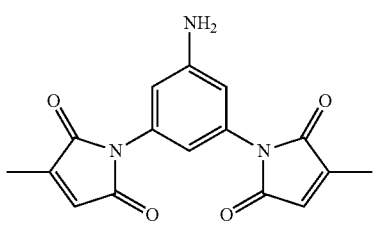

1,1'-(5-amino-1,3-phenylene)bis(3-methyl-1H-pyrrole-2,5-dione) (13)

A solution of 12 (2.02 g, 4.9 mmol) in $CH_2Cl_2$ (49 mL) was treated with TFA (49 mL) at 25° C. for 2 h, after which the volatiles were evaporated. The residue was purified by a silica gel flash column chromatography to yield compound 13 as beige solid (1.85 g, 88% yield).

Spectral data obtained for the characterization of compounds 11 to 13 were the same as those reported previously by our group (Keillor, J. W. et al., Org Biomol Chem 2011, 9, 185-197).

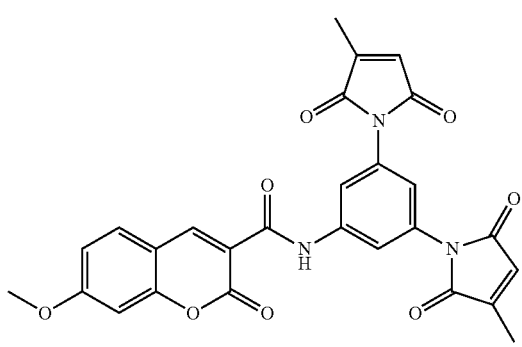

N-(3,5-bis(3-methyl-2,5-dioxo-2,5-dihydro-1H-pyrrol-1-yl)phenyl)-7-methoxy-2-oxo-2H-chromene-3-carboxamide (YC26)

To a solution of compounds 13 (42 mg, 0.1 mmol) and 2 (22 mg, 0.12 mmol) in DMF (1 mL) were added TBTU (48 mg, 0.15 mmol) and DIPEA (35 µL, 0.2 mmol); the resulting solution was stirred at ambient temperature overnight. $CH_2Cl_2$ was then added to the reaction, and the mixture was washed with dilute HCl, $H_2O$ and brine, then dried and concentrated. The residue was purified by a silica gel column chromatography to obtain YC26 as a solid (7 mg, 14% yield). $^1$H NMR (400M, $CDCl_3$): δ 10.97 (s, 1H), 8.94 (s, 1H), 7.84 (d, J=1.8 Hz, 2H), 7.63 (d, J=8.8 Hz, 1H), 6.98 (dd, J=8.7, 2.4 Hz, 1H), 6.91 (d, J=2.3 Hz, 1H), 6.69 (d, J=1.8 Hz, 1H), 6.50 (s, 2H), 3.94 (s, 3H), 2.18 (s, 6H); LRMS (EI) m/z (%): 513.1 (M$^+$, 3%); HRMS (EI): calcd for $C_{27}H_{19}N_3O_8$: 513.1172. found: 513.1179.

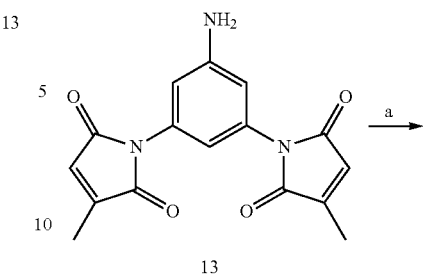

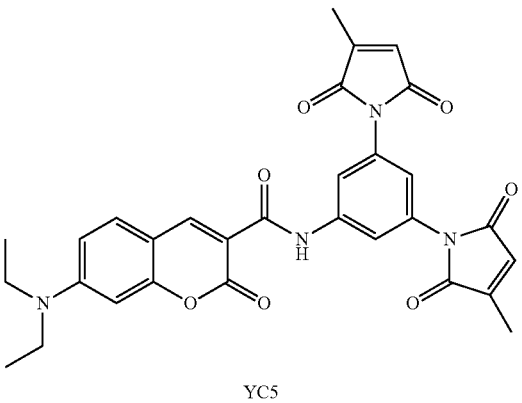

(a) TBTU, DIPEA, DMF, r.t overnight

N-(3,5-bis(3-methyl-2,5-dioxo-2,5-dihydro-1H-pyrrol-1-yl)phenyl)-7-(diethylamino)-2-oxo-2H-chromene-3-carboxamide (YC5)

To a solution of 7-(diethylamino)coumarin-3-carboxylic acid (31 mg, 0.12 mmol) and 13 in anhydrous DMF (1 mL) were added TBTU and DIPEA. The resulting mixture was stirred overnight at room temperature under $N_2$. The reaction mixture was diluted with $CH_2Cl_2$, washed with 0.1 N HCl, $H_2O$ and saturated $NaHCO_3$, and the organic phase was dried over $MgSO_4$ and concentrated. The residue was purified by silica gel chromatography to afford YC5 as a yellow solid (28 mg, 50% yield). $^1$H NMR (400 MHz, CDCl3): δ (ppm) 11.04 (s, 1H), 7.84 (d, J=1.8 Hz, 2H), 7.44 (d, J=8.9 Hz, 1H), 7.22 (d, J=1.8 Hz, 1H), 6.66 (dd, J=8.9 Hz, 2.3 Hz, 1H), 6.52 (d, J=2.2 Hz, 1H), 6.49 (d, J=1.8 Hz, 2H), 3.46 (q, J=7.1 Hz, 4H), 1.25 (t, J=7.1 Hz, 6H); 13C NMR (100 MHz, $CDCl_3$): δ (ppm) 170.0897, 168.9923, 163.0100, 161.2967, 157.8373, 152.9430, 148.7999, 145.8739, 139.3832, 132.5488, 131.4497, 127.5180, 118.0664, 116.3388, 110.2364, 109.6053, 108.5580, 96.6230, 45.1932, 12.4344. LRMS (EI) m/z (%): 554.2, (M$^+$, 100%); HRMS (EI): calculated for $C_{16}H_{13}N_3O_5$: 554.1801. found: 554.1803.

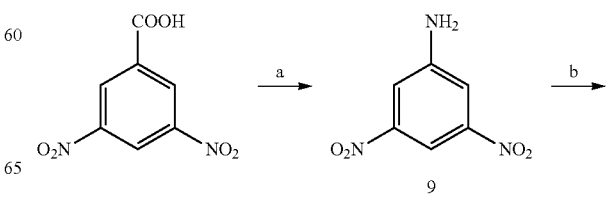

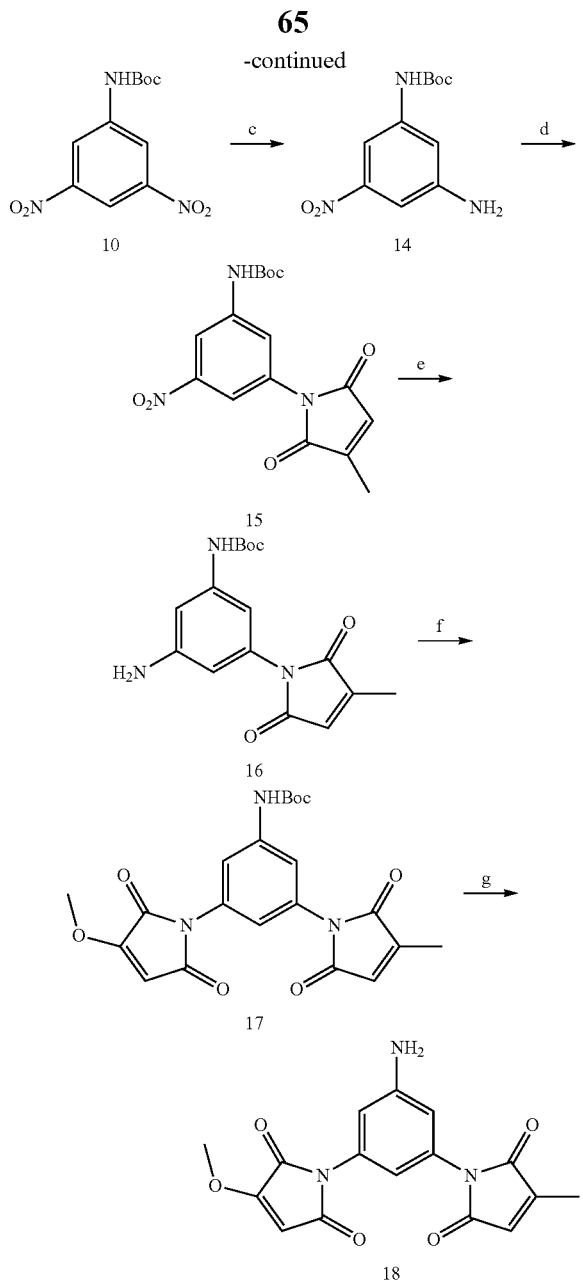

3, 5-Dinitroaniline (9) and methoxymaleic anhydride were synthesized as described (Caron, K. et al., Org. Biomol. Chem. 2011, 9, 185-197; Sahoo, M. K. et al. Synthesis-Stuttgart 2003, 346-349).

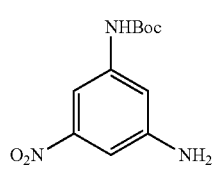

tert-Butyl (3-amino-5-nitrophenyl)carbamate (14)

In a 25-mL three-necked round-bottomed flask equipped with a reflux condenser and a stirrer, a mixture of compound 10 (566 mg, 2 mmol), palladium on carbon (23 mg, 4% w/w, and triethylamine (1.25 mL, 9 mmol) in 8 mL acetonitrile was heated to reflux. A solution of HCOOH (324 µL, 8.6 mmol) in 2 mL acetonitrile was carefully added dropwise over 10 min. The mixture was refluxed for 20 min until the starting material was observed to disappear by TLC. Upon cooling, the reaction mixture was filtered to remove the catalyst and evaporate to dryness. The residue was purified by flash column chromatography to obtain the product. (460 mg, 91% yield). m.p. 144.4-146.7° C.; $^1$H NMR (400 MHz, CDCl3): δ (ppm) 7.42 (s, 1H), 7.16 (s, 1H), 6.64 (s, 1H), 1.52 (s, 9H); $^{13}$C NMR (100 MHz, CDCl$_3$): δ (ppm) 152.4, 149.6, 148.0, 140.2, 109.5, 103.8, 103.2, 81.4, 28.3; LRMS (EI) m/z (%): 253.1 (M$^+$, 41%); HRMS (EI): calcd for C$_{11}$H$_{15}$N$_3$O$_4$: 253.2545. found: 253.1119.

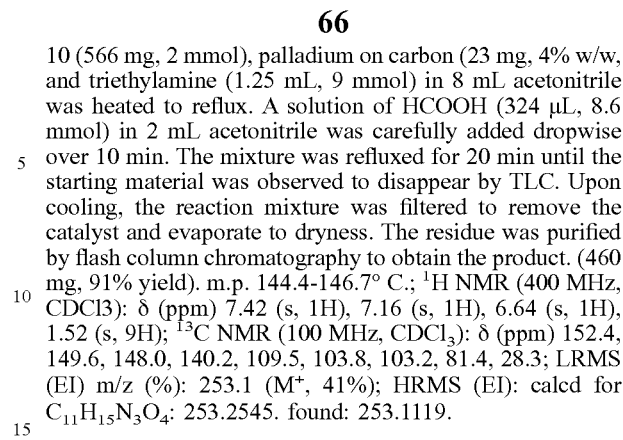

tert-Butyl (3-(3-methyl-2,5-dioxo-2,5-dihydro-1H-pyrrol-1-yl)-5-nitrophenyl)carbamate (15)

Citraconic anhydride (181 µL, 2 mmol) was added to a solution of 14 (340 mg, 1.34 mmol) in CHCl$_3$ (5 mL) and the resulting mixture was stirred at 25° C. for 3 h after which volatiles were evaporated under reduced pressure. The crude was suspended with Et$_2$O and filtered under reduced pressure leading to the maleamide as a beige solid that was used in the next step without further purification. The maleamide and ZnCl$_2$ (273 mg, 2.01 mmol) were dissolved in toluene-DMF (60:5 mL) before a dilute solution of HMDS (700 µL, 3.35 mmol) in toluene (7 mL) was added over 20 min. The resulting mixture was then heated to reflux for 2 h after which the volatiles were evaporated under reduced pressure. The resulting residue was dissolved in EtOAc and washed successively with 0.1 M HCl and saturated Na$_2$CO$_3$. The crude product was then purified by flash chromatography on silica gel (hexane/EtOAc 6:4) giving 15 as an off-white solid (379 mg, 82% yield). $^1$H NMR (400 MHz, CDCl3): δ (ppm) 8.23 (s, 1H), 9.90 (s, 1H), 7.81 (s, 1H), 7.11 (s, 1H), 6.50 (s, 1H), 2.15 (s, 3H), 1.48 (s, 9H); $^{13}$C NMR (100 MHz, CDCl$_3$): δ (ppm) 169.8, 168.7, 152.2, 148.8, 146.3, 140.3, 133.1, 127.7, 120.4, 114.4, 111.7, 81.9, 28.2, 11.2; LRMS (EI) m/z (%): 347.11 (M$^+$, 2.2%); HRMS (EI): calcd for C$_{16}$H$_{17}$N$_4$O$_6$: 347.1117. found: 347.1130.

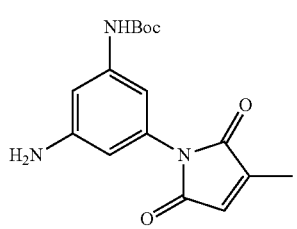

tert-Butyl (3-amino-5-(3-methyl-2,5-dioxo-2,5-dihydro-1H-pyrrol-1-yl)phenyl)carbamate (16)

Compound 15 (76 mg, 0.22 mmol) was dissolved in EtOH (1 mL), SnCl$_2$ (166 mg, 0.88 mmol) was added and the mixture was heated to 70° C. for 1 h. After cooling down to room temperature, the reaction mixture was diluted by ethyl acetate, washed with NaHCO$_3$ (aq), H$_2$O and brine, dried with MgSO$_4$ and concentrated. The residue was purified with flash column chromatography to obtain compound 16 as brown oil. (55 mg, 80% yield) $^1$H NMR (400 MHz, CDCl$_3$): δ (ppm) 6.82 (s, 1H), 6.76 (s, 1H), 6.70 (s, 1H), 6.42 (s, 1H), 6.29 (s, 1H), 2.12 (s, 3H), 1.44 (s, 9H); $^{13}$C NMR (100 MHz, CDCl3): δ (ppm) 170.6, 169.6, 152.6, 147.8, 145.7, 139.9, 127.4, 107.4, 106.2, 104.3, 80.5, 28.3, 11.1; LRMS (D) m/z (%): 317.1 (M$^+$, 16.3%); HRMS (D): calcd for C$_{16}$H$_{19}$N$_4$O$_4$: 317.1376. found: 317.1364.

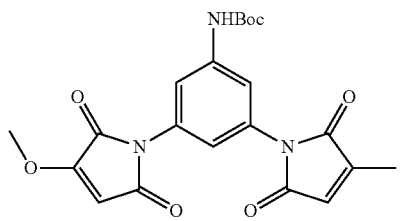

17 tert-Butyl (3-(3-methoxy-2,5-dioxo-2,5-dihydro-1H-pyrrol-1-yl)-5-(3-methyl-2,5-dioxo-2,5-dihydro-1H-pyrrol-1-yl)phenyl)carbamate (17)

Methoxymaleic anhydride (389 mg, 3.03 mmol) was added to a solution of 16 (642 mg, 2.02 mmol) in CHCl$_3$ (8 mL) and the resulting mixture was stirred at 25° C. for 3 h after which volatiles were evaporated under reduced pressure. The crude mixture was suspended with Et$_2$O and filtered under reduced pressure leading to the maleamide as a beige solid that was used in the next step without further purification. The maleamide and ZnCl$_2$ (412 mg, 3.03 mmol) were dissolved in toluene-DMF (80:10 mL) before a dilute solution of HMDS (1.06 mL, 5.06 mmol) in toluene (20 mL) was added over 20 min. The resulting mixture was then heated to reflux for 2 h after which the volatiles were evaporated under reduced pressure. The resulting residue was dissolved in EtOAc and washed successively with 0.1 M HCl and saturated Na$_2$CO$_3$ (aq). The crude product was then purified by flash chromatography on silica gel (Hexane/ EtOAc 5:5) giving 17 as an off-white solid (862 mg, 100% yield). m.p. 141.0-142.3° C.; $^1$H NMR (400 MHz, CDCl$_3$): δ (ppm) 7.45 (s, 1H), 7.38 (s, 1H), 7.09 (s, 1H), 6.87 (s, 1H), 6.42 (s, 1H), 5.52 (s, 1H), 3.94 (s, 3H), 2.15 (s, 3H), 1.37 (s, 9H); $^{13}$C NMR (100 MHz, CDCl$_3$): δ (ppm) 170.8, 170.1, 169.0, 168.5, 163.9, 160.7, 152.4, 145.9, 139.6, 132.6, 132.1, 127.5, 116.9, 114.4, 99.4, 96.6, 81.1, 59.2, 28.3, 11.1; LRMS (D) m/z (%): 427.1 (M$^+$, 2.4%); HRMS (D): calcd for C$_{21}$H$_{21}$N$_3$O$_7$: 427.1380. found: 427.1353.

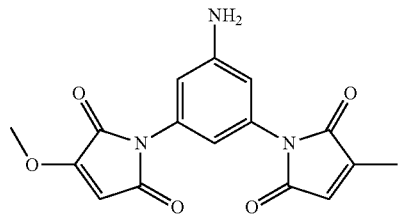

18

1-(3-Amino-5-(3-methoxy-2,5-dioxo-2,5-dihydro-1H-pyrrol-1-yl)phenyl)-3-methyl-1H-pyrrole-2,5-dione (18)

A solution of 17 (862 mg, 2.02 mmol) in CH$_2$Cl$_2$ (10 mL) was treated with TFA (10 mL) at 25° C. for 2 h, after which the volatiles were evaporated. The residue was purified by a silica gel flash column chromatography to yield compound 18 as beige solid (682 mg, 100% yield). m.p. 76-77° C.; $^1$H NMR (400 MHz, CDCl$_3$): δ (ppm) 6.73 (s, 1H), 6.59 (s, 2H), 6.49 (s, 1H), 5.98 (s, 1H) 3.98 (s, 3H), 2.04 (s, 3H); $^{13}$C NMR (100 MHz, CDCl$_3$): δ (ppm) 170.8, 169.9, 169.5, 164.5, 161.3, 164.5, 161.3, 146.2, 133.1, 132.6, 127.9, 113.8, 112.8, 97.6, 95.8, 11.3; LRMS (EI) m/z (%): 327.1 (M$^+$, 100%); HRMS (EI): calcd for C$_{16}$H$_{13}$N$_3$O$_5$: 327.0855. found: 327.0836.

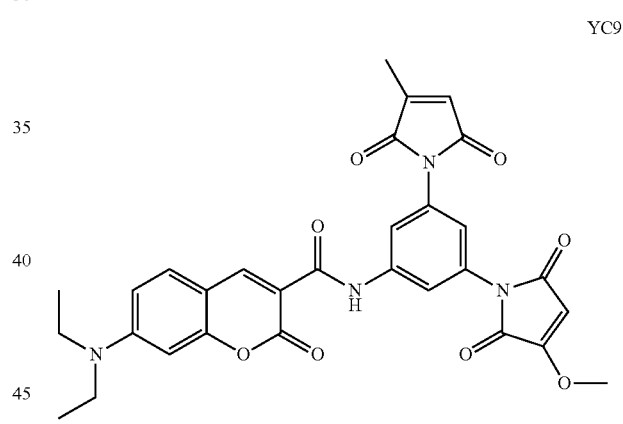

YC9

7-(Diethylamino)-N-(3-(3-methoxy-2,5-dioxo-2,5-dihydro-1H-pyrrol-1-yl)-5-(3-methyl-2,5-dioxo-2,5-dihydro-1H-pyrrol-1-yl)phenyl)-2-oxo-2H-chromene-3-carboxamide (YC9)

7-(Diethylamino)coumarin-3-carboxylic acid (48 mg, 0.184 mmol) was dissolved in 1,2-dichloroethane (2 mL), and phosphorus oxychloride (52 μL, 0.55 mmol) was added. The mixture was refluxed at 94° C. for 4 hours under an argon atmosphere, then cooled to room temperature. The solvent was removed under reduced pressure to afford the acid chloride. The residue was dissolved in CH$_3$CN (2 mL), and 18 (60 mg, 0.184 mmol) was added. The mixture was stirred at room temperature overnight under an argon atmosphere. The reaction mixture was evaporated to dryness. The residue was purified by silica gel chromatography to afford YC9 as a yellow solid (54 mg, 56% yield). m.p. 88.3-93.7° C.; $^1$H NMR (400 MHz, CDCl3): δ (ppm) 11.0 (s, 1H), 8.75 (s, 1H), 7.86 (s, 1H), 7.81 (s, 1H), 7.45 (d, J=9.0 Hz, 1H), 7.22 (s, 1H), 7.66 (d, J=7.8 Hz, 1H), 6.52 (s, 1H), 6.49 (s, 1H), 5.58 (s, 1H), 4.01 (s, 3H), 3.46 (q, J=6.6 Hz, 4H), 2.2 (s, 3H), 1.25 (t, J=6.6 Hz, 6H); $^{13}$C NMR (100 MHz, CDC$_{13}$): δ (ppm) 170.1, 168.9, 168.3, 163.0, 160.7, 157.8, 152.9, 148.8, 145.9, 139.4, 132.6, 131.4, 127.5, 118.2, 116.5, 110.2, 109.7, 108.6, 96.6, 59.1, 45.2, 12.4, 11.2; LRMS (EI) m/z (%): 570.4 (M$^+$, 0.2).

Synthesis of YC9M

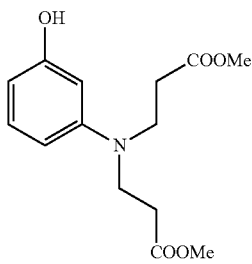

Dimethyl 3,3'-((3-hydroxyphenyl)azanediyl)dipropanoate (19)

Compound 19 was prepared in two steps. The first step was carried out according to a literature procedure[46]. 3-Aminophenol (3.18 g, 29 mmol) and acrylic acid (6 mL, 87.5 mmol) were mixed in H$_2$O (3 mL), and the resulting mixture was heated to 70° C. for 3 h. The reaction mixture was then cooled to ambient temperature, methanol (300 mL) was added to the mixture, and H$_2$SO$_4$ (1 mL) was added. The resulting mixture was then heated to reflux overnight. The mixture was then cooled down to ambient temperature, and the solvent was evaporated under reduced pressure. The residue was dissolved in EtOAc, washed with NaHCO$_3$ (aq), H$_2$O and brine, dried over Na$_2$SO$_4$, and concentrated. The crude product was purified by flash chromatography (30% EtOAc in hexane) to give compound 19 as a colourless oil [CAS: 59486-18-9] (5.43 g, 67% yield). $^1$H NMR (400 MHz, CDCl$_3$): δ (ppm) 7.07 (t, J=7.64 Hz, 1H), 6.27-6.25 (m, 1H), 6.24-6.21 (m, 2H), 5.62 (s, 1H), 3.68 (s, 6H), 3.62 (t, J=7.4 Hz, 4H), 2.69 (t, J=7.4 Hz, 4H).

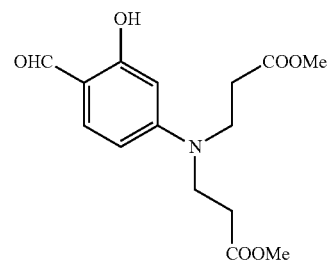

Dimethyl 3,3'-((4-formyl-3-hydroxyphenyl)azanediyl)dipropanoate (20)

An oven dried flask was charged with anhydrous DMF (5 mL) and cooled to 0° C. under argon. Phosphorous oxychloride (0.5 mL, 5.5 mmol) was added slowly to the stirred solution. The mixture was allowed to reach ambient temperature and then heated to 40° C. with stirring for 1 h. The reaction was then removed from the oil bath and kept at ambient temperature. A DMF solution of compound 19 (1.4 g, 5 mmol) was then added dropwise. After the addition was completed, the mixture was heated to 40° C. and stirred overnight. The reaction was allowed to cool down to ambient temperature, then H$_2$O (8 mL) was added before the mixture was heated to 50° C. and stirred for 30 min. After cooling down to ambient temperature, EtOAc was added to the reaction mixture, the solution was washed with H$_2$O and brine, dried over Na$_2$SO$_4$ and concentrated. The residue afforded was further purified by flash chromatography (30% EtOAc in hexane) to afford compound 20 as a yellow oil (725 mg, 47% yield). $^1$H NMR (400 MHz, CDCl$_3$): δ (ppm) 11.54 (s, 1H), 9.54 (s, 1H), 7.32 (d, J=8.8 Hz, 1H), 6.30 (dd, J=8.8, 2.0 Hz, 1H), 6.09 (d, J=1.9 Hz, 1H), 3.73 (t, J=7.3 Hz, 4H), 3.67 (s, 6H), 2.65 (s, J=7.4 Hz, 4H); $^{13}$C NMR (100 MHz, CDCl$_3$): δ (ppm) 192.5 (CH), 171.60, 164.0, 153.3, 135.4 (CH), 112.6, 104.4 (CH), 97.4 (CH), 51.7 (CH), 46.5 (CH$_2$), 31.9 (CH$_2$); LRMS (EI) m/z (%): 309.1 (M$^+$, 18), 236.1 (100); HRMS (EI): calcd for C$_{15}$H$_{19}$NO$_6$: 309.1212. found: 309.1203.

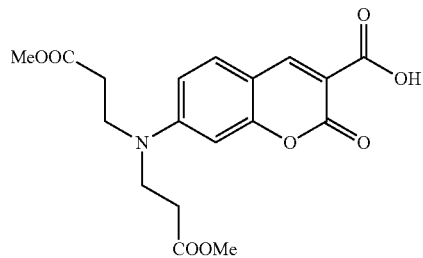

7-(Bis(3-methoxy-3-oxopropyl)amino)-2-oxo-2H-chromene-3-carboxylic acid (21)

Compound 21 was synthesized according to a literature procedure[42]. Compound 20 (184 mg, 0.6 mmol) and malonic acid (124 mg, 1.2 mmol) were dissolved in anhydrous pyridine (0.6 mL) in a round-bottomed flask, and aniline (50 μL, 0.54 mmol) was added dropwise. The mixture was stirred overnight at ambient temperature under an argon atmosphere. The resulting precipitate was washed with ethanol (1.5 mL) for 1 h, and then filtered. The obtained solid was washed again with 0.1 M HCl, H$_2$O and Et$_2$O, and dried under vacuum to afford compound 21 as a solid (85 mg, 38% yield). m.p. 184.0-186.1° C.; $^1$H NMR (400 MHz, acetone-d6): δ (ppm) 8.73 (s, 1H), 7.78 (d, J=9.0 Hz, 1H), 7.02 (dd, J=9.0, 2.5 Hz, 1H), 6.78 (d, J=2.4 Hz, 1H), 3.93 (t, J=7.1 Hz, 4H), 3.65 (s, 6H), 2.77 (t, J=7.2 Hz, 4H); $^{13}$C NMR (100 MHz, acetone-d6): δ (ppm) 171.5, 167.2, 164.9, 163.2, 157.8, 153.6, 150.2 (CH), 132.2 (CH), 111.3 (CH), 109.1, 107.5, 97.4 (CH), 51.0 (CH$_2$), 46.7 (CH$_2$), 31.4 (CH$_2$);

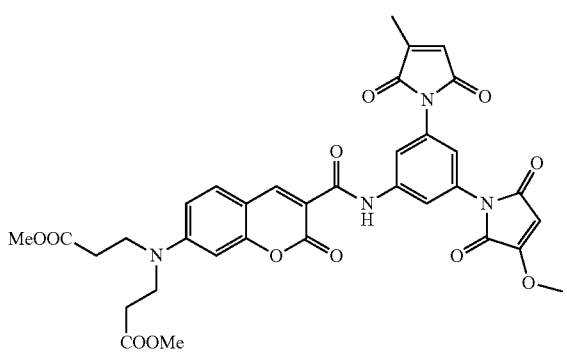

YC9M

Dimethyl 3,3'-((3-((3-(3-methoxy-2,5-dioxo-2,5-dihydro-1H-pyrrol-1-yl)-5-(3-methyl-2,5-dioxo-2,5-dihydro-1H-pyrrol-1-yl)phenyl)carbamoyl)-2-oxo-2H-chromen-7-yl)azanediyl)dipropanoate (YC9M)

The synthesis of YC9M follows the same protocol for the synthesis of YC9, starting with compounds 21 and 18. (42 mg, 38% yield) $^1$H NMR (CDCl_3, 400 MHz) δ (ppm): 10.99 (s, 1H), 8.8 (s, 1H), 7.82 (t, J=1.7 Hz, 1H), 7.81 (t, J=1.8 Hz, 1H), 7.51 (d, J=8.9 Hz, 1H), 7.24 (t, J=1.7 Hz, 1H), 6.71 (dd, J=8.9, 2.2 Hz, 1H), 6.57 (d, J=2.0 Hz, 1H), 6.49 (d, J=1.8 Hz, 1H), 5.59 (s, 1H), 4.00 (s, 3H), 3.79 (t, J=7.0 Hz, 4H), 3.72 (s, 3H), 2.66 (t, J=7.0 Hz, 4H), 2.18 (s, 3H); $^{13}$C NMR (100 MHz, CDCl_3): δ (ppm) 171.6, 170.1, 168.9, 162.6, 160.7, 157.5, 152.1, 148.9, 145.9, 139.2, 132.0, 131.6, 127.5, 118.4, 116.5, 111.3, 110.5, 109.4, 97.6, 96.6, 59.2, 52.1, 47.0, 31.9, 11.2; LRMS (ESI) m/z (%): 685.09 ([M−H]−).

Synthesis of YC15-YC19.

3-Bromo-1-phenyl-1H-pyrrole-2,5-dione (23), 3-ethoxy-1-phenyl-1H-pyrrole-2,5-dione (24), 2-ethoxy-4-oxo-4-(phenylamino)but-2-enoic acid (26) and 3-ethoxyfuran-2,5-dione (28) were synthesized as described (Sahoo, M. K. et al., Synthesis-Stuttgart 2003, 346-349).

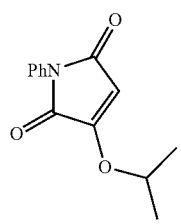

3-isopropoxy-1-phenyl-1H-pyrrole-2,5-dione (25)

To a suspension of 3-bromo-1-phenyl-1H-pyrrole-2,5-dione (23) (253 mg, 1 mmol) in isopropyl alcohol (4 mL), was added triethylamine (500 μL, 3.6 mmol). The mixture formed was heated to reflux and stirred for 1 h. The reaction was cooled down and the solvents were removed by evaporation. The residue was purified by column chromatography to obtain compound 25 as a yellow oil (20 mg, 9% yield). $^1$H NMR (400 MHz, CDCl_3): δ (ppm) 7.45 (m, 2H), 7.31 (m, 3H), 5.45 (s, 1H), 4.51 (m, 1H), 1.46 (s, 3H), 1.44 (s, 3H); $^{13}$C NMR (100 MHz, CDCl_3): δ (ppm) 169.6, 158.9, 131.3, 129.0, 128.8, 127.7, 127.2, 126.4, 126.1; LRMS (EI) m/z (%): 231.1 (M+, 63%); HRMS (EI): calcd for $C_{13}H_{13}NO_3$: 231.0895. found: 231.0888.

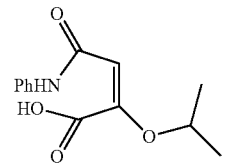

2-isopropoxy-4-oxo-4-(phenylamino)but-2-enoic acid (27)

KOH (300 mg, 5.4 mmol) in $H_2O$ (7.2 mL) was added to a solution of 25 (825 mg, 3.6 mL) in isopropyl alcohol (7.2 mL), and the mixture formed was stirred at ambient temperature for 1 h. After the starting material was totally consumed, the organic solvents were evaporated. The residue was acidified with concentrated HCl at 0° C. The precipitate was filtered out and dried as product 27 (679 mg, 76% yield). The product was used in next steps without further purification.

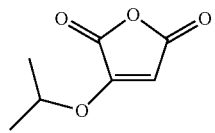

3-isopropoxyfuran-2,5-dione (29)

2-isopropoxy-4-oxo-4-(phenylamino)but-2-enoic acid (27) (679 mg, 2.73 mmol) was heated at 80° C. in a mixture of HOAc and $Ac_2O$ (1:1, 18 mL) for 4 h. $Ac_2O$ and HOAc were distilled off in vacuo and the residue was purified by silica gel column chromatography to obtain 29 (400 mg, 94%) as a colourless oil. $^1$H NMR (400 MHz, CDCl_3): δ (ppm) 5.62 (s, 1H), 4.51 (m, 1H), 1.46 (s, 3H), 1.43 (s, 3H); $^{13}$C NMR (100 MHz, CDCl_3): δ (ppm) 129.8, 128.7, 126.1, 97.9, 78.6, 27.0, 21.2; LRMS (EI) m/z (%): 156.0 (M+, 1%).

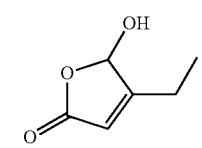

4-ethyl-5-hydroxyfuran-2(5H)-one (30)

(Parsons, W. H. et al., J Am Chem Soc 2013, 135 10582-10585) Solid morpholine hydrochloride (3.4 g, 27.5 mmol) was added to a solution of glyoxylic acid monohydrate (2.3 g, 25 mmol) in 20 mL of dioxane. To this suspension was added dropwise 3 mL of $H_2O$, after which all the solid material was dissolved. A solution of butyraldehyde (2.36 mL, 26.25 mmol) in 5 mL dioxiane was added via syringe and the colourless solution was stirred at ambient temperature for 3 h, then heated to 100° C. and stirred overnight. The reaction mixture was evaporated, extracted 3 times with Et$_2$O, and the combined organic layers were then washed with saturated NaHCO$_3$ (aq) and brine, dried over MgSO$_4$ and concentrated. The residue was purified with column chromatography to obtain compound 30 (850 mg, 27%). $^1$H NMR (400 MHz, CDCl$_3$): δ (ppm) 6.00 (s, 1H), 5.83 (s, 1H), 2.48 (m, 1H), 2.33 (m, 1H), 1.20 (t, J=7.4 Hz, 3H); $^{13}$C NMR (100 MHz, CDCl$_3$): δ (ppm) 171.3, 116.8, 100.0, 99.0, 21.0, 10.9; LRMS (EI) m/z (%): 127.0 ([M−H]−, 13.4%); HRMS (EI): calcd for C$_6$H$_7$O$_3$: 127.0401. found: 127.0377.

Synthesis of YC15-YC19.

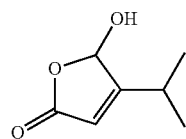

5-hydroxy-4-isopropylfuran-2(5H)-one (31)

The above reaction was carried out with 3-methylbutanal, affording 31 (983 mg, 28% yield). $^1$H NMR (400 MHz, CDCl$_3$): δ (ppm) 6.07 (s, 1H), 5.79 (s, 1H), 2.72 (m, 1H), 1.19 (d, J=6.8 Hz, 3H), 1.17 (d, J=7.0 Hz, 3H); $^{13}$C NMR (100 MHz, CDCl$_3$): δ (ppm) 171.3, 116.2, 98.3, 25.5, 22.4; LRMS (EI) m/z (%): 142.09 (M+, 49.3%); HRMS (EI): calcd for C$_7$H$_{10}$O$_3$: 142.0630. found: 142.0883.

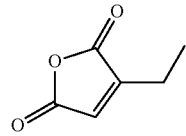

3-ethylfuran-2,5-dione (32)

Dess-Martin periodinane was suspended in anhydrous dichloromethane and stirred at room temperature for 10 min before the solution of compound 30 in dichloromethane was added. The mixture formed was stirred at room temperature for 2.5 h. The reaction mixture was washed with saturated Na$_2$S$_2$O$_3$ (aq) and brine. The organic layer was dried over MgSO4 and concentrated. The residue was purified by column chromatography (413 mg, 49%). $^1$H NMR (400 MHz, CDCl$_3$): δ (ppm) 6.60 (t, J=2.0 Hz, 1H), 2.57 (qd, J=7.4, 2.0 Hz, 2H), 1.28 (t, J=7.4 Hz, 3H); $^{13}$C NMR (100 MHz, CDCl$_3$): δ (ppm) 165.7, 163.9936, 155.1, 128.0, 19.6, 11.0; LRMS (EI) m/z (%): 126.0 (M+, 14.6%); HRMS (EI): calcd for C$_7$H$_{10}$O$_3$: 126.0317. found: 126.0311.

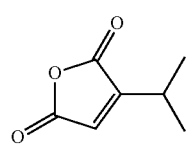

3-isopropylfuran-2,5-dione (33)

The above reaction was carried out starting with 5-hydroxy-4-isopropylfuran-2(5H)-one (31) afforded 33 (324 mg, 33% yield). $^1$H NMR (400 MHz, CDCl$_3$): δ (ppm) 6.44 (d, J=1.6 Hz, 1H), 2.9 (m, 1H), 1.29 (s, 3H), 1.27 (s, 3H); $^{13}$C NMR (100 MHz, CDCl$_3$): δ (ppm) 165.2, 163.9, 127.0, 26.6, 23.5, 20.5; LRMS (EI) m/z (%): 140.04 (M+, 5.2%); HRMS (EI): calcd for C$_7$H$_8$O$_3$: 140.0473. found: 102.0462.

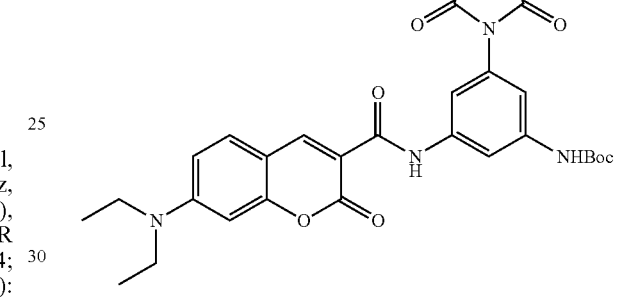

tert-butyl (3-(7-(diethylamino)-2-oxo-2H-chromene-3-carboxamido)-5-(3-methyl-2,5-dioxo-2,5-dihydro-1H-pyrrol-1-yl)phenyl)carbamate (34)

7-(Diethylamino)coumarin-3-carboxylic acid (196 mg, 0.75 mmol) was dissolved in 1,2-dichloroethane (7.5 mL), and phosphorus oxychloride (210 μL, 2.25 mmol) was added. The mixture was heated to reflux at 94° C. for 4 h under an argon atmosphere, then cooled to room temperature. The solvent was removed under reduced pressure to afford the acid chloride. The residue was dissolved in CH$_3$CN (7.5 mL), and tert-butyl (3-amino-5-(3-methyl-2,5-dioxo-2,5-dihydro-1H-pyrrol-1-yl)phenyl)carbamate (238 mg, 0.75 mmol) was added. The mixture was stirred at room temperature overnight under an argon atmosphere. The reaction mixture was then evaporated to dryness. The residue was purified by silica gel chromatography to afford compound 34 as a yellow solid (345 mg, 82% yield). $^1$H NMR (400 MHz, CDCl$_3$): δ (ppm) 10.87 (s, 1H), 8.61 (s, 1H), 7.82 (s, 1H), 7.22 (m, 4H), 6.55 (d, J=7.5 Hz, 1H), 6.40 (d, J=6.0 Hz, 2H), 3.33 (q, J=7.0 Hz, 4H), 2.05 (s, 3H), 1.34 (s, 9H), 1.14 (t, J=6.9 Hz, 6H); $^{13}$C NMR (100 MHz, CDCl$_3$): δ (ppm) 170.4, 169.3, 162.9, 161.2, 157.7, 152.6, 148.6, 145.8, 139.9, 139.2, 132.5, 131.4, 127.4, 112.4, 111.9, 110.2, 109.4, 109.3, 108.4, 96.4, 80.5, 45.1, 28.3, 12.4, 11.1; LRMS (ESI) m/z (%): 583.1 ([M+Na]+); HRMS (ESI): calcd for C$_{30}$H$_{32}$N$_4$NaO$_7$: 583.2169. found: 583.2078.

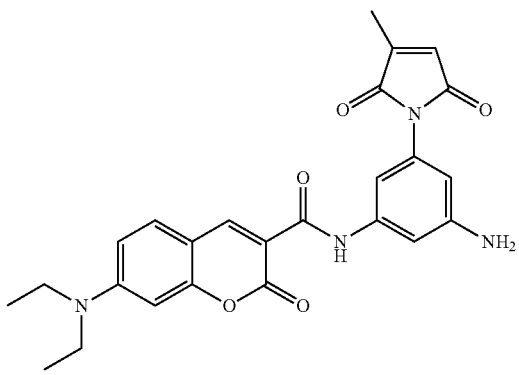

N-(3-amino-5-(3-methyl-2,5-dioxo-2,5-dihydro-1H-pyrrol-1-yl)phenyl)-7-(diethylamino)-2-oxo-2H-chromene-3-carboxamide (35)

A solution of 34 (340 mg, 0.61 mmol) in $CH_2Cl_2$ (6 mL) was treated with TFA (6 mL) at 25° C. for 3 h after which the volatiles were evaporated. The residue was purified by a silica gel flash column chromatography to yield compound 35 as yellow solid (265 mg, 95% yield). $^1$H NMR (400 MHz, DMSO): δ (ppm) 10.67 (s, 1H), 8.69 (s, 1H), 7.70 (d, J=9.1 Hz, 1H), 7.11 (s, 1H), 6.88 (s, 1H), 6.82 (dd, J=9.1, 2.2 Hz, 1H), 6.73 (q, J=1.8 Hz, 1H), 6.63 (d, J=1.1 Hz, 1H), 3.46 (q, J=7.0 Hz, 4H), 2.03 (s, 3H), 1.13 (t, J=7.0 Hz, 6H); $^{13}$C NMR (100 MHz, DMSO): δ (ppm) 170.9, 170.1, 162.8, 161.0, 157.8, 153.3, 148.6, 146.1, 139.6, 133.3, 132.3, 127.9, 110.9, 109.6, 108.4, 100.0, 96.4, 44.9, 12.8, 11.3; LRMS (ESI) m/z (%): 483.1 ([M+Na]$^+$); HRMS (ESI): calcd for $C_{25}H_{24}N_4NaO_5$: 483.1644. found: 483.1643.

General Procedures for Maleimide Formation.

Maleic anhydride compound 28, 29, 32, 33 or bromomaleic anhydride (1.0-1.5 eq) was added to a solution of 35 (1.0 eq) in acetone and the resulting mixture was stirred at 25° C. for 4 h, after which volatiles were evaporated under reduced pressure. The crude mixture was suspended with $Et_2O$ and filtered under reduced pressure leading to the dimaleamic acid as a yellow solid that was used in the next step without further purification. The dimaleamic acid and $ZnCl_2$ (1.5 eq) were dissolved in toluene-DMF (90:10) before a dilute solution of HMDS (2.5 eq) in toluene was added over 20 min. The resulting mixture was then heated to reflux for 3 h after which the volatiles were removed under reduced pressure. The resulting residue was dissolved in EtOAc and washed successively with 0.1 M HCl and saturated $Na_2CO_3$ (aq). The crude product was then purified by flash chromatography on silica gel giving compound YC15-YC19 in 35% to 62% yield.

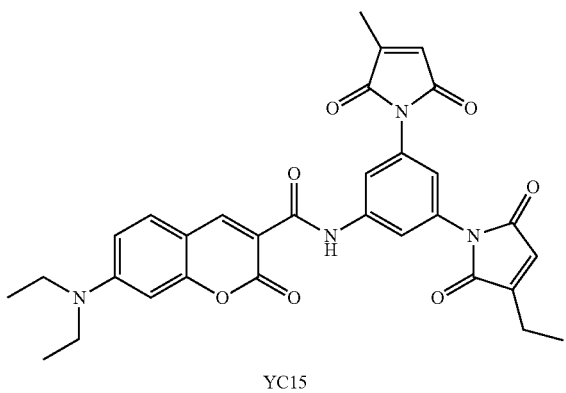 [SMILES: CCC1=CC(=O)N(c2cc(NC(=O)c3cc4ccc(N(CC)CC)cc4oc3=O)cc(N3C(=O)C=C(C)C3=O)c2)C1=O ; "YC15"]

YC15

The compound YC15 was synthesized according to the general procedure starting with 32 (1.5 equiv) in 50% yield. $^1$H NMR (400 MHz, CDCl$_3$): δ (ppm) 10.99 (s, 1H), 8.69 (s, 1H), 7.78 (d, J=1.8 Hz, 2H), 7.39 (d, J=9.0 Hz, 1H), 7.20 (t, J=1.8 Hz, 1H), 6.62 (dd, J=9.0, 2.4 Hz, 1H), 6.46 (m, 2H), 6.41 (t, J=1.9 Hz, 1H), 3.40 (q, J=7.2 Hz, 4H), 2.52 (dd, J=7.4, 1.9 Hz, 2H), 2.13 (s, 3H), 1.24 (t, J=7.4 Hz, 3H), 1.19 (t, J=7.2 Hz, 6H); $^{13}$C NMR (100 MHz, CDCl$_3$): δ (ppm) 170.1, 169.8, 169.1, 169.0, 163.0, 161.3, 157.8, 151.8, 148.7, 145.9, 139.4, 132.6, 131.4, 125.9, 118.1, 116.3, 116.3, 110.3, 109.5, 108.6, 96.6, 45.2, 19.1, 12.4, 11.3, 11.2; LRMS (ESI) m/z (%): 591.2 ([M+Na]$^+$); HRMS (ESI): calcd for $C_{31}H_{28}N_4NaO_7$: 591.1865. found: 591.1835.

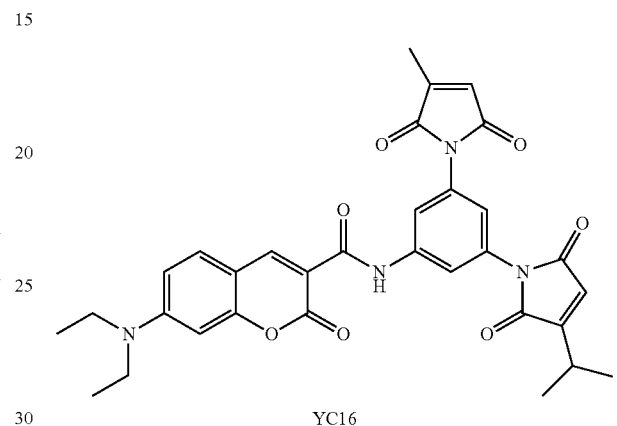

YC16

The compound YC16 was synthesized according to the general procedure starting with 33 (1.5 equiv) in 62% yield. $^1$H NMR (400 MHz, CDCl$_3$): δ (ppm) 11.04 (s, 1H), 8.76 (s, 1H), 7.83 (m, 2H), 7.45 (d, J=9.0 Hz, 1H), 7.23 (t, J=1.8 Hz, 1H), 6.68 (dd, J=9.0, 2.3 Hz, 1H), 6.53 (d, J=2.0 Hz, 1H), 6.48 (q, J=1.8 Hz, 1H), 6.39 (d, J=1.5 Hz, 1H), 3.47 (q, J=7.1 Hz, 4H), 2.93 (m, 1H), 2.17 (s, 3H), 1.29 (s, 3H), 1.27 (s, 3H), 1.25 (t, J=7.2 Hz, 6H); $^{13}$C NMR (100 MHz, CDCl$_3$): δ (ppm) 170.1, 169.4, 169.1, 169.0, 163.0, 161.3, 155.9, 152.9, 148.8, 145.9, 139.4, 132.5, 131.4, 127.5, 124.8, 118.1, 116.4, 116.4, 109.7, 45.2, 16.0, 20.9, 14.1, 12.4; LRMS (ESI) m/z (%): 605.0 ([M+Na]$^+$); HRMS (ESI): calcd for $C_{32}H_{30}N_4NaO_7$: 605.2012. found: 605.1999.

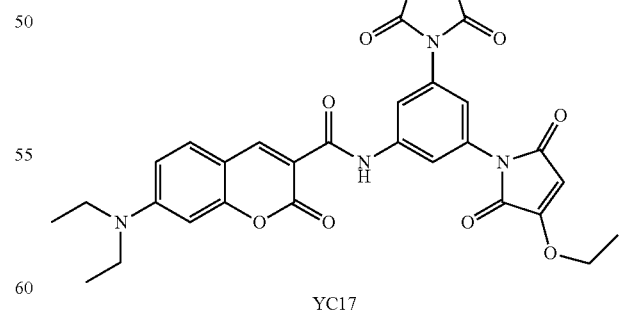

YC17

The compound YC17 was synthesized in 35% yield from the reaction of 28 (1.5 equiv) according to the general procedure. $^1$H NMR (400 MHz, CDCl$_3$): δ (ppm) 11.03 (s, 1H), 8.75 (s, 1H), 7.87 (s, 1H), 7.80 (s, 1H), 7.45 (d, J=9.0 Hz, 1H), 7.22 (m, 1H), 6.66 (dd, J=8.9, 2.1 Hz, 1H), 6.52 (d, J=1.9 Hz, 1H), 6.48 (d, J=1.7 Hz, 1H), 5.53 (s, 1H), 4.21 (q, J=7.1 Hz, 2H), 3.46 (q, J=7.1 Hz, 4H), 2.17 (s, 3H), 1.53 (t, J=7.0 Hz, 3H), 1.25 (t, J=7.1 Hz, 6H); $^{13}$C NMR (100 MHz, CDCl$_3$): δ (ppm) 170.0, 169.0, 168.6, 161.3, 159.8, 157.8, 152.9, 148.8, 145.8, 139.4, 132.6, 131.4, 127.5, 118.2, 116.5, 116.5, 110.2, 109.7, 108.6, 96.6, 96.5, 68.6, 45.2, 13.9, 12.4, 11.2; LRMS (ESI) m/z (%): 585.1 ([M+H]$^+$); HRMS (ESI): calcd for C$_{31}$H$_{29}$N$_4$O$_8$: 585.1928. found: 585.1985.

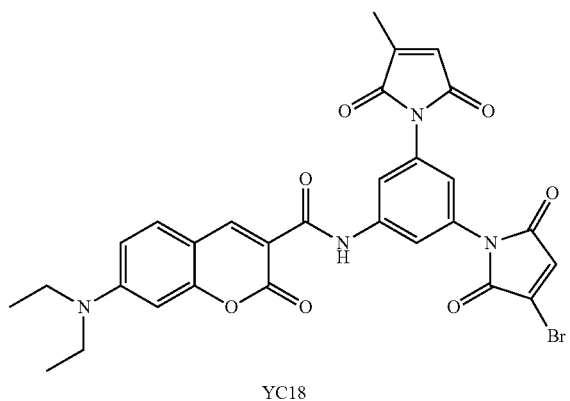 [SMILES: CCN(CC)c1ccc2cc(C(=O)Nc3cc(N4C(=O)C=C(C)C4=O)cc(N4C(=O)C=C(Br)C4=O)c3)c(=O)oc2c1 ; "YC18"]

YC18

The compound YC18 was synthesized in 55% yield from the reaction of commercially available bromomaleic anhydride (1.0 equiv) according to the general procedure. $^1$H NMR (400 MHz, CDCl$_3$): δ (ppm) 11.08 (s, 1H), 8.76 (s, 1H), 7.85 (dd, J=9.2, 1.8 Hz, 2H), 7.46 (d, J=9.0 Hz, 1H), 7.22 (t, J=1.8 Hz, 1H), 7.03 (s, 1H), 6.67 (dd, J=8.9, 2.3 Hz, 1H), 6.53 (d, J=2.1 Hz, 1H), 6.49 (d, J=1.8 Hz, 1H), 3.47 (q, J=7.1 Hz, 4H), 2.18 (d, J=1.7 Hz, 3H), 1.25 (t, J=7.0 Hz, 6H); $^{13}$C NMR (100 MHz, CDCl$_3$): δ (ppm) 170.0, 168.9, 166.8, 161.4, 157.9, 153.0, 148.9, 145.9, 139.6, 131.9, 131.5, 127.6, 118.1, 116.8, 116.4, 110.3, 109.6, 108.6, 96.7, 45.2, 12.4, 11.2; LRMS (ESI) m/z (%): 641.0 ([M+Na]$^+$); HRMS (ESI): calcd for C$_{29}$H$_{23}$BrN$_4$NaO$_7$: 641.0648. found: 641.0659.

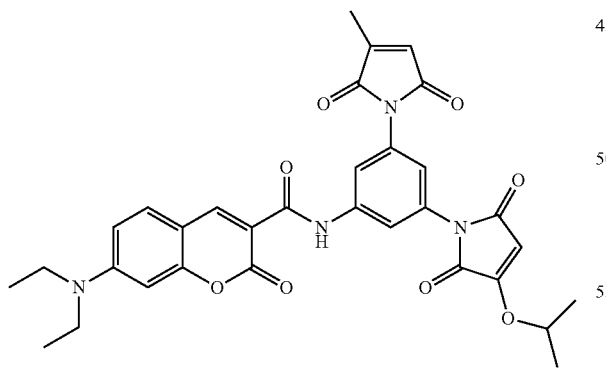

YC19

The compound YC19 was synthesized in 53% yield from the reaction of 29 (1.0 equiv) according to the general procedure. $^1$H NMR (400 MHz, CDCl$_3$): δ (ppm) 11.00 (s, 1H), 8.74 (s, 1H), 7.85 (s, 1H), 7.76 (s, 1H), 7.44 (d, J=8.9 Hz, 1H), 7.20 (s, 1H), 6.64 (dd, J=8.8, 1.9 Hz, 1H), 6.50 (d, J=1.2 Hz, 1H), 6.46 (d, J=1.4 Hz, 1H), 5.45 (s, 1H), 4.51 (m, 1H), 3.45 (q, J=7.2 Hz, 4H), 2.15 (s, 3H), 1.46 (s, 3H), 1.44 (s, 3H), 1.23 (t, J=7.2 Hz, 6H); $^{13}$C NMR (100 MHz, CDCl$_3$): δ (ppm) 170.0, 168.9, 163.0, 161.2, 158.8, 157.8, 152.9, 148.8, 145.8, 139.4, 132.1, 131.4, 127.5, 118.3, 116.6, 116.4, 110.2, 109.8, 108.6, 96.6, 96.1, 45.2, 21.2, 12.4, 11.2; LRMS (ESI) m/z (%): 621.2 ([M+Na]$^+$); HRMS (ESI): calcd for C$_{32}$H$_3$ON$_4$NaO$_8$: 621.1961. found: 621.1943.

Synthesis of YC20/YC21M.

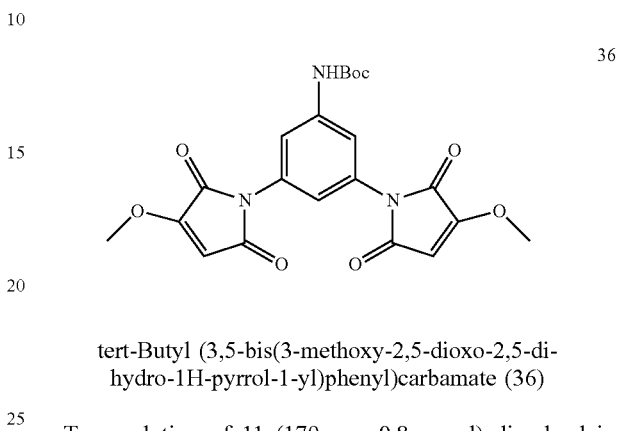

tert-Butyl (3,5-bis(3-methoxy-2,5-dioxo-2,5-di-hydro-1H-pyrrol-1-yl)phenyl)carbamate (36)

To a solution of 11 (179 mg, 0.8 mmol) dissolved in CHCl$_3$ (4 mL) 3-methoxyfuran-2,6-dione (256 mg, 2 mmol) was added and the mixture was stirred at room temperature for 3 h. The solution was then concentrated, resuspended in ether and washed with ether. The residue was dried in vacuo and dissolved in DMF (4 mL) and toluene (40 mL) prior to adding ZnCl$_2$ (327 mg, 2.4 mmol) and HMDS (0.75 mL, 2.6 mmol) in 20 mL toluene. The mixture was heated to 130° C. and stirred for 3 h after which an extraction was performed with EtOAc (3×40 mL) and 1 M HCl (40 mL). The collected organic layers were washed with Na$_2$CO$_3$ (40 mL) and brine (40 mL) and dried with MgSO$_4$ followed by evaporation. 36 was purified from the residue by flash chromatography as a beige solid (143 mg, 0.8 mmol, 40%). $^1$H NMR (300 MHz, CDCl$_3$): δ (ppm) 7.43 (d, J=1.71 Hz, 2H), 7.14 (t, J=1.86, 1.83 Hz, 1H), 6.58 (s, 1H), 5.54 (s, 2H), 3.98 (s, 6H), 1.48 (s, 9H). $^{13}$C NMR (75 MHz, CDCl$_3$): δ (ppm) 168.3, 163.8, 160.7, 152.2, 139.6, 132.1, 117.0, 114.6, 96.6, 81.2, 59.2, 28.3; LRMS (EI) m/z (%): 443.1 (M$^+$, 0.8%); HRMS (EI): calcd for C$_{21}$H$_{21}$N$_3$O$_8$: 443.1329. found: 443.1303.

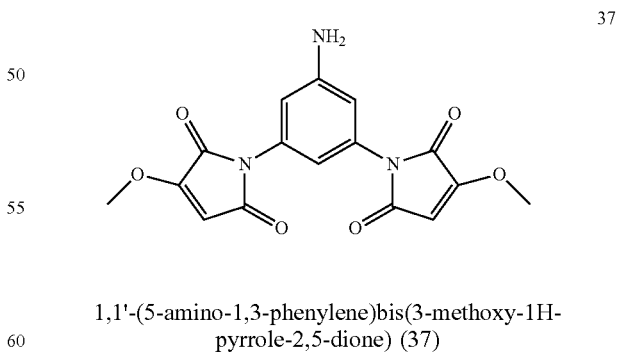

1,1'-(5-amino-1,3-phenylene)bis(3-methoxy-1H-pyrrole-2,5-dione) (37)

36 was dissolved in DCM (3 mL) and to this TFA (3 mL) was added and the mixture was stirred for 2 h at room temperature. The solution was evaporated and diluted with CHCl$_3$ (30 mL), re-evaporated and re-dissolved in EtOAc (60 mL). The solution was washed with NaHCO$_3$ (20 mL) and brine (20 mL) before drying with MgSO$_4$ and purification by flash chromatography to produce a white solid (58 mg, 54%). $^1$H NMR (400 MHz, CD$_3$CN): δ (ppm) 6.59 (d, J=1.76 Hz, 2H), 6.54 (t, J=1.84, 1.76 Hz, 1H), 5.67 (s, 2H), 3.96 (s, 6H). $^{13}$C NMR (100 MHz, CD$_3$CN): δ (ppm) 169.2, 164.4, 161.3, 132.7, 113.5, 111.9, 96.7, 59.2, 29.9; LRMS (EI) m/z (%): 343.1 (M$^+$, 13.1%); HRMS (D): calcd for C$_{16}$H$_{13}$N$_3$O$_6$: 343.0804. found: 343.0790.

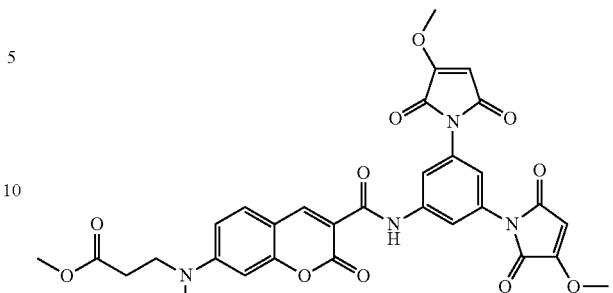

YC21M

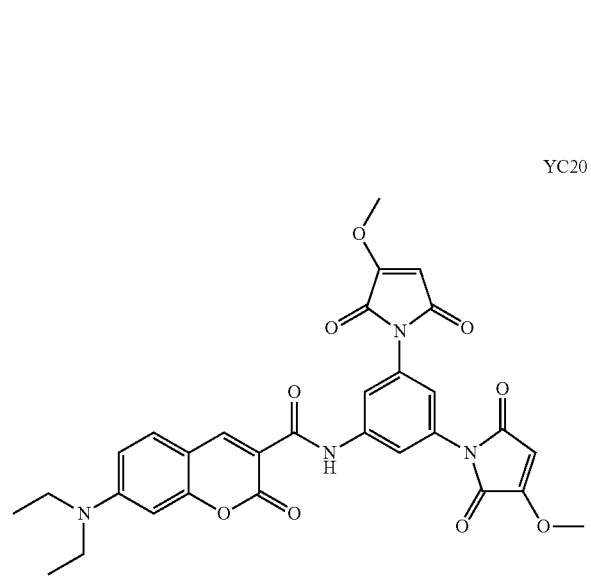 [SMILES: CCN(CC)c1ccc2cc(C(=O)Nc3cc(N4C(=O)C=C(OC)C4=O)cc(N4C(=O)C=C(OC)C4=O)c3)c(=O)oc2c1]

YC20

N-(3,5-bis(3-methoxy-2,5-dioxo-2,5-dihydro-1H-pyrrol-1-yl)phenyl)-7-(diethylamino)-2-oxo-2H-chromene-3-carboxamide (YC20)

Under N$_2$ and in anhydrous conditions, 7-(diethylamino) coumarin-3-carboxylic acid (26.00 mg, 0.1 mmol) was dissolved in DCE (1.0 mL) and POCl$_3$ (28 μL, 0.3 mmol) was added to the solution before the mixture was heated to reflux and stirred for 4 h. After, the solution was concentrated and the residue dried in vacuo. Following this, the residue was dissolved in pyridine and 37 (35.00 mg, 0.1 mmol) was added and the mixture was stirred overnight at room temperature. The mixture was evaporated and YC20 was purified by flash chromatography to produce a yellow solid (32 mg, 55%). $^1$H NMR (DMSO, 400 MHz) δ: 10.90 (s, 1H), 8.70 (s, 1H), 7.73 (d, J=1.8 Hz, 2H), 7.70 (d, J=9.1 Hz, 1H) 7.05 (t, J=1.8 Hz, 1H), 6.84 (dd, J=2.3, 9.0 Hz, 1H), 6.65 (d, J=2.2 Hz, 1H), 6.04 (s, 2H), 3.94 (s, 6H), 3.48 (q, J=4, 8 Hz, 4H), 1.20 (m, 6H) ppm; $^{13}$C NMR (400 MHz, DMSO): δ (ppm) 169.4, 164.4, 162.7, 161.5, 157.9, 153.4, 148.8, 139.3, 132.6, 132.4, 120.5, 118.4, 117.4, 111.0, 109.3, 108.4, 97.8, 96.5, 59.9, 44.9, 12.8. LRMS (ESI) m/z (%): 587.0 (M$^+$); HRMS (ESI): calcd for C$_{30}$H$_{26}$N$_4$O$_9$: 586.1700. found: 587.0454.

Dimethyl 3,3'-((3-((3,5-bis(3-methoxy-2,5-dioxo-2,5-dihydro-1H-pyrrol-1-yl)phenyl)carbamoyl)-2-oxo-2H-chromen-7-yl)azanediyl)dipropanoate (YC21M)

The synthesis of YC21M followed the same protocol for the synthesis of YC20 starting with compounds 21 and 37. (42 mg, 38% yield). $^1$H NMR (400 MHz, CDCl$_3$) δ (ppm): 10.95 (s, 1H), 8.78 (s, 1H), 7.80 (s, 2H), 7.49 (s, 1H), 7.23 (s, 1H), 6.70 (s, 1H), 6.54 (s, 1H), 5.56 (s, 2H), 3.98 (s, 6H), 3.77 (s, 4H), 3.69 (s, 6H), 2.64 (s, 4H); $^{13}$C NMR (100 MHz, CDCl$_3$) δ (ppm) 171.6, 168.3, 163.8, 162.6, 160.8, 160.7, 157.5, 152.2, 148.9, 139.2, 132.0, 131.6, 118.5, 116.7, 111.3, 110.5, 109.4, 97.6, 96.6, 59.1, 52.1, 47.0, 31.9; LRMS (ESI) m/z: 725.16 ([M+Na]$^+$); HRMS (ESI): calcd for C$_{34}$H$_{30}$N$_4$NaO$_{13}$: 725.1702. found: 725.1707.

TABLE 4

| Abbreviations. | |
|---|---|
| ACN | acetonitrile |
| Ac$_2$O | acetic anhydride |
| AcOH | acetic acid |
| aq | aqueous |
| Boc | tert-butoxycarbonyl |
| calcd | calculated |
| DCE | dichloroethane |
| DCM | dichloromethane |
| DIPEA | diisopropylethylamine |
| DMAP | 4-dimethylaminopyridine |
| DMF | N,N-dimethylformamide |
| DMP | Dess-Martin periodinane |
| DMSO | dimethyl sulfoxide |
| EDC•HCl | N-ethyl-N'-(3-dimethylaminopropyl)carbodiimide hydrochloride |
| EI | electron ionization |
| em | emission |
| eq or equiv | equivalence |
| ESI | electrospray ionization |
| EtOAc or EA | ethyl acetate |
| Et | ethyl |
| EtO or OEt | ethoxy |
| ex | excitation |
| GSH | glutathione |
| h | hour |
| HEK | human embryonic kidney |
| HEPES | 4-(2-hydroxyethyl)-1-piperazineethanesulfonic acid |
| HMDS | hexamethyldisilazane |
| HOBt | hydroxybenzotriazole |
| HRMS | high-resolution mass spectrometry |

TABLE 4-continued

| Abbreviations. | |
|---|---|
| LRMS | low-resolution mass spectrometry |
| MBP | maltose-binding protein |
| Me | methyl |
| MeO or OMe | methoxy |
| MTT | 3-(4,5-dimethylthiazol-2-yl)-2,5-diphenyltetrazolium bromide |
| NMR | nuclear magnetic resonance |
| OiPr | isopropoxy |
| Ph | phenyl |
| iPr | isopropyl |
| r.t. | room temperature |
| sat. | saturated |
| mean ± SD | standard deviation of the mean |
| TBTU | N,N,N',N'-tetramethyl-O-(benzotriazol-1-yl)uronium tetrafluoroborate |
| THF | tetrahydrofuran |
| TEA | triethylamine |
| TFA | trifluoroacetic acid |
| Tol | toluene |

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A fluorogenic labelling agent which is a compound of Formula I, or a salt thereof:

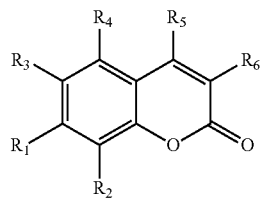

(I)

wherein:

R$_1$ is OR$_1$' or NR$_2$'R$_3$', wherein R$_1$', R$_2$' and R$_3$' are independently selected from hydrogen, alkyl, alkenyl, alkynyl, cycloalkyl, cycloalkenyl, cycloalkynyl, aryl, alkaryl, arylalkyl, and carboxy alkyl, alkyl being optionally substituted by hydroxyl, amino, carboxyl, carboxylic ester, amide, carbamate, or aminoalkyl; or R$_1$' and R$_2$ or R$_1$' and R$_3$ come together to form a 5, 6 or 7-membered ring which is selected from aryl, heterocyclic, heteroaryl, and heteroaromatic; or R$_2$', R$_2$, R$_3$', and R$_3$ come together independently to form at least one 5, 6 or 7-membered ring which is selected from aryl, heterocyclic, heteroaryl and heteroaromatic;

R$_2$, R$_3$ and R$_4$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, alkyl being optionally substituted by hydroxyl, amino, carboxyl, carboxylic ester, amide, carbamate, or aminoalkyl;

R$_5$ and R$_6$ are independently selected from hydrogen, halogen, alkyl, alkoxy, keto, carboxylate, carboxylic ester, carbamate, amide, amino, alkylamino, polyether, alkylthio, cyano, nitro, sulfonyl, X$_1$, and X$_2$, wherein both R5 and R6 are X1, both R5 and R6 are X2 or only one of R$_5$ and R$_6$ is X$_1$ or X$_2$, and alkyl is optionally substituted by hydroxyl, amino, carboxyl, carboxylic ester, amide, carbamate, or aminoalkyl;

X$_1$ is

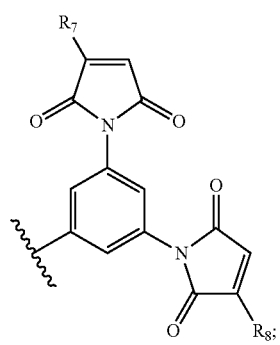

X$_2$ is

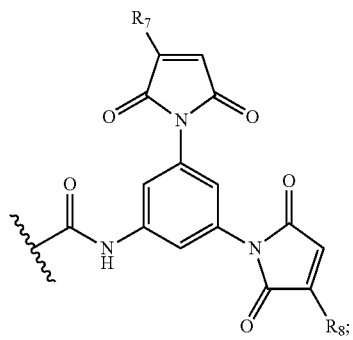

and

R$_7$ and R$_8$ are independently R$_9$ or OR$_{10}$, wherein R$_9$ is selected from hydrogen, halogen, and alkyl, alkyl being optionally substituted by hydroxyl, amino, carboxyl, carboxylic ester, amide, carbamate, or aminoalkyl, and R$_{10}$ is alkyl, alkyl being optionally substituted by hydroxyl, amino, carboxyl, carboxylic ester, amide, carbamate, or aminoalkyl.

2. The fluorogenic labelling agent of claim 1, wherein: at least one of R$_7$ and R$_8$ is OR$_{10}$; R$_7$ and R$_8$ are the same; R$_9$ and R$_{10}$ are the same; when R$_7$ is OR$_{10}$, R$_8$ is R$_9$; or, when R$_7$ is R$_9$, R$_8$ is OR$_{10}$.

3. The fluorogenic labelling agent of claim 1, wherein: R$_5$ is X$_1$ or X$_2$ and R$_6$ is hydrogen; R$_5$ is hydrogen and R$_6$ is X$_1$ or X$_2$; R$_5$ and R$_6$ are both X$_1$ or X$_2$; one of R$_5$ and R$_6$ is X$_1$ and the other is X$_2$; or, wherein R$_5$ is hydrogen; R$_6$ is X$_2$; R$_7$ is methyl; and R$_8$ is methoxy; or, wherein R$_5$ is hydrogen; R$_6$ is X$_2$; and R$_7$ and R$_8$ are methoxy; or, wherein R$_2$, R$_3$, and R$_4$ are hydrogen.

4. The fluorogenic labelling agent of claim 1, wherein R$_1$ is selected from:

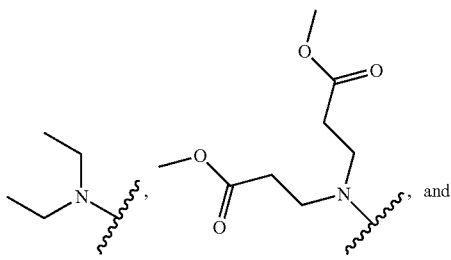

or wherein R$_1$ is selected from:

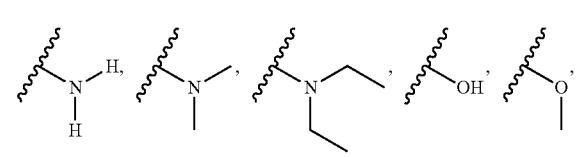

-continued

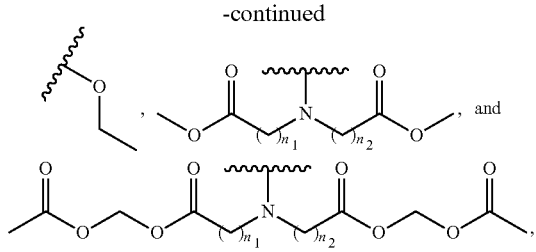, and where $n_1$ and $n_2$ are independently 1 or higher than 1.

5. The fluorogenic labelling agent of claim 1, wherein said fluorogenic labelling agent is a compound of Formula II, or a salt thereof:

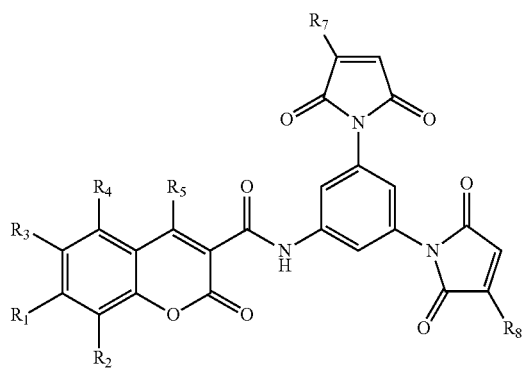

(II)

wherein:
$R_1$, $R_2$, $R_3$, $R_4$, $R_7$, and $R_8$ are as defined in claim 1; and
$R_5$ is selected from hydrogen, halogen, alkyl, alkoxy, keto, carboxylate, carboxylic ester, carbamate, amide, amino, alkylamino, polyether, alkylthio, cyano, nitro, and sulfonyl, wherein alkyl is optionally substituted by hydroxyl, amino, carboxyl, carboxylic ester, amide, carbamate, or aminoalkyl.

6. The fluorogenic labelling agent of claim 1, wherein said fluorogenic labelling agent is a compound of Formula III, or a salt thereof:

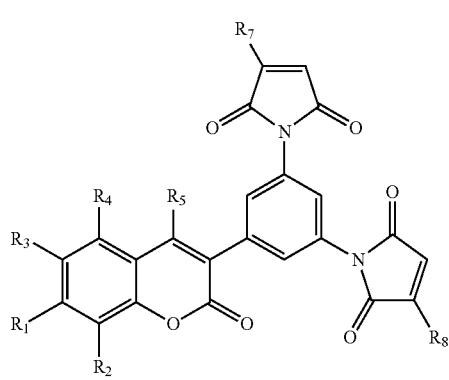

(III)

wherein:
$R_1$, $R_2$, $R_3$, $R_4$, $R_7$, and $R_8$ are as defined in claim 1; and
$R_5$ is selected from hydrogen, halogen, alkyl, alkoxy, keto, carboxylate, carboxylic ester, carbamate, amide, amino, alkylamino, polyether, alkylthio, cyano, nitro, and sulfonyl, wherein alkyl is optionally substituted by hydroxyl, amino, carboxyl, carboxylic ester, amide, carbamate, or aminoalkyl.

7. The fluorogenic labelling agent of claim 5, wherein $R_7$ and $R_8$ are the same; $R_9$ and $R_{10}$ are the same; when $R_7$ is $OR_{10}$, $R_8$ is $R_9$; when $R_7$ is $R_9$, $R_8$ is $OR_{10}$; at least one of $R_7$ and $R_8$ is $OR_{10}$; $R_7$ is methyl and $R_8$ is methoxy; or, both $R_7$ and $R_8$ are methoxy.

8. The fluorogenic labelling agent of claim 5, wherein $R_2$, $R_3$, and $R_4$ are hydrogen; $R_5$ is hydrogen; or, $R_1$ is selected from:

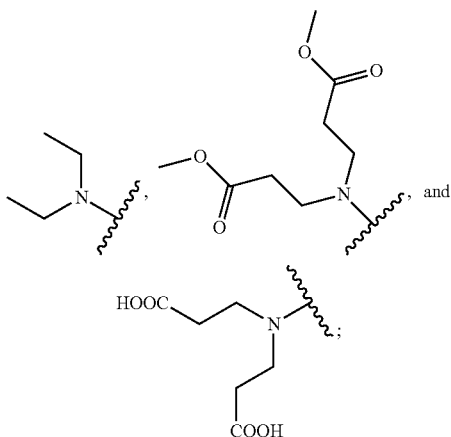

or
wherein $R_1$ is selected from:

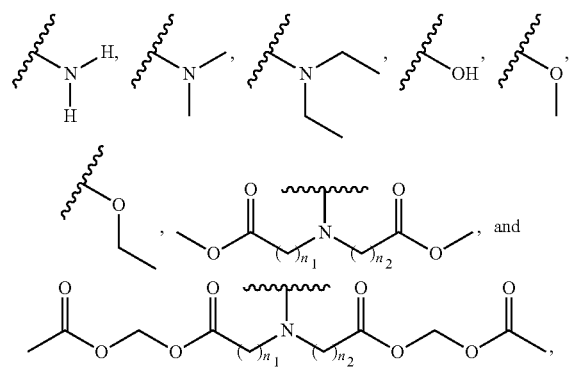

where $n_1$ and $n_2$ are independently 1 or higher than 1.

9. The fluorogenic labelling agent of claim 5, wherein $R_2$, $R_3$, and $R_4$ are hydrogen, and $R_1$ is selected from:

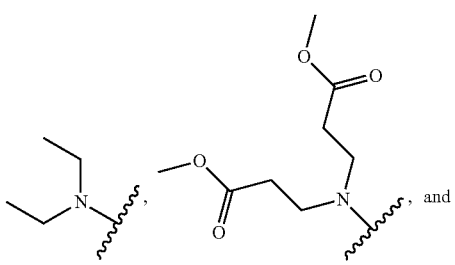

-continued

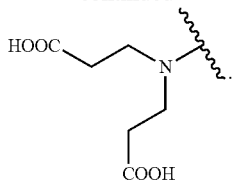

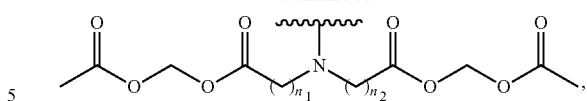

where $n_1$ and $n_2$ are independently 1 or higher than 1.

12. The fluorogenic labelling agent of claim 1, wherein said fluorogenic labelling agent is selected from:

10. The fluorogenic labelling agent of claim 1, wherein $R_2$, $R_3$, and $R_4$ are hydrogen, and $R_1$ is selected from:

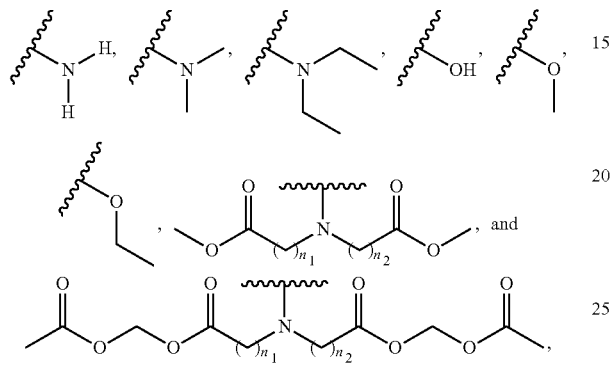

where $n_1$ and $n_2$ are independently 1 or higher than 1.

11. The fluorogenic labelling agent of claim 5, wherein $R_2$, $R_3$, $R_4$, and $R_5$ are hydrogen; $R_7$ is methyl or methoxy; $R_8$ is hydrogen, methyl or methoxy; and $R_1$ is selected from:

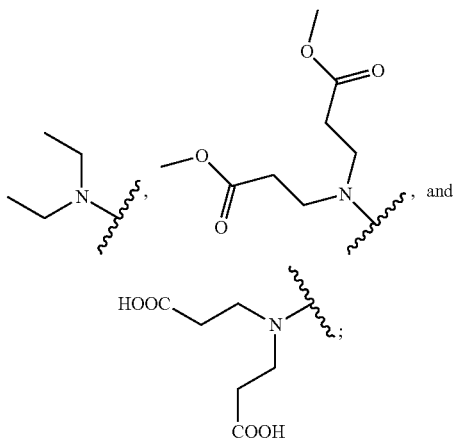

or
wherein $R_1$ is selected from:

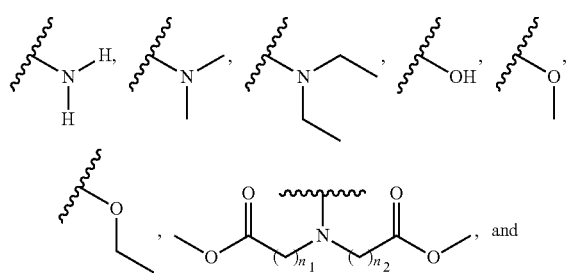

YC24

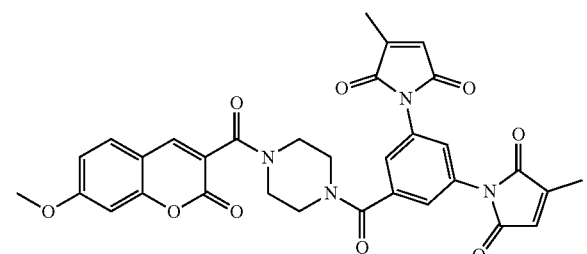

YC25

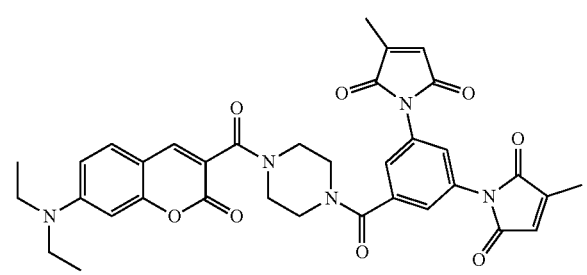

YC26

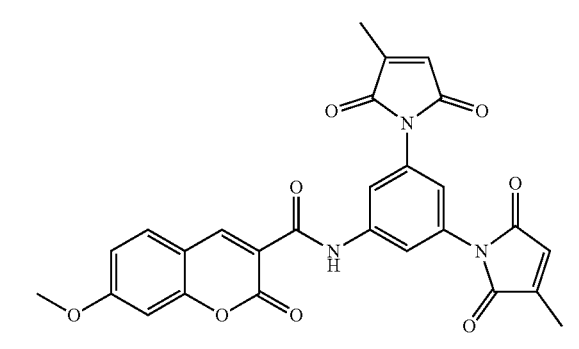

YC5

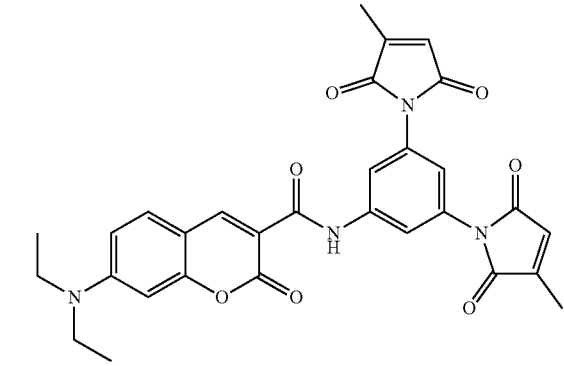

YC9

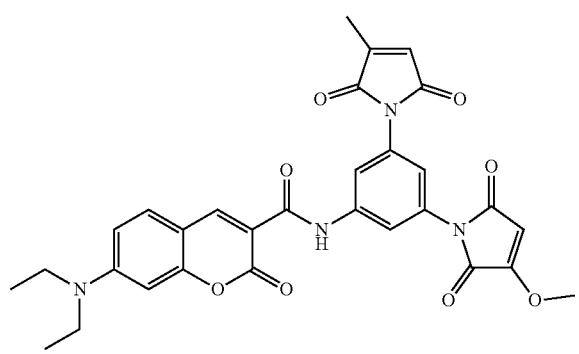

YC9M

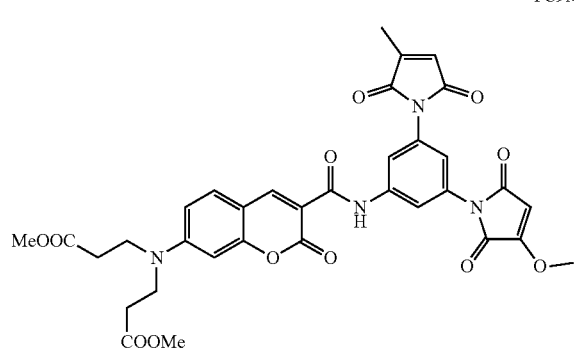

YC9A

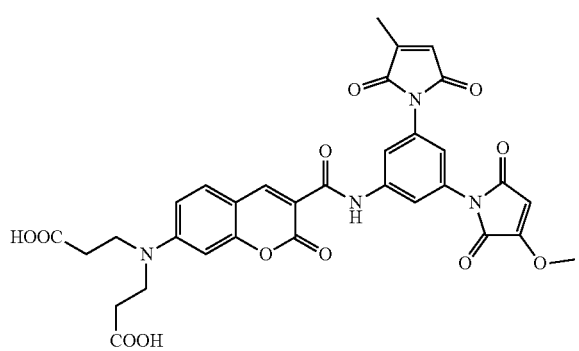

YC21A

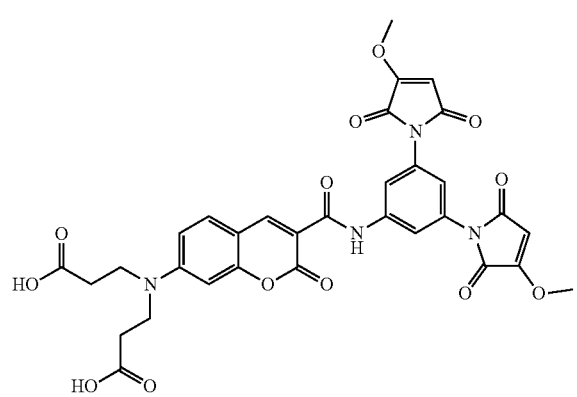

YC15-YC19

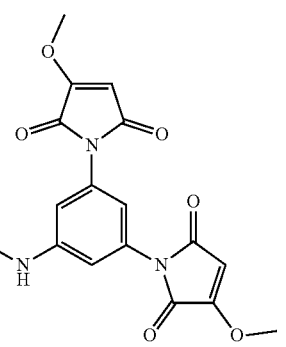

R = Et YC15
  ⁱPr YC16
  OEt YC17
  Br YC18
  OⁱPr YC19

YC20

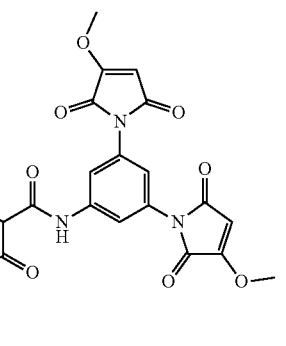

YC21M

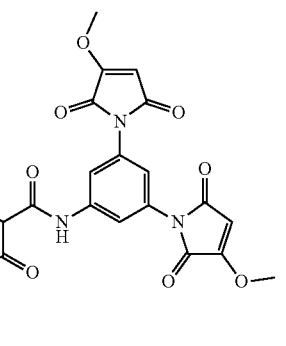

and salts thereof.

13. A method for labelling and/or detecting a target protein, comprising:
  a) contacting the target protein with the fluorogenic labelling agent of claim 1, under conditions where the fluorogenic labelling agent reacts with sterically unhindered sulfhydryl groups on the target protein; and
  b) detecting a fluorescent signal from the fluorogenic labelling agent,
  wherein the fluorescence of the fluorogenic labelling agent is quenched in the absence of reaction with the target protein, and detection of the fluorescent signal indicates that reaction of the fluorogenic labelling agent with the target protein; or, wherein the fluorescence of the fluorogenic labelling agent increases after reaction with the target protein.

14. The method of claim 13, wherein said contacting occurs in vivo, ex vivo, or in vitro.

15. The method of claim 13, wherein the target protein comprises two Cys residues separated by about 10 Å; wherein the target protein comprises a dC10α tag; or, wherein the target protein has been genetically engineered to comprise two Cys residues separated by about 10 Å or a dC10α tag.

16. The method of claim 13, wherein said contacting occurs in a cultured cell expressing the target protein; and/or, wherein said contacting occurs intracellularly; and/or, wherein said target protein is an intracellular protein, an extracellular protein, or a cell-surface protein.

17. A method for live imaging of a target protein, comprising:
 a) contacting the target protein with the fluorogenic labelling agent of claim 1, under conditions where the fluorogenic labelling agent reacts with sterically unhindered sulfhydryl groups on the target protein; and
 b) detecting a fluorescent signal from the fluorogenic labelling agent,
 wherein:
 the fluorescence of the fluorogenic labelling agent increases after reaction with the target protein, or is detectable only after reaction with the target protein.

* * * * *

SEQUENCE LISTING

<160> NUMBER OF SEQ ID NOS: 2

<210> SEQ ID NO 1
<211> LENGTH: 192
<212> TYPE: DNA
<213> ORGANISM: Artificial Sequence
<220> FEATURE:
<223> OTHER INFORMATION: dC10alpha-actin gBlock

<400> SEQUENCE: 1

```
tataagcaga gctggtttag tgaaccgtca gatccgctag cgatgctgag cgctgctgag       60
tgcgctgcta gagaagctgc atgcagagaa gctgcagcta gagctggagg aaagggatct      120
tcactcgagg atgatgatat cgccgcgctc gtcgtcgaca acggctccgg catgtgcaag      180
gccggcttcg cg                                                           192
```

<210> SEQ ID NO 2
<211> LENGTH: 192
<212> TYPE: DNA
<213> ORGANISM: Artificial Sequence
<220> FEATURE:
<223> OTHER INFORMATION: H2B-dC10alpha gBlock

<400> SEQUENCE: 2

```
catgctgtgt ccgagggcac taaggcagtt accaagtaca ctagctctaa ggatccagga       60
tcttcactga gcgctgctga gtgcgctgct agagaagctg catgcagaga agctgcagct      120
agagctggag gaaagtaatc tagagggccc tattctatag tgtcacctaa atgctagagc      180
tcgctgatca gc                                                           192
```